US010351593B2

(12) United States Patent
Han et al.

(10) Patent No.: US 10,351,593 B2
(45) Date of Patent: Jul. 16, 2019

(54) DERIVATIVES OF DOLASTATIN 10 AND USES THEREOF

(71) Applicant: NewBio Therapeutics, Inc., Shanghai (CN)

(72) Inventors: Nianhe Han, Shanghai (CN); Deqiang An, Shanghai (CN); Peng Zhu, Shanghai (CN); Chengyu Hou, Shanghai (CN); Hang Yang, Shanghai (CN); Li Jian, Shanghai (CN); Chun Yang, Shanghai (CN)

(73) Assignee: NewBio Therapeutics, Inc., Shanghai (CN)

( * ) Notice: Subject to any disclaimer, the term of this patent is extended or adjusted under 35 U.S.C. 154(b) by 64 days.

(21) Appl. No.: 15/577,500

(22) PCT Filed: May 17, 2016

(86) PCT No.: PCT/CN2016/082286
§ 371 (c)(1),
(2) Date: Nov. 28, 2017

(87) PCT Pub. No.: WO2016/192527
PCT Pub. Date: Dec. 8, 2016

(65) Prior Publication Data
US 2018/0141973 A1 May 24, 2018

(30) Foreign Application Priority Data
May 29, 2015 (CN) .......................... 2015 1 0290667

(51) Int. Cl.
*C07K 5/062* (2006.01)
*A61K 47/68* (2017.01)
*C07K 7/02* (2006.01)
*C07K 16/32* (2006.01)
*A61K 38/00* (2006.01)

(52) U.S. Cl.
CPC ...... *C07K 5/06034* (2013.01); *A61K 47/6817* (2017.08); *A61K 47/6851* (2017.08); *C07K 7/02* (2013.01); *C07K 16/32* (2013.01); *A61K 38/00* (2013.01); *C07K 2317/73* (2013.01)

(58) Field of Classification Search
None
See application file for complete search history.

(56) References Cited

FOREIGN PATENT DOCUMENTS

| JP | 2014516508 A | 7/2014 |
|---|---|---|
| WO | 2013173393 A1 | 11/2013 |
| WO | 2014086952 A1 | 6/2014 |
| WO | 2016205738 A2 | 12/2016 |

OTHER PUBLICATIONS

Partial Supplementary European Search Report issued in corresponding European Application No. 16802450.3, dated Dec. 4, 2018, 12 pages.
Notification of Reasons for Refusal issued in corresponding Japanese Application No. 2018-511320, dated Dec. 4, 2018, 7 pages.
Batisse, et al., A New Delivery System for Auristatin in STxB-drug Conjugate Therapy, European Journal of Medicinal Chemistry, 2015, 95:483-491.
Doronina, et al., Enhanced Activity of Monomethylauristatin F Through Monoclonal Antibody Delivery: Effects of Linker Technology on Efficacy and Toxicity, Bioconjugate Chemistry, 2006,17(1):114-124.
PCT International Search Report and Written Opinion, PCT/CN2016/082286, dated Jul. 26, 2016.

*Primary Examiner* — Karl J Puttlitz
(74) *Attorney, Agent, or Firm* — Quarles & Brady LLP

(57) ABSTRACT

Derivatives of dolastatin 10 and uses thereof, the structures of which are shown as formula I, II, III and IV are provided.

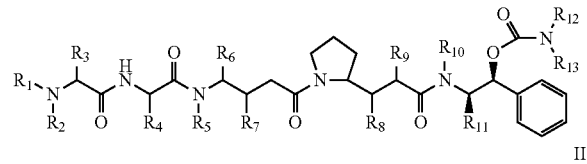

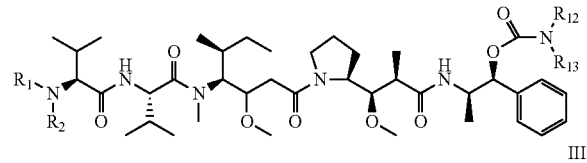

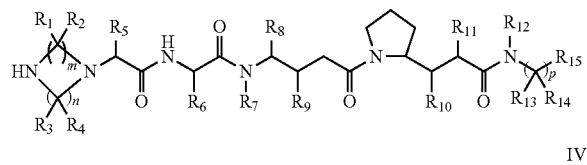

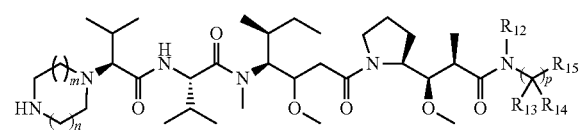

18 Claims, No Drawings

DERIVATIVES OF DOLASTATIN 10 AND USES THEREOF

CROSS-REFERENCE TO RELATED APPLICATIONS

This application represents the U.S. national stage entry of International Application No. PCT/CN2016/082286 filed May 17, 2016, which claims priority to Chinese Patent Application No. 201510290667.4 filed May 29, 2015, the disclosure of which is incorporated herein by reference in its entirety and for all purposes.

FIELD OF THE INVENTION

The invention relates to the design and synthesis of the derivatives of dolastatin 10 as cytotoxic drugs, and the application of these drugs in antibody-drug conjugates (ADCs).

BACKGROUND OF THE INVENTION

As a novel targeted therapy, ADC has gained fast development in recent years. So far there have been three ADC drugs (Mylotarg, Adcetris, and Kadeyla) approved by FDA, and more than 30 ADC drug candidates are in clinical trials worldwide.

An ADC drug is composed of three independent parts: an antibody or antibody-like ligand, high-potency cytotoxic drugs, and linkers that conjugate the drugs to the ligand. The mechanism of action (MOA) of an antibody-drug conjugate is described as follows. An antibody or antibody-like ligand targets specific cell surface protein receptors (antigens). Once binding to the antigens, the binding complex will internalize and thus deliver the linked drugs into the cell. The antibody or antibody-like ligand will be digested by enzymes, or the linkers will be cleaved, via either way the high-potency cytotoxic drugs could be released in an active form and kill the cells.

Cytotoxic drugs used in ADCs are required to be highly potent, normally 10-1000 folds higher than those first-line chemotherapy drugs in use. Currently used cytotoxic drugs mainly target cell microtubules or DNAs. Cytotoxic drugs targeting microtubules generally inhibit cell mitosis and thus lead to cell death, which include maytansinoids (EP 0425235; U.S. Pat. Nos. 5,208,020, 5,416,064; 7,276,497, 7,473,796, 7,851,432; US 2007/0269447, 2011/0158991; WO 2004/103272, 2012/061590) and auristatins (dolastatin 10 derivatives, U.S. Pat. Nos. 6,884,869, 7,498,298), etc. Cytotoxic drugs targeting DNAs generally kill the cells by DNA synthesis inhibition, minor-groove binding and alkylating, and DNA breaking, etc, which include doxorubicins (Bioconjugate Chem. 2002, 13, 855-869), calicheamicins (U.S. Pat. Nos. 5,606,040, 5,770,710), duocarmycins and CC-1065 (U.S. Pat. No. 7,129,261), and PBD dimers (WO 2005/040170), etc.

Around 70-80% of ADCs approved by FDA and in clinical trials adopts auristatins and maytansinoids as high-potency warheads. Maytansinoids are synthesized from ansamitocin (P-3), which is produced by fermentation, requiring high-production strains and optimized fermentation conditions. Auristatins can be produced by total synthesis and thus more convenient for scale production.

The representative auristatins are mono-methyl auristatin E (MMAE, U.S. Pat. No. 6,884,869) and mono-methyl auristatin F (MMAF, U.S. Pat. No. 7,498,298), both of which are pentapeptide derivatives of dolastatin 10, while the latter was isolated from the marine mollusk *Dolabella auricularia* and found to be highly potent cytotoxic agent. Besides widely used MMAE and MMAF mentioned above, other analogs of dolastatin 10 were also reported. WO 2006/132670 disclosed derivatives with N-terminal valine substituted by p-aminobenzoic acid. WO 2007/008603, WO 2007/008848, US 2013/0123456 and WO 2013/173393 disclosed a series of derivatives with C-terminal modification on phenylalanine. WO 2011/154359 and WO 2012/041805 disclosed derivatives based on structural modification on both N-terminal and C-terminal of MMAF.

Due to the high potency requirement for cytotoxic agents (for ADCs), both types and amounts of cytotoxic drug candidates are relatively few, which somehow limit the development of ADCs. Therefore, more potent cytotoxic agents are required by this area. Development of novel cytotoxic drugs based on current cytotoxic agent is of great importance and application prospect.

SUMMARY OF THE INVENTION

The invention aims at providing new dolastatin 10 derivative type cytotoxic drugs and their application in ADCs. In the first aspect, this invention disclosed compounds of formula I:

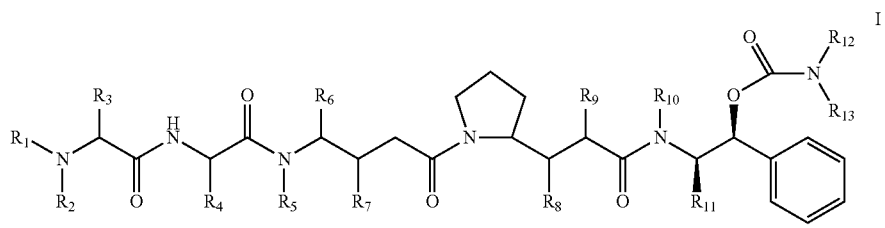

wherein
$R_1$ and $R_2$ are independently selected from H or —$C_1$-$C_8$ alkyl, or $R_1$ and $R_2$ together form a heterocycle of the formula —$(CR_{14}R_{15})_n$—Z—$(CR_{16}R_{17})_m$—, wherein $R_{14}$, $R_{15}$, $R_{16}$ and $R_{17}$ are independently selected from H or —$C_1$-$C_8$ alkyl; Z is selected from O, $NR_{18}$ or $CR_{19}R_{20}$, wherein $R_{18}$, $R_{19}$, and $R_{20}$ are independently selected from H or —$C_1$-$C_8$ alkyl; n and m are integers independently selected from 0 to 8;

$R_3$, $R_4$, and $R_6$ are independently selected from H, —$C_1$-$C_8$ alkyl, aryl, heterocycle, arylalkyl, or heteroarylalkyl;

$R_5$, $R_9$, $R_{10}$, and $R_{11}$ are independently selected from H, or —$C_1$-$C_8$ alkyl;

$R_7$ and $R_8$ are independently selected from H, —OH, —$C_1$-$C_8$ alkyl, or —O—($C_1$-$C_8$ alkyl);

$R_{12}$ and $R_{13}$ are independently selected from H, —$C_1$-$C_8$ alkyl, —$OR_{21}$, —$R_{22}X$, or $R_{12}$ and $R_{13}$ together form a heterocycle of the formula —$(CR_{23}R_{24})_p$—W—$(CR_{25}R_{26})_q$—, wherein W is selected from O, $NR_{27}$, or $CR_{28}R_{29}$; X is selected from —OH or —$NR_{30}R_{31}$; p and q are integers independently selected from 0 to 8;

$R_{21}$ is selected from H, —$C_1$-$C_8$ alkyl, aryl, heterocyclyl, arylalkyl, or heteroarylalkyl;

$R_{22}$ is selected from alkylene, alkenlene, alkynlene, arylene, —$(CH_2CH_2O)_r$—$(CH_2)_s$—, or any combination thereof;

r and s are integers independently selected from 0 to 8;

$R_{23}$, $R_{24}$, $R_{25}$, $R_{26}$, $R_{27}$, $R_{28}$, $R_{29}$ and $R_{30}$ are independently selected from H or —$C_1$-$C_8$ alkyl;

$R_{31}$ is selected from H, —$C_1$-$C_8$ alkyl, or —$OR_{32}$, wherein $R_{32}$ is selected from H, —$C_1$-$C_8$ alkyl, aryl, heterocyclyl, arylalkyl, or heteroarylalkyl.

In a preferred embodiment, the invention provides compounds of formula II

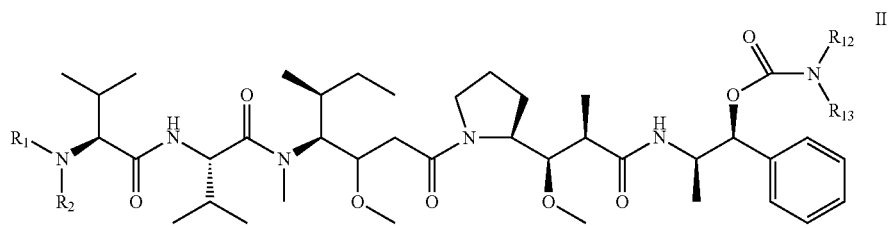

II wherein $R_1$ and $R_2$ are independently selected from H or —$C_1$-$C_8$ alkyl, or $R_1$ and $R_2$ together form a heterocycle of the formula —$(CR_{14}R_{15})_n$—Z—$(CR_{16}R_{17})_m$—, wherein $R_{14}$, $R_{15}$, $R_{16}$ and $R_{17}$ are independently selected from H or —$C_1$-$C_8$ alkyl; Z is selected from O, $NR_{18}$ or $CR_{19}R_{20}$, wherein $R_{18}$, $R_{19}$, and $R_{20}$ are independently selected from H or —$C_1$-$C_8$ alkyl; n and m are integers independently selected from 0 to 8;

$R_{12}$ and $R_{13}$ are independently selected from H, —$C_1$-$C_8$ alkyl, —$OR_{21}$, —$R_{22}X$, or $R_{12}$ and $R_{13}$ together form a heterocycle of the formula —$(CR_{23}R_{24})_p$—W—$(CR_{25}R_{26})_q$—, wherein W is selected from O, $NR_{27}$, or $CR_{28}R_{29}$; X is selected from —OH or —$NR_{30}R_{31}$; p and q are integers independently selected from 0 to 8;

$R_{21}$ is selected from H, —$C_1$-$C_8$ alkyl, aryl, heterocyclyl, arylalkyl, or heteroarylalkyl;

$R_{22}$ is selected from alkylene, alkenlene, alkynlene, arylene, —$(CH_2CH_2O)_r$—$(CH_2)_s$—, or any combination thereof;

r and s are integers independently selected from 0 to 8;

$R_{23}$, $R_{24}$, $R_{25}$, $R_{26}$, $R_{27}$, $R_{28}$, $R_{29}$ and $R_{30}$ are independently selected from H or —$C_1$-$C_8$ alkyl;

$R_{31}$ is selected from H, —$C_1$-$C_8$ alkyl, or —$OR_{32}$, wherein $R_{32}$ is selected from H, —$C_1$-$C_8$ alkyl, aryl, heterocyclyl, arylalkyl, or heteroarylalkyl.

In a preferred embodiment, the invention provides compounds 1-6 as shown below.

| Compound | Number |
|---|---|
| ![Compound 1 structure] | 1 |
| ![Compound 2 structure] | 2 |

| Compound | Number |
|---|---|
| [structure] | 3 |
| [structure] | 4 |
| [structure] | 5 |
| [structure] | 6 |

In a preferred embodiment, the invention provides compounds 7-16 as shown below.

| Compound | Number |
|---|---|
| [structure] | 7 |
| [structure] | 8 |

-continued

| Compound | Number |
|---|---|
| [chemical structure] | 9 |
| [chemical structure] | 10 |
| [chemical structure] | 11 |
| [chemical structure] | 12 |
| [chemical structure] | 13 |
| [chemical structure] | 14 |
| [chemical structure] | 15 |

| Compound | Number |
|---|---|
| 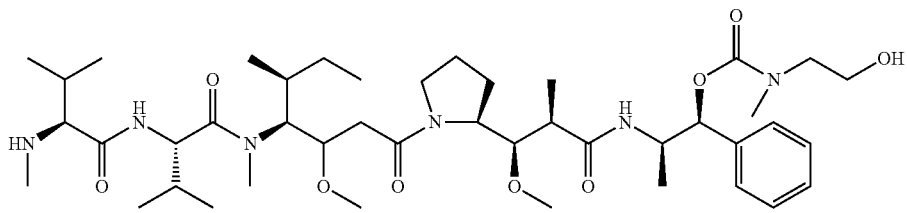 [SMILES: CC[C@H](C)[C@@H](C(CC(=O)N1CCC[C@H]1[C@H](OC)[C@@H](C)C(=O)N[C@H](C)[C@@H](OC(=O)N(C)CCO)c1ccccc1)OC)N(C)C(=O)[C@@H](NC(=O)[C@@H](NC)C(C)C)C(C)C] | 16 |

In the second aspect, the invention provides compounds of formula III:

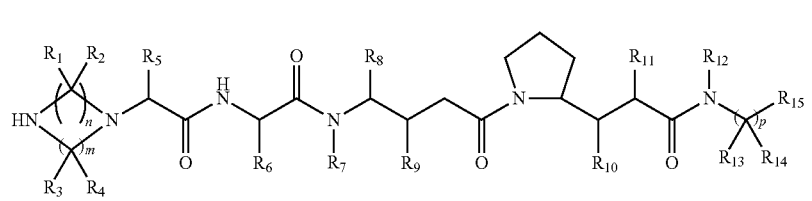

III wherein
$R_1$, $R_2$, $R_3$, and $R_4$ are independently selected from H or —$C_1$-$C_8$ alkyl;
m and n are integers independently selected from 2 to 4;
$R_5$, $R_6$, and $R_8$ are independently selected from H, —$C_1$-$C_8$ alkyl, aryl, heterocyclyl, arylalkyl, heteroarylalkyl;
$R_7$, $R_{11}$, and $R_{12}$ are independently selected from H or —$C_1$-$C_8$ alkyl;
$R_9$ and $R_{10}$ are independently selected from H, —OH, —$C_1$-$C_8$ alkyl, or —O—($C_1$-$C_8$ alkyl);
$R_{13}$ and $R_{14}$ are independently selected from H, —OH, —$OR_{16}$, —$C_1$-$C_8$ alkyl, aryl, heterocyclyl, arylalkyl, heteroarylalkyl;
$R_{16}$ is selected from H or —$C_1$-$C_8$ alkyl;
p is an integer ranging from 1 to 8;
$R_{15}$ is selected from —$C_3$-$C_8$ alkyl, aryl, —$C_3$-$C_8$ heterocyclyl, —COOH, or —C(=O)$NR_{17}R_{18}$;
$R_{17}$ and $R_{18}$ are independently selected from H, —$C_1$-$C_8$ alkyl, —OH, —$OR_{19}$, or $R_{17}$ and $R_{18}$ together form a cycle of the formula —$(CR_{20}R_{21})_o$—Z—$(CR_{22}R_{23})_q$—, wherein $R_{19}$, $R_{20}$, $R_{21}$, $R_{22}$ and $R_{23}$ are independently selected from H, —$C_1$-$C_8$ alkyl, aryl, heterocyclyl, arylalkyl, heteroarylalkyl; Z is selected from O, $NR_{24}$, or $CR_{25}R_{26}$, wherein $R_{24}$, $R_{25}$ and $R_{26}$ are independently selected from H, or —$C_1$-$C_8$ alkyl; o and q are integers independently selected from 0 to 8.

In a preferred embodiment, the invention provides compounds of the formula IV:

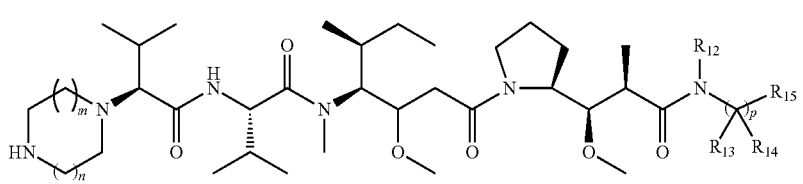

IV wherein
n and m are integers independently selected from 2 to 4, including 2, 3 and 4;
$R_{12}$ is selected from H or —$C_1$-$C_8$ alkyl;
$R_{13}$ and $R_{14}$ are independently selected from H, —OH, —$OR_{16}$, —$C_1$-$C_8$ alkyl, aryl, heterocyclyl, arylalkyl, or heteroarylalkyl;
$R_{16}$ is selected from H or —$C_1$-$C_8$ alkyl;
p is an integer ranging from 1 to 8, including 1, 2, 3, 4, 5, 6, 7 and 8;
$R_{15}$ is selected from —$C_3$-$C_8$ alkyl, aryl, —$C_3$-$C_8$ heterocyclyl, —COOH, or —C(=O)$NR_{17}R_{18}$;

$R_{17}$ and $R_{18}$ are independently selected from H, —$C_1$-$C_8$ alkyl, —OH, —$OR_8$, or $R_{17}$ and $R_{18}$ together form a cycle of the formula —$(CR_{20}R_{21})_o$—Z—$(CR_{22}R_{23})_q$—, wherein $R_{19}$, $R_{20}$, $R_{21}$, $R_{22}$ and $R_{23}$ are independently selected from H, —$C_1$-$C_8$ alkyl, aryl, heterocyclyl, arylalkyl, or heteroarylalkyl; Z is selected from O, $NR_{24}$, or $CR_{25}R_{26}$, wherein $R_{24}$, $R_{25}$ and $R_{26}$ are independently selected from H, or —$C_1$-$C_8$ alkyl; o and q are integers independently selected from 0 to 8, including 1, 2, 3, 4, 5, 6, 7 and 8.

In a preferred embodiment, the invention provides compounds 17-18 as shown below.

| Compound | Number |
|---|---|
| [chemical structure] | 17 |
| [chemical structure] | 18 |

In a preferred embodiment, the invention provides compounds 19-21 as shown below.

| Compound Structure | Number |
|---|---|
| [chemical structure] | 19 |
| [chemical structure] | 20 |
| [chemical structure] | 21 |

In a preferred embodiment, the invention provides compounds 22-45 as shown below.
| Compound | Number |
|---|---|
| 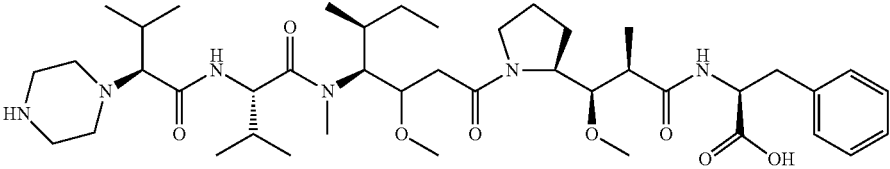 [SMILES: CC[C@H](C)[C@@H](C(CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N1CCNCC1)C(C)C] | 22 |
| 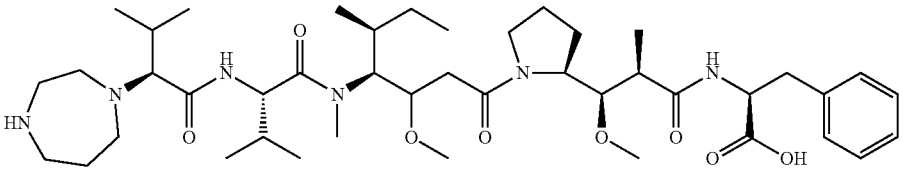 [SMILES: CC[C@H](C)[C@@H](C(CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N1CCCNCC1)C(C)C] | 23 |
| 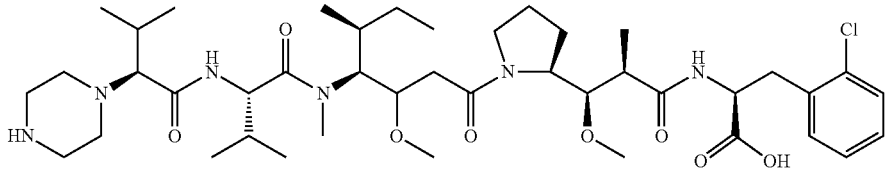 [SMILES: CC[C@H](C)[C@@H](C(CC(=O)N1CCC[C@H]1[C@H](OC)[C@@H](C)C(=O)N[C@@H](Cc1ccccc1Cl)C(=O)O)OC)N(C)C(=O)[C@@H](NC(=O)[C@H](C(C)C)N1CCNCC1)C(C)C] | 24 |
| 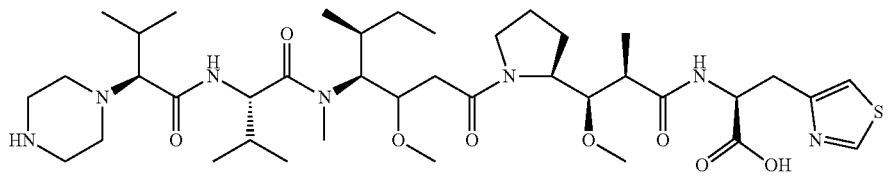 [SMILES: CC[C@H](C)[C@@H](C(CC(=O)N1CCC[C@H]1[C@H](OC)[C@@H](C)C(=O)N[C@@H](Cc1cscn1)C(=O)O)OC)N(C)C(=O)[C@@H](NC(=O)[C@H](C(C)C)N1CCNCC1)C(C)C] | 25 |
| 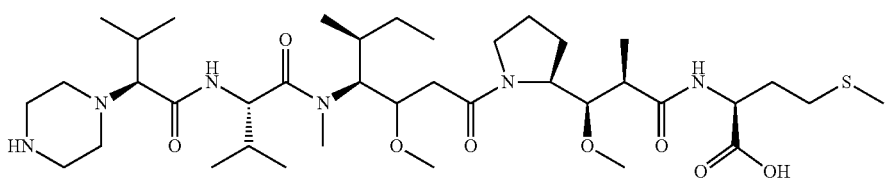 [SMILES: CC[C@H](C)[C@@H](C(CC(=O)N1CCC[C@H]1[C@H](OC)[C@@H](C)C(=O)N[C@@H](CCSC)C(=O)O)OC)N(C)C(=O)[C@@H](NC(=O)[C@H](C(C)C)N1CCNCC1)C(C)C] | 26 |
| 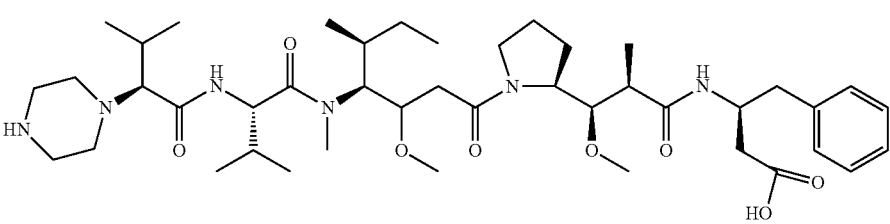 [SMILES: CC[C@H](C)[C@@H](C(CC(=O)N1CCC[C@H]1[C@H](OC)[C@@H](C)C(=O)N[C@H](CC(=O)O)Cc1ccccc1)OC)N(C)C(=O)[C@@H](NC(=O)[C@H](C(C)C)N1CCNCC1)C(C)C] | 27 |
| 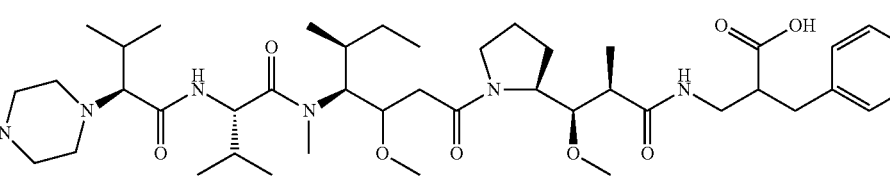 | 28 |
| 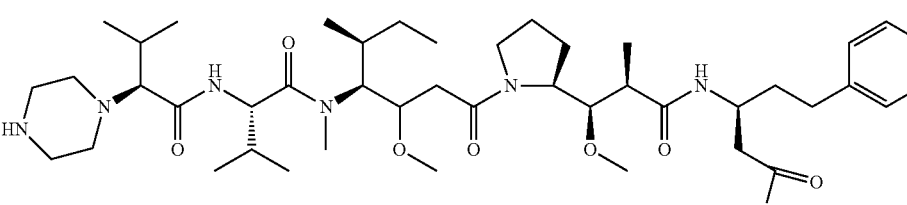 | 29 |

-continued
| Compound | Number |
|---|---|
| 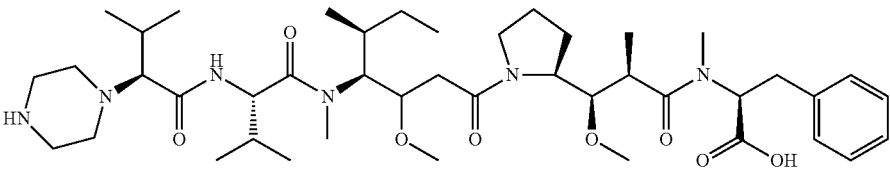 [SMILES: CC[C@H](C)[C@@H](C(CC(=O)N1CCC[C@H]1[C@H](OC)[C@@H](C)C(=O)N(C)[C@@H](Cc1ccccc1)C(=O)O)OC)N(C)C(=O)[C@@H](NC(=O)[C@H](C(C)C)N1CCNCC1)C(C)C] | 30 |
| 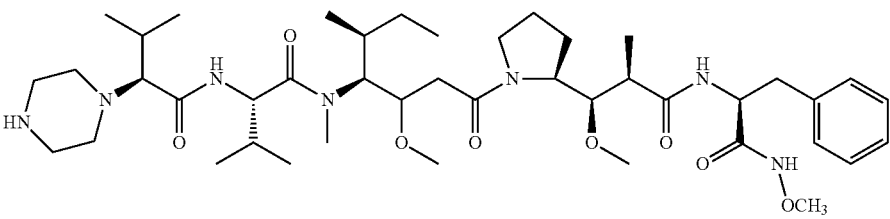 [SMILES: CC[C@H](C)[C@@H](C(CC(=O)N1CCC[C@H]1[C@H](OC)[C@@H](C)C(=O)N[C@@H](Cc1ccccc1)C(=O)NOC)OC)N(C)C(=O)[C@@H](NC(=O)[C@H](C(C)C)N1CCNCC1)C(C)C] | 31 |
| 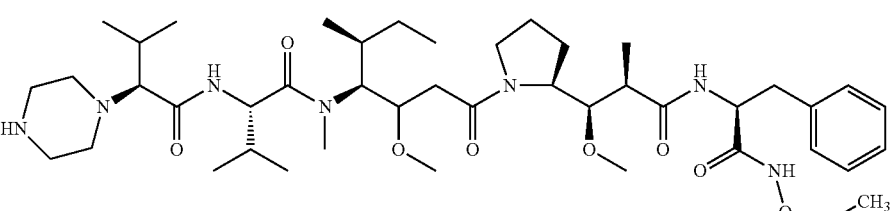 | 32 |
| 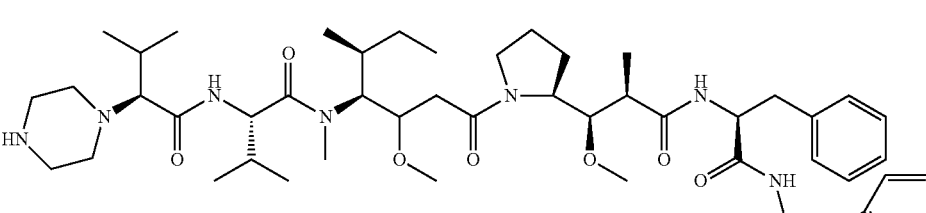 | 33 |
| 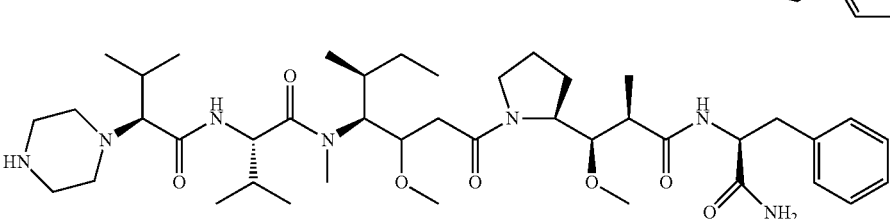 | 34 |
| 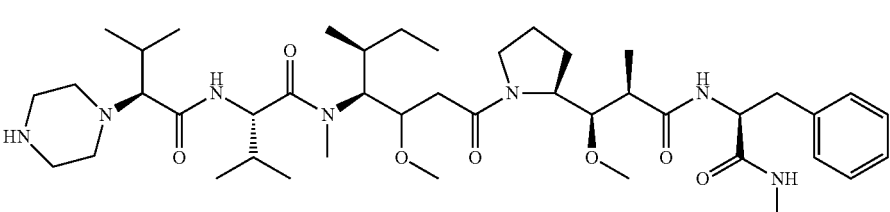 | 35 |
| 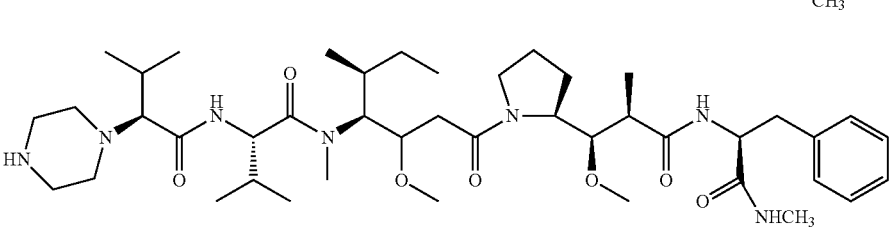 | 36 |

-continued
| Compound | Number |
|---|---|
| 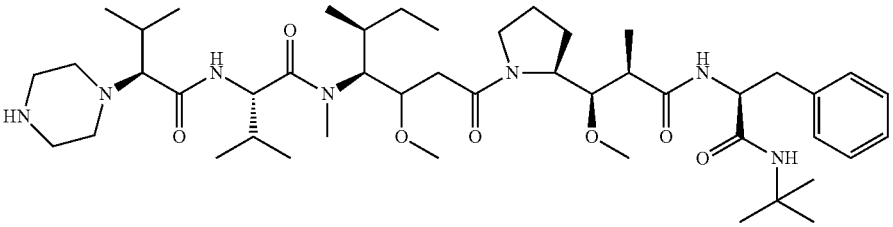 [SMILES: CC[C@H](C)[C@@H](C(CC(=O)N1CCC[C@H]1[C@H](OC)[C@@H](C)C(=O)N[C@@H](Cc1ccccc1)C(=O)NC(C)(C)C)OC)N(C)C(=O)[C@@H](NC(=O)[C@H](C(C)C)N1CCNCC1)C(C)C] | 37 |
| 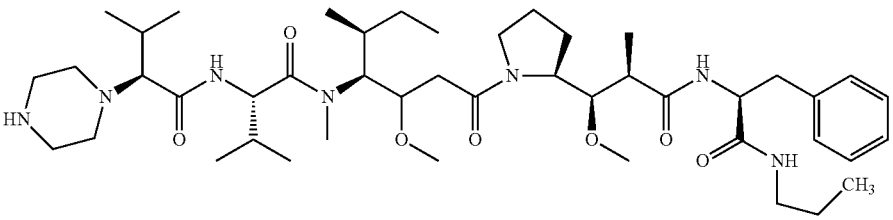 [SMILES: CCCNC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N1CCNCC1)C(C)C] | 38 |
| 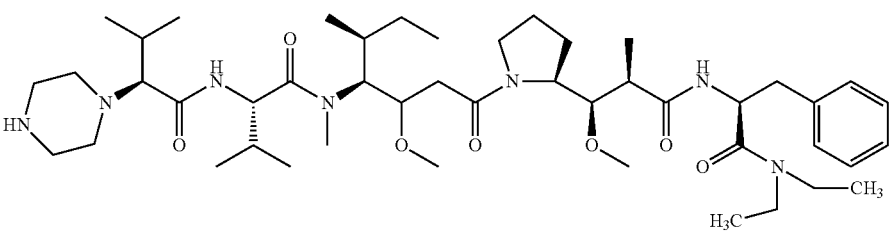 [SMILES: CC[C@H](C)[C@@H](C(CC(=O)N1CCC[C@H]1[C@H](OC)[C@@H](C)C(=O)N[C@@H](Cc1ccccc1)C(=O)N(CC)CC)OC)N(C)C(=O)[C@@H](NC(=O)[C@H](C(C)C)N1CCNCC1)C(C)C] | 39 |
| 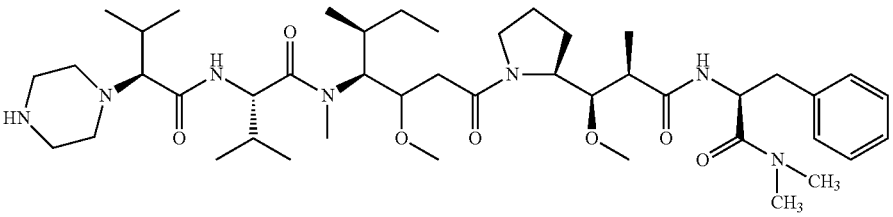 [SMILES: CC[C@H](C)[C@@H](C(CC(=O)N1CCC[C@H]1[C@H](OC)[C@@H](C)C(=O)N[C@@H](Cc1ccccc1)C(=O)N(C)C)OC)N(C)C(=O)[C@@H](NC(=O)[C@H](C(C)C)N1CCNCC1)C(C)C] | 40 |
| 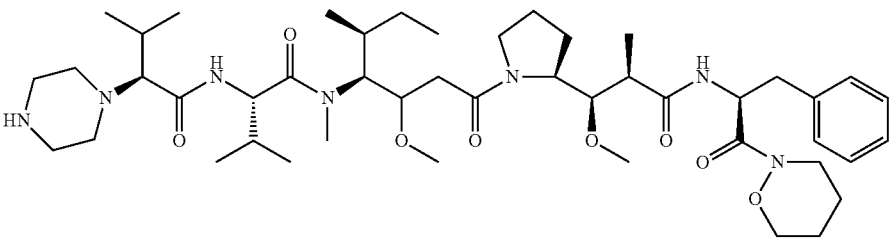 [SMILES: CC[C@H](C)[C@@H](C(CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N1CCNCC1)C(C)C] | 41 |
| 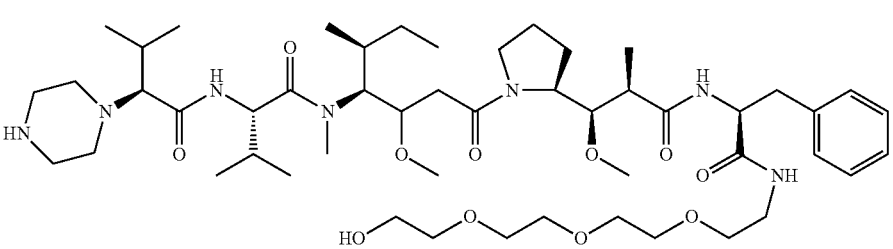 [SMILES: CC[C@H](C)[C@@H](C(CC(=O)N1CCC[C@H]1[C@H](OC)[C@@H](C)C(=O)N[C@@H](Cc1ccccc1)C(=O)NCCOCCOCCOCCO)OC)N(C)C(=O)[C@@H](NC(=O)[C@H](C(C)C)N1CCNCC1)C(C)C] | 42 |

-continued

| Compound | Number |
|---|---|
| 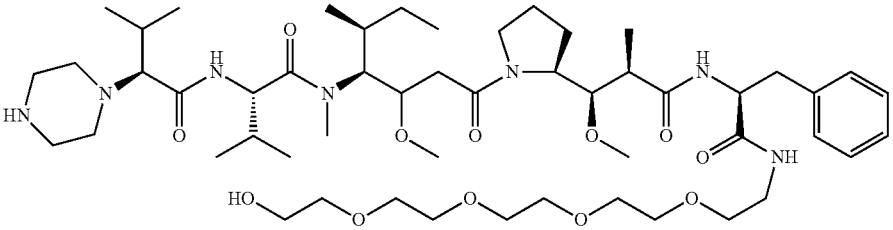 [SMILES: CC[C@H](C)[C@@H](C(CC(=O)N1CCC[C@H]1[C@H](OC)[C@@H](C)C(=O)N[C@@H](Cc1ccccc1)C(=O)NCCOCCOCCOCCOCCO)OC)N(C)C(=O)[C@@H](NC(=O)[C@H](C(C)C)N1CCNCC1)C(C)C] | 43 |
| 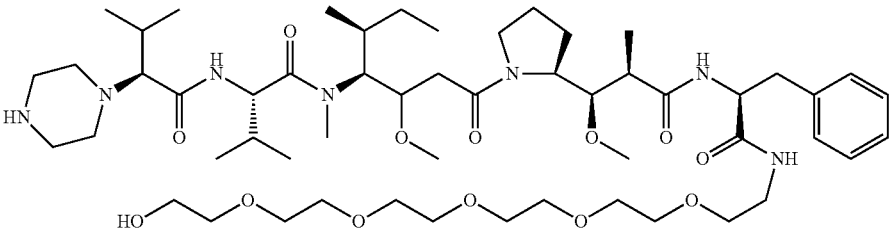 [SMILES: CC[C@H](C)[C@@H](C(CC(=O)N1CCC[C@H]1[C@H](OC)[C@@H](C)C(=O)N[C@@H](Cc1ccccc1)C(=O)NCCOCCOCCOCCOCCOCCO)OC)N(C)C(=O)[C@@H](NC(=O)[C@H](C(C)C)N1CCNCC1)C(C)C] | 44 |
| 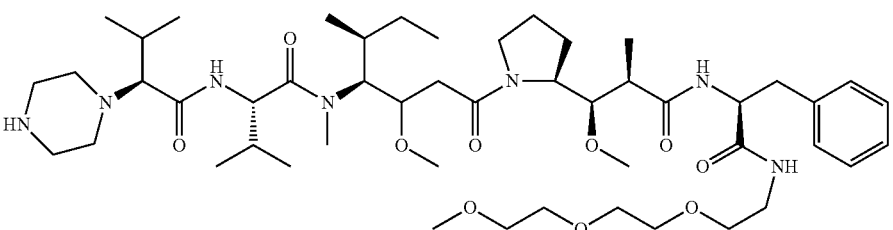 | 45 |

In the third aspect, the invention provides pharmaceutically acceptable salts, solvates, or solvates of salts, of the compounds shown above.

In the fourth aspect, the invention provides pharmaceutical compositions comprising the compounds provided by the invention, or pharmaceutically acceptable salts, solvates, or solvates of salts thereof, and pharmaceutically acceptable carriers.

In the fifth aspect, the invention provides ADCs of the formula V $$L\text{-}(A\text{-}D)_n \quad\quad V$$

wherein: L is an antibody, antibody fragment, or protein; A is a linker part; D is an above mentioned compound provided by the invention; n is an integer ranging from 1-8, including 1, 2, 3, 4, 5, 6, 7, and 8.

In the sixth aspect, the invention provides the use of the ADCs provided by the invention in the area of cancer, autoimmune, and inflammation diseases.

As a result, the invention provides novel high-potency cytotoxic drugs.

DETAILED DESCRIPTION OF THE INVENTION

Based on current auristatin type cytotoxic compounds (AE, MMAE, and MMAF, etc), the inventor obtained novel high-potency cytotoxic agents via structural modification on N- and C-terminals, and thus completed the invention.

Due to charged, cytotoxic compounds with carboxyl groups can hardly pass through the cell membrane in in vitro assays, which causes the inaccuracy of the measured cytotoxicity of this type of compounds and incomparability of these data with those of uncharged cytotoxic compounds. For this reason, the cytotoxicity of the compounds in the invention was determined by in vitro cell proliferation assay of the ADCs based on these compounds (the same antibody, such as antibody H; the same cleavable linker, such as vc linker) to compare their cytotoxicity indirectly. Furthermore, the inventor also measured the cytotoxicity of the ADCs with noncleavable linker (such as MC linker)

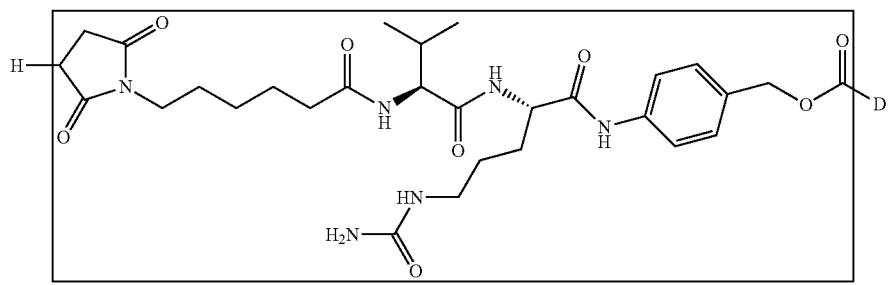

H-vc-D

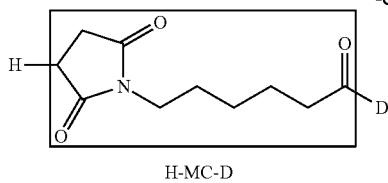

H-MC-D

ADC: H-vc-D, H-MC-D

Abbreviation

Ab antibody
Ac acetyl
ACN acetonitrile
BOC (Boc) tert-butylcarbonyl
BrOP bromotris(dimethylamino)phosphonium hexafluorophosphate
Bu butyl
t-Bu tert-butyl
° C. Celsius degree
DCM dichloromethane
DEA diethylamine
DEPC diethyl cyanophosphonate
DIEA diisopropylethyl amine
DMF N,N-dimethylformamide
DTT dithiothreitol
Et ethyl
EtOAc ethyl acetate
Eq equivalent
Fmoc 9-fluorenylmethyloxycarbonyl
g gram
h hour
HATU o-(7-azabenzotriazol-1-yl)-N,N,N',N'-tetramethyluronium hexafluoride
HOBt 1-hydroxybenzotriazole
HOSu N-hydroxysuccinimide
HPLC high performance liquid chromatography
LC-MS liquid chromatography-mass spectrometry
Linker linker
Me methyl
MeOH methanol
mAb monoclonal antibody
min minute
mL milliliter
microliter
PE petroleum ether
prep-RP-HPLC preparative-reverse phase-high performance liquid chromatography
rt room temperature
$R_t$ retention time
TEA triethylamine
TFA trifluoroacetic acid
THF tetrahydrofuran
TLC thin layer chromatography
TsCl p-tolylsufonyl chloride

Definition

As used herein, term "Alkyl" refers to saturated hydrocarbon radical containing normal, secondary, tertiary or cyclic carbon atoms. For example, methyl (—$CH_3$), ethyl (—$CH_2CH_3$), 1-propyl (—$CH_2CH_2CH_3$), 2-propyl (isopropyl, —$CH(CH_3)_2$), and cyclohexyl (—$C_6H_{11}$), etc.

"Alkenyl" refers to unsaturated hydrocarbon radical containing normal, secondary, tertiary or cyclic carbon atoms with at least one carbon-carbon $sp^2$ double bond (C=C). For example, vinyl (—CH=$CH_2$) and allyl (—$CH_2$CH=$CH_2$), etc.

"Alkynyl" refers to unsaturated hydrocarbon radical containing normal, secondary, tertiary or cyclic carbon atoms with at least one carbon-carbon sp triple bond (C≡C). For example, ethynyl (—C≡CH) and propargyl (—$CH_2$C≡CH), etc.

"Aryl" refers to a monovalent aromatic hydrocarbon radical of 6-12 carbon atoms derived by the removal of one hydrogen atom from a single carbon atom of a parent aromatic ring system. For example, phenyl, naphthyl, anthracyl, and biphenyl, etc.

"Heteroaryl" refers to a monovalent aromatic radical derived by the substitution of one or more carbon atoms of a parent aryl radical by one or more hetero atoms selected from N, O, P and S. For example, pyridinyl, thiophenyl, and furanyl, etc.

"Heterocycle" refers to an aromatic or nonaromatic ring system derived by the substitution of one or more carbon atoms of a parent aromatic or nonaromatic ring system by one or more hetero atoms selected from N, O, P, and S. For example, pyridine, thiophene, furan, hexahydropyridine (piperidine), and tetrahydrofuran, etc.

"Heterocyclyl" refers to an aromatic or nonaromatic cyclic radical derived by the removal of one hydrogen atom from a single carbon or hetero atom of a parent heterocycle ring system. For example, pyridinyl, thiophenyl, furanyl, piperidinyl, and tetrohydrofuranyl, etc.

"Arylalkyl" refers to an acyclic alkyl radical in which one of the hydrogen atoms bonded to a carbon atom, typically a terminal or sp3 carbon atom, is replace with an aryl radical. For example, benzyl and 3-phenylpropyl, etc. The alkyl part can also include alkenyl or alkynyl.

"Heteroarylalkyl" refers to an acyclic alkyl radical in which one of the hydrogen atoms bonded to a carbon atom, typically a terminal or sp3 carbon atom, is replaced with a heteroaryl radical. For example, 2-pyridinylethyl and 3-furanylpropyl, etc. The alkyl part of "heteroarylalkyl" can also include alkenyl or alkynyl.

"Alkylene" refers to a saturated, branched or straight chain or cyclic hydrocarbon radical, having two monovalent radical centers derived by the removal of two hydrogen atoms from the same or two different carbon atoms of a parent alkane. For example, methylene (—$CH_2$—), 1,2-ethyl (—$CH_2CH_2$—), and 1,3-propyl (—$CH_2CH_2CH_2$—), etc.

"Alkenylene" refers to an unsaturated, branched or straight chain or cyclic hydrocarbon radical, having two monovalent radical centers derived by the removal of two hydrogen atoms from the same or two different carbon atoms of a parent alkene. For example, 1,2-ethylene (—CH=CH—) and 1,3-propylene (—$CH_2$CH=CH—), etc.

"Alkynlene" refers to an unsaturated, branched or straight chain or cyclic hydrocarbon radical, having two monovalent radical centers derived by the removal of two hydrogen atoms from two different carbon atoms of a parent alkyne. For example, acetylene (—C≡C—) and propargyl (—CH$_2$C≡C—), etc.

"Arylene" refers to aromatic hydrocarbon radical with 6-12 carbon atoms, having two monovalent radical centers derived by the removal of two hydrogen atoms from two different carbon atoms of a parent aromatic ring system. For example, 1,2-phenylene, 1,3-phenylene, and 1,4-phenylene, etc.

"Substituted alkyl", "substituted alkenyl", "substituted alkynyl", "substituted aryl", "substituted heteroaryl", "substituted heterocyclyl", "substituted arylalkyl", and "substituted heteroarylalkyl" refers to, respectively, a radical derived by replacing one or more hydrogen atoms in the corresponding "alkyl", "alkenyl", "alkynyl", "aryl", "heteroaryl", "heterocyclyl", "arylalkyl", and "heteroarylalkyl" radicals, with one or more substitution groups independently. The substitution groups include, but not limited to, —X, —OR, —NR$_2$, —NO$_2$, —CN, —SO$_3$R, and —CO$_2$R, etc. wherein X is halogen atom, R is H, alkyl, aryl, heterocyclyl, protecting group or prodrug. The above-mentioned "alkylene", "alkenylene", and "alkynlene" can also be substituted in a similar way.

"Any combination thereof" refers to a new substitution group derived by connecting two or more radicals in a certain way. For example, benzyl (phenyl+methylene), 3-phenylpropyl (phenyl+1,3-propyl), 2-cyclohexylpropyl (cyclohexyl+1,2-propyl), and 3-(3-pyridinyl)propyl (3-pyridinyl+1,3-propyl), etc.

As used herein, the term "pharmaceutically acceptable salt" refers to pharmaceutically acceptable organic or inorganic salts of an exemplary compound. The exemplary compound contains at least one amino group to form acid addition salt. Exemplary salts include, but are not limited to, chloride, oxalate, citrate, sulfate, etc. A pharmaceutically acceptable salt may have one or more charged atoms in its structure, and thus may have one or more counter ions, which may be any organic or inorganic moiety that stabilizes the charge on the parent compound.

"Pharmaceutically acceptable solvate" or "solvate" refers to an association of one or more solvent molecules and a compound of the invention. Examples of solvents that form pharmaceutically acceptable solvates include, but are not limited to, water, ethanol, isopropanol, and acetic acid, etc.

"Pharmaceutically acceptable carrier" refers to a carrier for drug delivery, including excipient, diluent, etc. The term refers to the drug carrier that is not active ingredient in itself and not excessively toxic after use. Suitable carrier is well known for the skilled person in the art. Further discussions on pharmaceutically acceptable excipient can be found in Remington's Pharmaceutical Sciences (Mack Pub. Co., N.J. 1991).

As used herein, the term "antibody" or "antibody unit" includes within its scope any unit of an antibody that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified.

Antibody comprising the ADCs of the invention preferably retains the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antibody of the invention is capable of binding may be a member of a subset of one of the above-mentioned categories, wherein the other subset(s) of said category comprise other molecules/antigens that have a distinct characteristic (with respect to the antigen of interest).

Antibodies used in ADCs include, but not limited to, antibodies against cell surface receptors and tumor-associated antigens (TAA). Such tumor-associated antigens are well known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, Tumor-Associated Antigens (1)-(36) listed below. For convenience, information relating to these antigens, all of which are known in the art, is listed below and includes names, alternative names, Genbank accession numbers. Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references.

Tumor-Associated Antigens (1)-(36):
(1) BMPR1B (bone morephogenetic protein receptor-type IB, Genbank accession no. NM_001203);
(2) E16 (LAT1, SLC7A5, Genbank accession no. NM_003486);
(3) STEAP1 (six transmembrane epithelial antigen of prostate, Genbank accession no. NM_012449);
(4) 0772P (CA125, MUC16, Genbank accession no. AF361486);
(5) MPF (MPF, MSLN, SMR, megakaryocyte potentiating factor, mesothelin, Genbank accession no. NM_005823);
(6) Napi3b (NAPI-3B, NPTIIb, SLC34A2, solute carrier family 34 (sodium phosphate), member 2, type II sodium-dependent phosphate transporter 3b, Genbank accession no. NM_006424);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

(8) PSCA hlg (2700050C12Rik, C530008016Rik, RIKEN cDNA 2700050C12, RIKEN cDNA 2700050C12 gene, Genbank accession no. AY358628);

(9) ETBR (Endothelin type B receptor, Genbank accession no. AY275463);

(10) MSG783 (RNF124, hypothetical protein FLJ20315, Genbank accession no. NM_017763);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

(12) TrpM4 (BR22450, FLJ20041, TRPM4, TRPM4B, transient receptor potential cation channel, subfamily M, member 4, Genbank accession no. NM_017636);

(13) CRIPTO (CR, CR1, CRGF, CRIPTO, TDGF1, teratocarcinoma-derived growth factor, Genbank accession no. NP_003203 or NM_003212);

(14) CD21 (CR2 (Complement receptor 2) or C3DR (C3d/Epstein Barr virus receptor) or Hs. 73792, Genbank accession no. M26004);

(15) CD79b (CD79B, CD79β, IGb (immunoglobulin associated beta), B29, Genbank accession no. NM_000626);

(16) FcRH2 (IFGP4, IRTA4, SPAP1A (SH2 domain containing phosphatase anchor protein 1a), SPAP1B, SPAP1C, Genbank accession no. NM_030764);

(17) HER2 (ErbB2, Genbank accession no. M11730);

(18) NCA (CEACAM6, Genbank accession no. M18728);

(19) MDP (DPEP1, Genbank accession no. BC017023);

(20) IL20Rα (IL20Rα, ZCYTOR7, Genbank accession no. AF184971);

(21) Brevican (BCAN, BEHAB, Genbank accession no. AF229053);

(22) EphB2R (DRT, ERK, Hek5, EPHT3, Tyro5, Genbank accession no. NM_004442);

(23) ASLG659 (B7h, Genbank accession no. AX092328);

(24) PSCA (Prostate stem cell antigen precursor, Genbank accession no. AJ297436);

(25) GEDA (Genbank accession no. AY260763);

(26) BAFF-R (B-cell activating factor receptor, BLys receptor 3, BR3, Genbank accession no. AF116456);

(27) CD22 (B-cell receptor CD22-β form, Genbank accession no. AK026467);

(28) CD79a (CD79A, CD79α, immunoglobulin-associated alpha, a B-cell specific protein that covalently interacts with Ig beta (CD79B) and forms a complex on the surface with Ig M molecules, transduces a signal involved in B-cell differentiation, Genbank accession No. NP-001774.1);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);

(30) HLA-DOB (Beta subunit of MHC class II molecule (Ia antigen) that binds peptides and presents them to CD4+T lymphocytes, Genbank accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);

(32) CD72 (B-cell differentiation antigen CD72, Lyb-2, Genbank accession No. NP_001773.1);

(33) LY64 (lymphocyte antigen 64 (RP105), type I membrane protein of the leucine rich repeat (LRR) family, regulates B-cell activation and apoptosis, loss of function is associated with increased disease activity in patients with systemic lupus erythematosus, Genbank accession No. NP_005573.1);

(34) FcRH1 (Fc receptor-like protein 1, a putative receptor for the immunoglobulin Fc domain that contains C2 type Ig-like and ITAM domains, may have a role in B-lymphocyte differentiation, Genbank accession No. NP_443170.1);

(35) IRTA2 (Immunoglobulin superfamily receptor translocation associated 2, a putative immunoreceptor with possible roles in B cell development and lymphomagenesis; deregulation of the gene by translocation occurs in some B-cell malignancies, Genbank accession No. NP_112571.1); and

(36) TENB2 (putative transmembrane proteoglycan, related to the EGF/heregulin family of growth factors and follistatin, Genbank accession No. AF179274).

As used herein, the term "drug" or "D" refers to any compound possessing a desired biological activity and a reactive functional group that may be used to incorporate the drug into the conjugate of the invention. The desired biological activity includes the diagnosis, cure, mitigation, treatment, or prevention of diseases in man or other animals. Thus, so long as it has the needed reactive functional group, the term "drug" refers to chemicals recognized as drugs in the official Chinese National Pharmacopeia, official United States Pharmacopeia, official Homeopathic Pharmacopeia of the United States, or official National Formulary, or any supplement thereof. Exemplary drugs are set forth in the Physician's Desk Reference (PDR) and in the Orange Book maintained by the U.S. Food and Drug Administration (FDA). New drugs are continually being discovered and developed, and the present invention provides that these new drugs may also be incorporated into a prodrug form of the present invention.

In a preferred embodiment of the invention, the drug is: a cytotoxic drug useful in cancer therapy; a protein or polypeptide possessing a desired biological activity, such as a toxin, e.g., abrin, ricin A, *pseudomonas* exotoxin, and diphtheria toxin; other suitable proteins include tumor necrosis factor, α-interferon, β-interferon, nerve growth factor, platelet derived growth factor, tissue plasminogen activator, and biological response modifiers such as, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In one aspect, the drugs are maytansine or maytansinoids. Maytansine compounds inhibit cell proliferation by inhibiting the formation of microtubules of the microtubulin protein, tubulin (Science 1975, 189, 1002-1005; U.S. Pat. No. 5,208,020). Maytansinoids are derivatives of maytansine. Both maytansine and maytansinoids are highly cytotoxic, but their clinical use in cancer therapy has been greatly limited due to poor selectivity for tumors. However, the high cytotoxic potency enables them to be attractive drug moieties in ADCs. The structures shown below are maytansine, maytansinoids, and three representative maytansinoids mostly used in ADC drugs.

Maytansine

Maytansinoids

DM1

DM2

DM4

The key raw material for preparing maytansinoids is maytansinol, which is obtained from ansamitocins hydrolysis. Ansamitocins could be accessibly produced by fermentation. Ansamitocin derivatives (WO 2012/061590) and alaninyl maytansinol (US 2012/0121615) are also reported to be good candidates as ADC "warheads".

A is C=O, (C=O)NR', and (C=O)O
Y is a substituent group
Ansamitocin derivatives

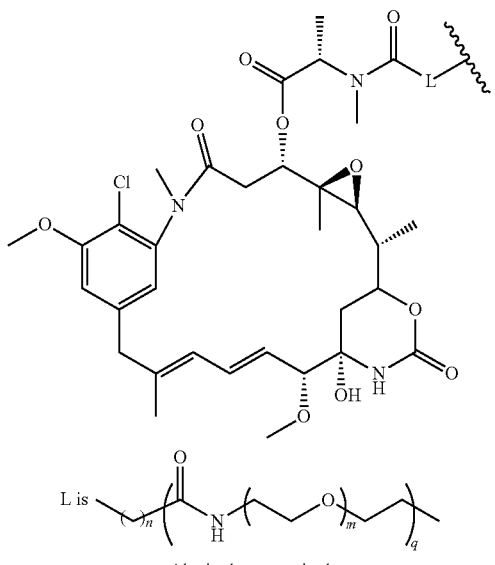

Alaninyl maytansinol

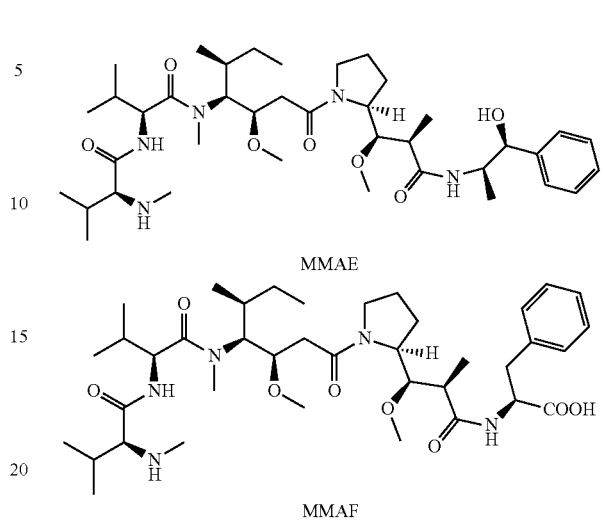

MMAE

MMAF

In one aspect, the drugs are auristatins. Auristatins are synthetic analogues of Dolastatin 10, which was isolated from the marine mollusk *Dolabella auricularia* and found to have biological activity (U.S. Pat. No. 7,498,298). Dolastatin 10 is an agent that inhibits tubulin polymerization by binding to the same domain on tubulin as the anticancer drug vincristine. Dolastitin 10, auristatin PE, and auristatin E are all linear peptides having four amino acids, three of which are unique to the dolastatin class of compounds, and a C-terminal amide. Two representative auristatins, monomethyl auristatin E (MMAE) and monomethyl auristatin F (MMAF), are preferred drug moiety candidates for ADCs.

The invention provides, preferably, auristatin derivatives of the formula I, II, III and IV, and more preferably, the compounds of the structure 1-45.

In one aspect, the drugs are tubulysins. Tubulysins are natural products first isolated from myxobacterial culture, which are potent cell growth inhibitor that act by inhibiting tubulin polymerization, and among which Tubulysin D is the most potent. Tubulysin D is a complex tetrapeptide, and labile in both acidic or basic conditions due to the o-acyl/N,O-acetal functionality within its structure. US 2011/0021568 and US 2013/0224228 disclosed a series of tubulysin analogs, which remove the labile groups and have high cytotoxic potency.

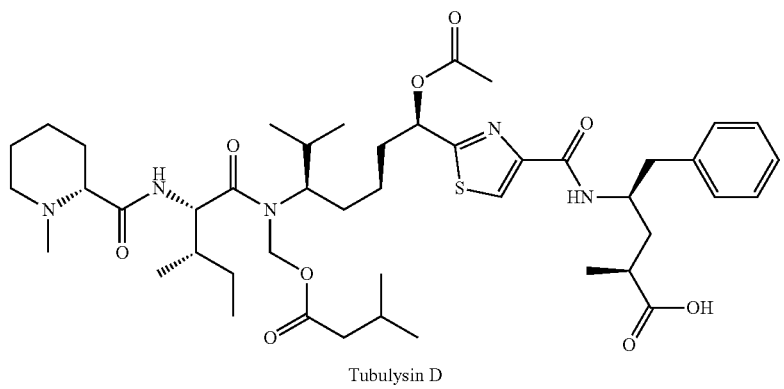

Tubulysin D

In one aspect, the drugs are calicheamicins. Calicheamicins are antitumor antibiotics that bind to the minor groove of DNA and produce site-specific double-strand DNA breaks, causing cell death. Calicheamicins are potent at sub-picomolar concentrations in vitro, but their low therapeutic index precluded further development clinically. The high potency, however, makes them good candidates for ADCs (such as Gemtuzumab Ozogamicin and Inotuzumab Ozogamicin).

are potent minor-groove binding DNA alkylating agents. Cyclopropabenzindol-4-one analogues (CBI) are chemically more stable, biologically more potent, and synthetically more accessible than their parent compounds incorporating the nature CPI alkylating subunit. One representative CBI derivative is the phenolic hydroxyl group-protected CBI (see the formula below), which has decreased prodrug toxicity and improved water solubility.

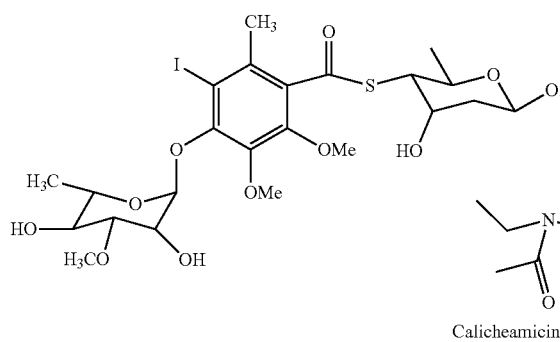

Calicheamicin

In one aspect, the drugs are doxorubicins. Doxorubicin is an intercalating agent that blocks DNA replication and is used as chemotherapeutic agent. Due to the relative low potency of doxorubicin ($IC_{50}$ of 0.1-0.2 µM for human carcinoma lines, whereas subnanomolar activities are now typically seen for ADC payloads), application of doxorubicin as ADC drug moiety is not popular.

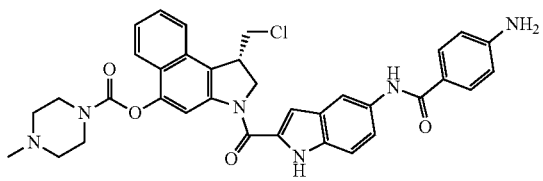

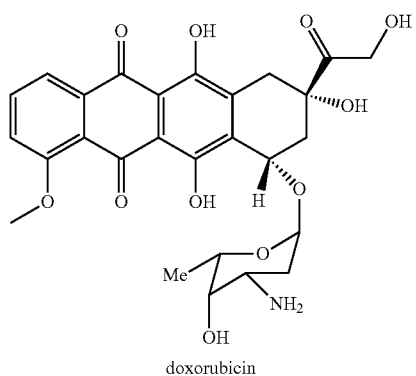 [SMILES: COc1cccc2c1C(=O)c1c(O)c3c(c(O)c1C2=O)C[C@@](O)(C(=O)CO)C[C@@H]3OC1CC(N)C(O)C(C)O1]

doxorubicin

In one aspect, the drugs are duocarmycins, CC-1065 and other cyclopropapyrroloind-4-one (CPI) derivatives, which In one aspect, the drugs are pyrrolo[2,1-c][1,4]benzodiazepines (PBDs) or PBD dimers. The pyrrolo[2,1-c][1,4] benzodiazepines (PBDs) are a family of natural products produced by *Streptomyces* species with the unique characteristic of forming nondistortive covalent adducts in the minor groove of DNA specifically at purine-guanine-purine sequences. There is growing interest in using PBDs as part of a small-molecule strategy for targeting DNA sequences and also as novel anticancer and antibacterial agents. (Biochemistry 2008, 47, 11818-11829). The biological activity of these molecules can be potentiated by joining two PBD units together through their C8/C8-hydroxyl functionalities via a flexible alkylene linker (WO 2011/130616). The PBD dimers are thought to form sequence-selective DNA lesions such as the palindromic 5'-Pu-GATC-Py-3' interstrand cross-link, which mainly accounts for their biological activity. These compounds have been shown to be highly useful cytotoxic agents and good candidates as ADC warheads.

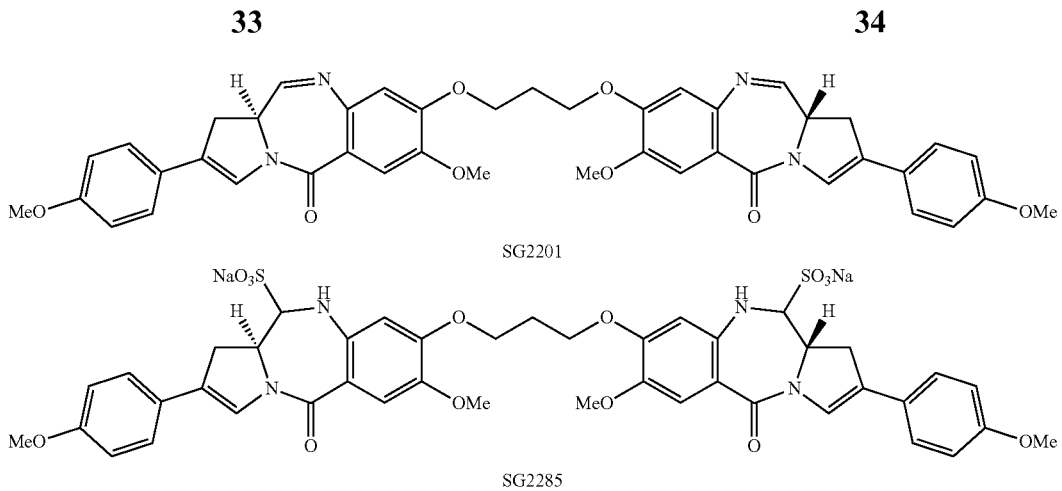

SG2201

SG2285

In another aspect, the drugs are not limited to above-mentioned categories and include all that could be used in ADCs.

As used herein, the term "linker" or "ADC linker" refers to a bifunctional or multifunctional molecular group that can react with a protein/antibody and a drug respectively, and thus link the protein/antibody to the drug as a "bridge". According to drug release mechanism in cells, linker or ADC linker could be classified into two categories: noncleavable linker and cleavable linker.

Noncleavable linker is a kind of relatively stable linker, which is difficult to decompose under in vivo conditions. For ADCs with noncleavable linkers, the release mechanism is believed to occur via internalization of the ADC followed by degradation of the mAb component in the lysosome, resulting in the release of the small molecular drug still attached via the linker to an antibody amino acid residue. The chemical modification of the drug didn't diminish its cytotoxic potential. This form of the drug is, however, charged (amino acid residue) and presumably hard to diffuse into neighboring cells. Hence, it can't kill adjacent tumor cells (bystander effects) that don't express the target antigen (antigen-negative cells) (Bioconjugate Chem. 2010, 21, 5-13). Examples of noncleavable linker include MC and MCC linker, as shown below.

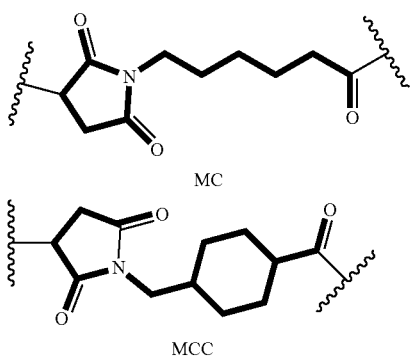

MC

MCC

Cleavable linkers, as the name implies, could be cleaved within the target cells that release the active drugs (small molecule drugs themselves). Cleavable linkers can be categorized into two main groups: chemically labile and enzyme-labile linkers.

Chemically labile linkers could be selectively cleaved upon the differential properties between the plasma and some cytoplasmic compartments. Such properties include pH value, glutathione concentration, etc.

For pH sensitive linkers, generally called acid-cleavable linker, the linkers are relatively stable in the blood's neutral environment (pH 7.3-7.5), but will undergo hydrolysis in the mildly acidic endosomes (pH 5.0-6.5) and lysosomes (pH 4.5-5.0). First generation of ADCs mostly used these kinds of linkers, such as hydrozones, carbonates, acetals, ketals, etc. However, due to the limited plasma stability of the acid-cleavable linkers, the ADCs based on these linkers have relatively short half-life (2-3 days). The low half-lives, to a certain degree, preclude the application of pH-sensitive linkers in the new generations of ADCs.

For glutathione-sensitive linkers, generally called disulfide linkers, the release is attributed to the high intracellular concentration of glutathione in the cytoplasma (millimolar range) compared to the relatively low concentration in the blood (micromolar range). This is especially true for tumor cells, where the hypoxic state results in enhanced activity of reductive enzymes and therefore even higher glutathione concentrations. Disulfide bonds are thermodynamically stable and thus provide good stability in plasma.

Enzyme-labile linkers are alternative approaches to achieve better control of the drug release, for example, peptide linkers. The peptide linkage will be effectively cleaved by lysosomal proteases, like cathepsin B or plasmin (elevated levels in certain tumor tissues). The peptidic linkages are deemed stable when circulating in plasma, as proteases are normally not active outside cells because of extracellular unfavorable pH and the serum protease inhibitors. Due to the high plasma stability and good intracellular cleaving selectivity and efficiency, enzyme-labile linkers are broadly selected as cleavable linker candidates in ADCs. Typical enzyme-labile linkers include Val-Cit (vc), etc.

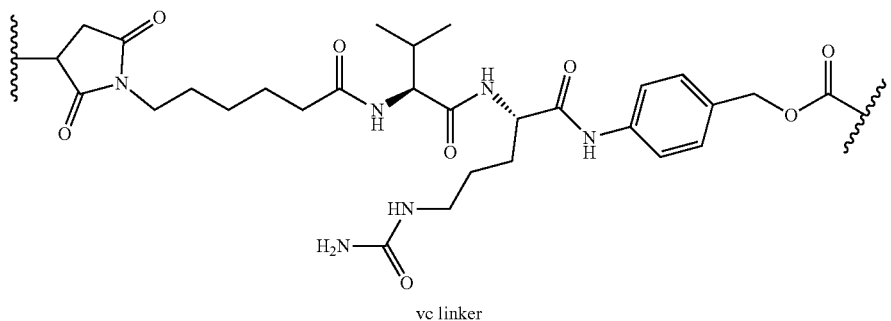 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

vc linker

Self-immolative linker is generally sited between cleavable linker and cytotoxic drug, or itself is part of cleavable linker. The working mechanism of self-immolative linker is that it can undergo self-structural rearrangement to release the active drug when the cleavable linker was cut by protease. Typical self-immolative linkers include p-aminobenzyl alcohol (PAB), etc.

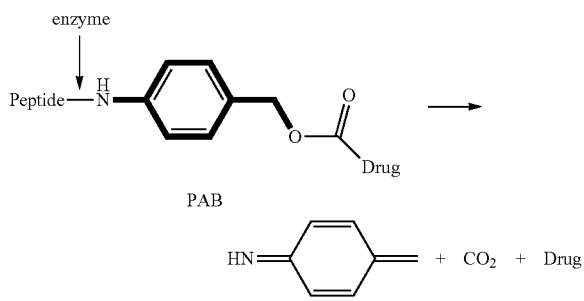

Antibody-Drug Conjugates

The antibody-drug conjugates provided in the invention are composed of antibody, linker, and drug. The linker includes cleavable linker or non-cleavable linker.

Use

The invention provides high-potency cytotoxic drugs, which can be widely used in ADC area as high-potency "bio warhead".

Based on the cytotoxic drugs disclosed herein, the present invention provides ADCs that target a special cell population and bind to specific cell surface proteins (antigens), followed by the internalization of the complexes into the cell and the drug release within the cell in active forms.

Based on the cytotoxic drugs disclosed herein, the present invention provides ADCs that target a special cell population, bind to the specific cell surface proteins (antigens), and take effects; or release drugs outside the cell, followed by the diffusion of the drugs into the cell to take effects.

The present invention provides compositions comprising an effective amount of a drug conjugate and a pharmaceutically acceptable carrier or vehicle.

The present invention provides methods for treatment of cancers or other tumors in animal subjects. The methods are to provide an effective amount of the ADCs provided by the invention to an animal subject with cancers or other tumors.

The present invention provides methods for treatment of autoimmune diseases or infectious diseases. The methods are to provide an effective amount of the ADCs provided by the invention to an animal subject with autoimmune diseases or infectious diseases.

The above features provided by the present invention, or features provided by examples, can be combined at will. All features provided by the present invention can be applied together with any combination, and each feature can be substituted by any identical, equal, or similar feature. Except for special illustration, all disclosed features are only general examples of the equal or similar features.

The present invention is further elaborated by examples. It should be understood that these examples are used to illustrate the present invention, while not limit its scope. The unstated experiment conditions are generally according to routine conditions or conditions suggested by manufacturers. Unless otherwise stated, all reactions were conducted under the protection of nitrogen (except hydrogenation reaction), which was not repeatedly described in example.

Unless otherwise defined, all professional and scientific terms used in the present invention have the same meaning as those familiar by the expertise in the art. Furthermore, any method or material similar or equal to those used in the present invention can be applied herein. The optimized methods and materials used in the present invention are only used for illustration while not for limitation.

General Procedures Used in the Invention

General Procedure A: Amide Formation Via Coupling Reagent DEPC

Proper amounts of carboxylic acid and amine (1-2 eq) were dissolved in DCM, to which DIEA/TEA (2-5 eq) and DEPC (1-2 eq) were added sequentially. The reaction mixture was stirred at rt until the reaction was complete (detected by TLC or LC-MS). The mixture was concentrated to remove the solvent, and the residue was purified by column chromatography or prep-RP-HPLC to give the target compound.

General Procedure B: Amide Formation Via Coupling Reagent HATU

Proper amount of carboxylic acid and amine (1-2 eq) were dissolved in DCM, to which DIEA/TEA (2-5 eq) and HATU (1-2 eq) were added sequentially. The reaction mixture was stirred at rt until the reaction was complete (detected by TLC or LC-MS). The mixture was concentrated to remove the solvent, and the residue was purified by column chromatography or prep-RP-HPLC to give the target compound.

General Procedure C: Deprotection of Boc-Protected Amine

Boc-protected amine compound was dissolved in a mixed solvent of TFA/DCM (v/v 1:1 or other ratio), and the reaction mixture was stirred at rt until the reaction was complete (detected by TLC or LC-MS). The reaction mixture was concentrated to remove the solvent, and the obtained target compound (TFA salt) could be used directly for next step. Or the TFA salt could be neutralized by sodium bicarbonate solution, and then the aqueous phase was extracted by organic solvent. The organic phase was washed with water, dried, and concentrated to give the crude product, which was further purified by column chromatography or prep-RP-HPLC to give the target compound.

General Procedure D: Deprotection of Fmoc-Protected Amine

Fmoc-protected amine compound was dissolved in a mixed solvent of DEA/DCM (v/v 1:2 or other ratio), and the reaction mixture was stirred at rt until the reaction was complete (detected by TLC or LC-MS). The reaction mixture was concentrated to remove the solvent, and the residue was purified by column chromatography or prep-RP-HPLC to give the target compound.

General Procedure E: Formation of Amino Acid/Carboxylic Acid Tert-Butyl Esters

A solution of amino acid/carboxylic acid in tert-butyl acetate was cooled to 0° C., to which perchloric acid (1.5 eq) was added slowly. The reaction mixture was stirred at rt until the reaction was complete (detected by TLC or LC-MS). The reaction mixture was washed sequentially with water and hydrochloric acid (1.0 M), and then potassium carbonate was added to the combined aqueous phase to adjust pH-9. The aqueous phase was then extracted by DCM several times. The combined organic phase was washed with water, dried, and concentrated. The residue was purified by column chromatography or prep-RP-HPLC to give the target compound.

General Procedure F: Deprotection of Tert-Butyl Carboxylate

Tert-butyl carboxylate was dissolved in a mixed solvent of TFA/DCM (v/v 1:1 or other ratio), and the reaction mixture was stirred at rt until the reaction was complete (detected by TLC or LC-MS). The reaction mixture was concentrated to remove the solvent, and crude product could be used directly for next step, or could be purified by column chromatography or prep-RP-HPLC to give the target compound.

General Procedure G: Activation of Alcohol by Bis(p-Nitrophenyl) Carbonate

Proper amounts of alcohol, bis(p-nitrophenyl) carbonate (2 eq), and TEA/DIEA (3 eq) were added in DCM sequentially. The reaction mixture was stirred at rt (or certain temperature) for some time. If the alcohol was not totally consumed, more bis(p-nitrophenyl) carbonate and more time were required until the alcohol was completely consumed (detected by TLC or LC-MS). The reaction mixture was concentrated to remove the solvent, and the residue was purified by column chromatography or prep-RP-HPLC to give the target compound.

General Procedure H: Formation of Carbamate by the Reaction of Amine with p-Nitrophenyl Carbonate (Activated Alcohol)

Amine and p-nitrophenylcarbonate (activated alcohol from General Procedure G, 1-2 eq) were dissolved in DCM, and the reaction mixture was stirred at rt until the reaction was complete (detected by TLC or LC-MS). The reaction mixture was concentrated to remove the solvent, and the residue was purified by column chromatography or prep-RP-HPLC to give the target compound.

General Procedure I: Formation of Carbamate by the Reaction of Amine with p-Nitrophenyl Carbonate (Activated Alcohol)

Amine, p-nitrophenylcarbonate (activated alcohol from General Procedure G, 1-2 eq), and HOBt were dissolved in a mixed solvent of pyridine/DMF. The reaction mixture was stirred at rt until the reaction was complete (detected by TLC or LC-MS). The reaction mixture was concentrated to remove the solvent, and the residue was purified by column chromatography or prep-RP-HPLC to give the target compound.

General Procedure J: Preparation of ADC

DTT (1-100 eq, or preferably, 2.7 eq of which used for reduction of average two antibody interchain disulfide bonds to produce 4 (mean value) conjugatable cysteine thiol groups, 10 mM stock solution) was added to a solution of antibody (10 mg/mL, containing 25 mM boric acid-sodium borate buffer, 25 mM sodium chloride, and 1 mM DTPA, pH-8.0). The reaction mixture was incubated at 37° C. in a shaker for 2 h.

Reducing reagent was removed from the reaction mixture by ultrafiltration or desalting column, while the reduced antibody was buffer exchanged into PBS buffer (100 mM, containing 10 mM NaCl, 1 mM DTPA, pH-7.0).

DMSO and linker-drug (DMSO stock solution, 1-10 eq, or preferably, 8 eq) were added to the reduced antibody solution cooled to 10° C., keeping the volume percentage of DMSO at 15% or so. The conjugation reaction was conducted at 10° C. for 0.5 h.

Excess cysteine solution was added to the reaction mixture to quench the unreacted linker-drug. The quenching reaction was conducted at 10° C. for 30 min. Excess cysteine and cysteine-linker-drug adduct were removed by ultrafiltration or desalting column from the reaction mixture, and the ADC solution was sterile filtered through 0.2 μm filter, and kept at 4° C.

General Procedure K: Enzyme-Linked Immunosorbent Assay (ELISA)

Indirect ELISA was used to analyze binding ability of the antibody or antibody-drug conjugate to the corresponding antigen. The antigen was immobilized on a solid-phase support (96 well microplate) by coating to form a solid-phase antigen, and then unbound antigen was removed by washing. Serial dilutions of test antibody or antibody-drug conjugate were added, wherein specific antibody or antibody-drug conjugate bound to the antigen and formed solid-phase antigen-antibody complexes. The antibody or antibody-drug conjugate unbound to the solid-phase antigen was removed by washing. The enzyme labeled anti-antibody was added to bind to the above-formed complexes. After washing, substrate solution was added to develop color, and the optical density was read by a microplate reader at 450 nm/630 nm, based on which the curve was drawn and the $EC_{50}$ was calculated.

General Procedure L: Cell Proliferation Inhibition Assay

Generally, the cytotoxic activity of an antibody or antibody-drug conjugate is measured by the following: exposing mammalian cells having tumor-associated antigens or receptor proteins to the antibody or the ADC in a cell culture medium; culturing the cells for a period of 2 to 5 days; and measuring cell number, based on which the curve was drawn and the $IC_{50}$ was calculated.

Unless otherwise stated, all anhydrous solvents were purchased from the suppliers and kept under nitrogen. All other reagents and solvents were purchased at high purity and not purified before use.

$^1$H NMR spectrum was collected on a Bruker Avance III 500 MHz instrument. Chemical shift (δ) unit is ppm, and the reference reagent is TMS (δ=0). The coupling constant (J) unit is Hz.

For LC-MS, low resolution mass spectrum was collected on Agilent 6110 (acid method) or 6120B (base method) mass spectrometers coupled with Hewlette-Packard Agilent 1200 HPLC.

Method 1:

Waters Sunfire C18 reverse phase column (4.60×50 mm, 3.5 μm) was used in the acid HPLC method for separation, and the eluting gradient was 5%-95% B (acetonitrile, containing 0.01% TFA) in A (water, containing 0.01% TFA) in 1.4 min. The flow rate was 2.0 mL/min, and the column temperature was 50° C.

Method 2:

Waters Xbridge C18 reverse phase column (4.60×50 mm, 3.5 μm) was used in the base HPLC method for separation, and the eluting gradient was 5%-95% B (acetonitrile) in A (water, containing 10 mM ammonium bicarbonate) in 1.5 min. The flow rate was 2.0 mL/min, and the column temperature was 40° C.

Purification by prep-RP-HPLC was conducted on a Gilson instrument. Waters Sunfire C18 reverse phase column (250×19 mm, 10 μm) was used for separation.

Method 3:

The acid preparation method. Mobile phase: A: water phase containing 0.1% TFA; B: ACN; flow rate: 20 mL/min.

Method 4:

The base preparation method. Mobile phase: A: water phase containing 10 mM $NH_4HCO_3$; B: ACN; flow rate: 20 mL/min.

SK-BR-3 human breast cancer cell was purchased from ATCC. Her2 antigen was purchased from Sino Biological Inc (Beijing). Antibody H (Herceptin Biosimilar) was purchased from Genor Biopharma Co. Ltd. (Shanghai). The enzyme labeled anti-antibody was purchased from Sigma (Shanghai). Substrate solution was purchased from Decent Biotech (Shanghai). Cell Counting Kit (CCK-8) cell proliferation and cytotoxicity assay kit was purchased from Dojindo (Shanghai).

Key Intermediates (KIs)

The key intermediates used in the invention are shown as follows. Among them, AE, Fmoc-MMAE, MC, MC-Val-Cit-PABC-PNP, KI-1, KI-2, KI-3, KI-4, and KI-5 were synthesized according to literature methods (U.S. Pat. Nos. 5,635,483, 6,884,869, 7,498,298).

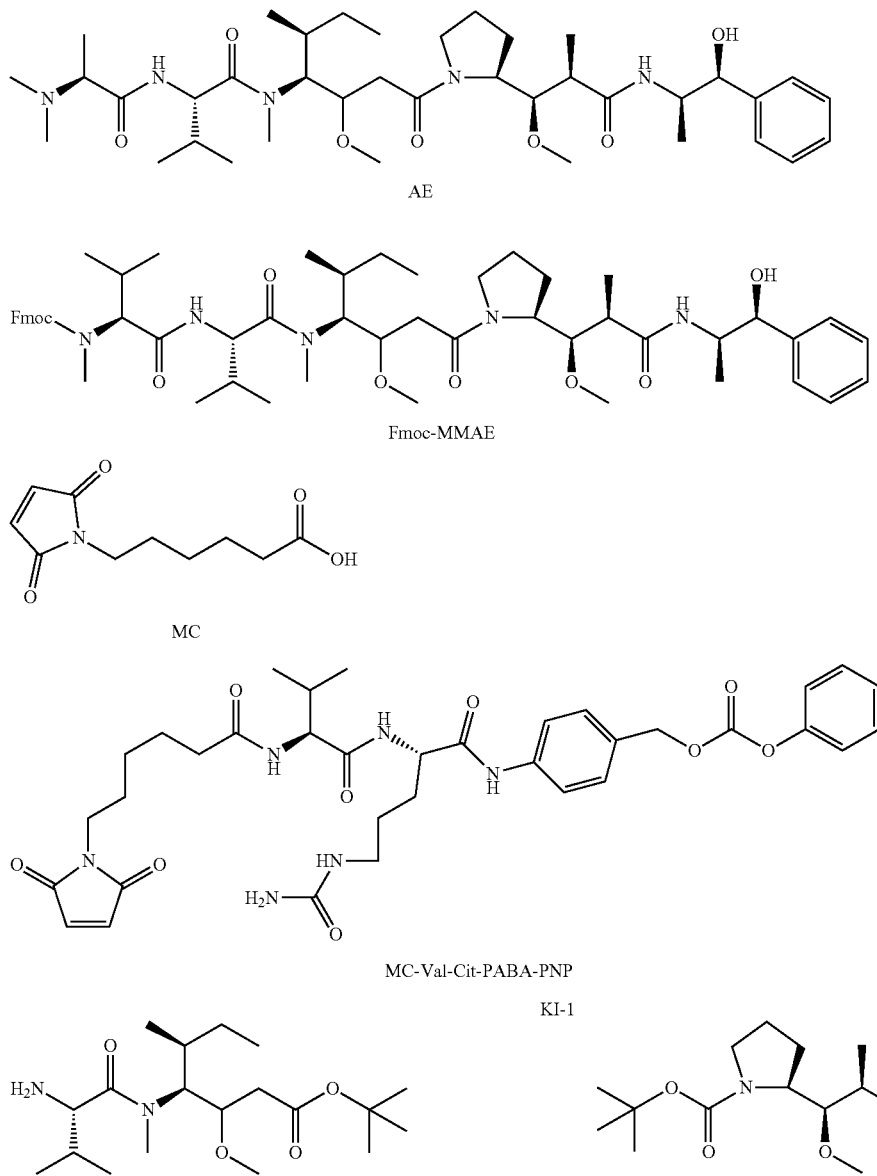

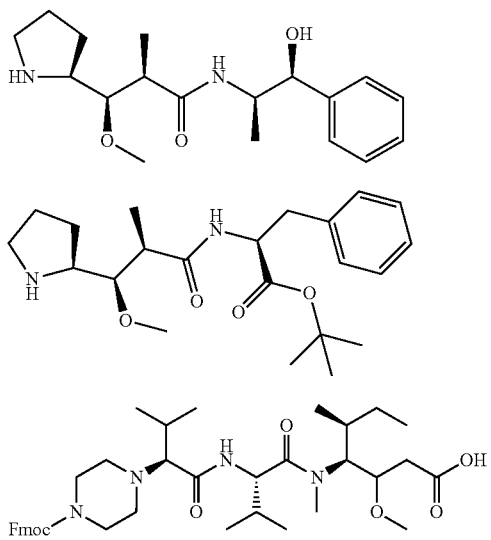
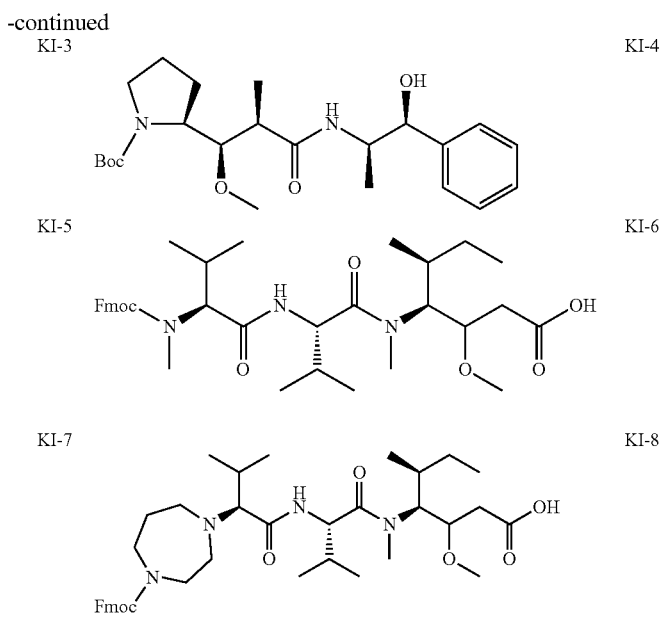

Synthesis of KI-7

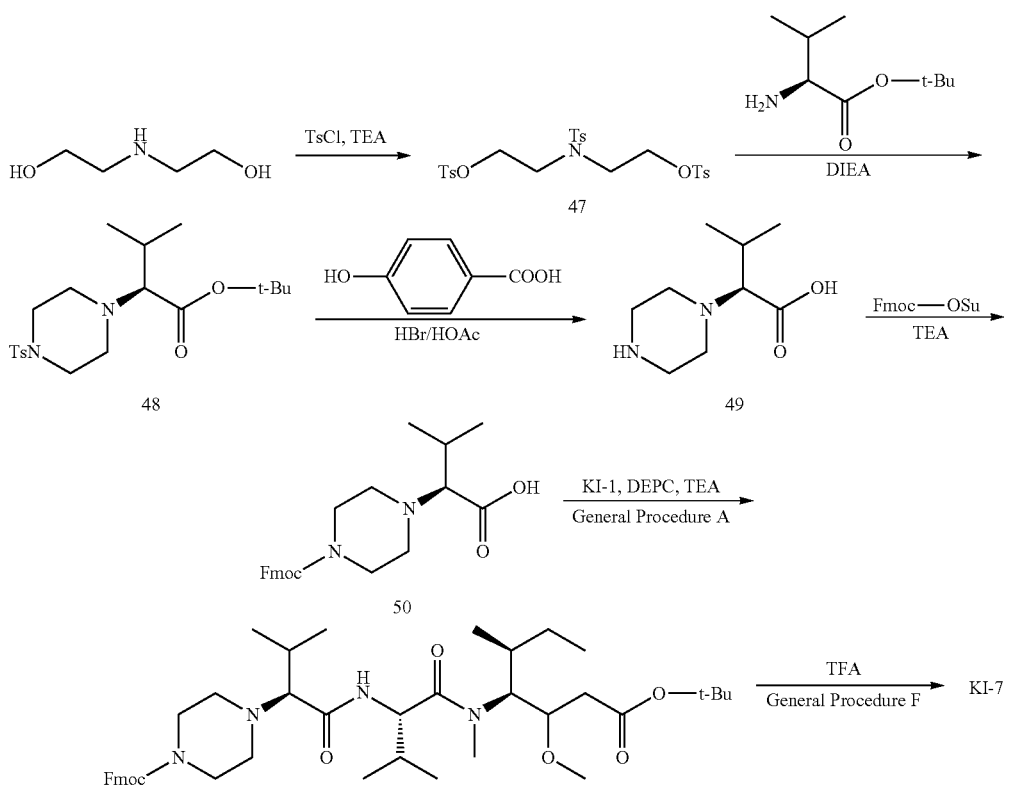

Step 1

Diethanolamine (4.0 g, 38.0 mmol) and TEA (19.2 g, 190 mmol) were dissolved in DCM (300 mL), to which TsCl (26.1 g, 137 mmol) was added slowly. The reaction mixture was stirred at rt for 18 h. The organic phase was washed sequentially with aqueous citric acid (10%), water, and brine, and then dried, filtered, and concentrated to give a white solid 47 (19.5 g), which was used directly for next step. LC-MS (Method 1): $R_t$=2.12 min; m/z (ES$^+$)=568.0 (M+H)$^+$.

Step 2

Compound 47 (2.0 g, 3.52 mmol) and L-valine tert-butyl ester (0.74 g, 3.52 mmol) were dissolved in DIEA (20 mL). The reaction mixture was vigoriously stirred at 127° C. for 18 h, and then concentrated to remove the solvent. Water (100 mL) was added to the residue, and the mixture was extracted with EtOAc (40 mL×3). The combined organic phase was washed with water, dried, and concentrated. The residue was purified by silica gel chromatography (PE/EtOAc 15:1) to give a pale yellow solid 48 (1.1 g). LC-MS (Method 2): $R_t$=2.45 min; m/z (ES$^+$)=397.3 (M+H)$^+$.

Step 3

Compound 48 (900 mg, 2.27 mmol) and p-hydroxybenzoic acid (1.04 g, 7.5 mmol) were added to a solution of HBr in acetic acid (33%, 3.9 mL). The reaction mixture was stirred at rt overnight. EtOAc (10 mL) was added to the mixture, which was stirred for another 5 min. The precipitate was collected by filtration, and washed with EtOAc (20 mL). The filter cake was dried to give a white solid 49 (500 mg), which was used directly for next step. LC-MS (Method 2): $R_t$=0.46 min; m/z (ES$^+$)=187.2 (M+H)$^+$.

Step 4

Compound 49 (500 mg, 2.69 mmol) was dissolved in a mixed solvent of 1,4-dioxane/water (v/v 3:1, 20 mL), to which sodium bicarbonate (1.35 g, 16.1 mmol) and Fmoc-Cl (829 mg, 3.22 mmol) were sequentially added. The reaction mixture was stirred at rt overnight. Citric acid solution (10% in water) was added to adjust the reaction mixture pH to 2-3, and then the solution was extracted with EtOAc (20 mL×3). The combined organic phase was washed with brine, dried, and concentrated. The residue was purified by silica gel chromatography (PE/EtOAc 3:1 to DCM/MeOH 15:1) to give the crude product, which was further purified by prep-RP-HPLC (Method 3: 35%-50% B in 8 min→95% B; $R_t$: 5.7-7.1 min) to give a white solid 50 (190 mg). LC-MS (Method 1): $R_t$=1.74 min; m/z (ES$^+$)=409.3 (M+H)$^+$. $^1$H NMR (500 MHz, CDCl3) δ7.75 (dd, 2H), 7.53 (d, 2H), 7.39 (d, 2H), 7.33 (d, 2H), 4.59 (d, 2H), 4.21 (t, 1H), 3.79-3.67 (m, 4H), 3.37-3.02 (m, 4H), 2.25 (m, 1H), 1.18 (d, 3H), 1.04 (d, 3H).

Step 5

Compound 50 (280 mg, 0.69 mmol) and KI-1 (245 mg, 0.69 mmol) were dissolved in DCM (6 mL), to which DIEA (265 mg, 2.06 mmol) and DEPC (168 mg, 1.03 mmol) were added sequentially. The reaction mixture was stirred at rt for 3 h, and then concentrated to remove the solvent. The residue was purified by silica gel chromatography (PE/EtOAc 4:1) to give colorless oil 51 (280 mg). LC-MS (Method 2): $R_t$=2.65 min; m/z (ES$^+$) N/A.

Step 6

Compound 51 (270 mg) was dissolved in DCM (3 mL), and the solution was cooled to 10° C., to which trifluoroacetic acid (3 mL) was added. The reaction mixture was stirred at 10° C. for 4 h. The mixture was concentrated to remove the solvent to give the crude product (260 mg), which was used directly for next step. LC-MS (Method 2): $R_t$=1.96 min; m/z (ES$^+$)=693.3 (M+H)$^+$.

Synthesis of KI-8 的合成

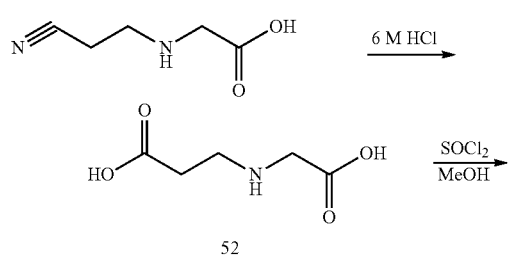

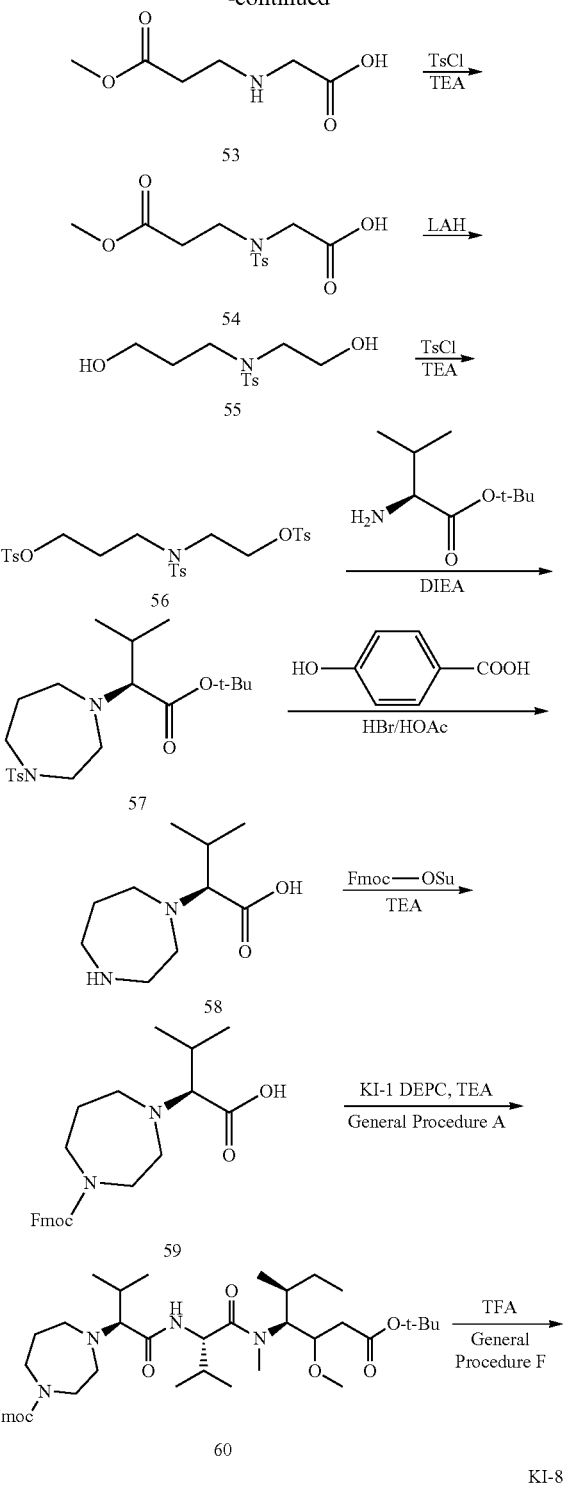

Step 1

N-(2-Cyanoethyl)glycine (6.5 g, 50.8 mmol) was added to 6M hydrochloric acid (50 mL), and the reaction mixture was stirred at 100° C. for 2 d. The mixture was concentrated to remove the solvent, and the crude product was dried in vacuo at 50° C. to give a white solid 52 (8.5 g). LC-MS (Method 1): $R_t$=0.19 min; m/z (ES$^+$)=148.1 (M+H)$^+$.

Step 2

Compound 52 (8.5 g) was dissolved in MeOH (100 mL), and the solution was cooled to 0° C. Sulfonyl chloride (13.63 g, 115.6 mmol) was added to the solution dropwise. The reaction mixture was refluxed for 2 h, and then concentrated to remove the solvent to give the crude product 53 (HCl salt, 12.5 g), which was used directly for next step. LC-MS (Method 1): $R_t$=0.34 min; m/z (ES$^+$)=176.1 (M+H)$^+$.

Step 3

Compound 53 (12.5 g) was suspended in DCM (300 mL), to which TEA (21.64 g, 214.3 mmol) and TsCl (17.7 g, 92.9 mmol) were added sequentially. The reaction mixture was stirred at rt for 18 h. The organic phase was washed sequentially with water and brine, dried, and concentrated. The residue was purified by silica gel chromatography (PE/EtOAc 4:1) to give colorless oil 54 (13.0 g). LC-MS (Method 1): $R_t$=1.48 min; m/z (ES$^+$)=330.0 (M+H)$^+$.

Step 4

Compound 54 (13.0 g) was dissolved in anhydrous THF (200 mL), and the solution was cooled to 0° C., to which lithium aluminum hydride (2.99 g, 78.9 mmol) was added portionwise in 50 min. The reaction mixture was stirred at 0° C. for 3 h, and then saturated ammonium chloride solution (3 mL) was added to quench the reaction. The mixture was concentrated to remove the solvent, and the residue was suspended in a mixed solvent of saturated ammonium chloride solution (150 mL) and isopropanol/chloroform (v/v 3:1, 150 mL). The mixture was filtered to remove the precipitate, and the separated aqueous phase from the filtrate was continually extracted with isopropanol/chloroform (v/v 3:1, 100 mL). The combined organic phase was dried and concentrated to give pale yellow oil 55 (11.5 g), which was used directly for next step. LC-MS (Method 2): $R_t$=1.61 min; m/z (ES$^+$)=274.2 (M+H)$^+$.

Step 5

Compound 55 (4.2 g) was suspended in DCM (100 mL), to which TEA (6.21 g, 61.5 mmol) and TsCl (7.04 g, 36.9 mmol) were sequentially added. The reaction mixture was stirred at rt overnight. The organic phase was washed sequentially with water and brine, dried, and concentrated. The residue was purified by silica gel chromatography (PE/EtOAc 4:1) to give pale yellow oil 56 (3.7 g). LC-MS (Method 2): $R_t$=2.27 min; m/z (ES$^+$)=599.2 (M+NH$_4$)$^+$.

Step 6

Compound 56 (3.7 g) and L-valine tert-butyl ester (1.33 g, 6.37 mmol) were added in DIEA (30 mL), and the reaction mixture was vigorously stirred at 127° C. for 18 h. The mixture was concentrated to remove the solvent, and water (50 mL) was added. The mixture was extracted with EtOAc (50 mL×3). The combined organic phase was washed with water, dried, and concentrated. The crude product was purified by silica gel chromatography (PE/EtOAc/DCM 15:1:1) to give pale yellow oil 57 (2.3 g), which was used directly for next step. LC-MS (Method 2): $R_t$=2.47 min; m/z (ES$^+$)=411.3 (M+H)$^+$.

Step 7

Compound 57 (2.8 g, 6.82 mmol) and p-hydroxybenzoic acid (3.1 g, 22.5 mmol) were added to a solution of hydrobromic acid (33% in acetic acid, 20 mL). The reaction mixture was stirred at rt for 24 h. EtOAc (200 mL) was added to the reaction mixture, and the mixture was stirred for 5 min. The precipitate was collected by filtration, and washed with EtOAc (50 mL). The filter cake was dried in vacuo to give a white solid 58 (HBr salt, 630 mg). LC-MS (Method 1): $R_t$=0.17 min; m/z (ES$^+$)=201.2 (M+H)$^+$.

Step 8

Compound 58 (630 mg, 3.15 mmol) was dissolved in THF/H$_2$O (v/v 5:1, 12 mL), to which sodium carbonate (0.26 g, 3.15 mmol), TEA (0.95 g, 9.45 mmol), and Fmoc-OSu (1.38 g, 4.09 mmol) were sequentially added. The reaction mixture was stirred at rt for 18 h, and then citric acid solution (10% in water) was added to adjust pH to 2-3. The mixture was extracted with EtOAc (20 mL×3), and the organic phase was washed with brine, dried, and concentrated. The crude product was purified by silica gel chromatography (DCM/MeOH 30:1) to give a white solid 59 (530 mg). LC-MS (Method 2): $R_t$=1.76 min; m/z (ES$^+$)=423.3 (M+H)$^+$. $^1$H NMR (500 MHz, CDCl$_3$) δ7.75 (d, 2H), 7.55 (d, 2H), 7.40 (m, 2H), 7.33 (m, 2H), 4.72-4.55 (m, 2H), 4.21 (m, 1H), 3.82-3.10 (m, 9H), 2.20-2.08 (m, 3H), 1.18 (t, 3H), 1.05-1.00 (dd, 3H).

Step 9

Compound 59 (400 mg, 0.95 mmol) and KI-1 (339 mg, 0.95 mmol) were dissolved in DCM (10 mL), to which TEA (287 mg, 2.8 mmol) and DEPC (200 mg, 1.23 mmol) were added sequentially. The reaction mixture was stirred at rt for 18 h, and then concentrated to remove the solvent. The residue was purified by silica gel chromatography (DCM/MeOH 40:1) to give a white solid 60 (610 mg). LC-MS (Method 1): $R_t$=1.77 min; m/z (ES$^+$)=763.3 (M+H)$^+$.

Step 10

Compound 60 (610 mg) was dissolved in DCM (3 mL), and the solution was cooled to 0° C., to which TFA (1.5 mL) was added. The reaction mixture was stirred at 10° C. for 4 h. The mixture was concentrated to remove the solvent to give the crude product, which was used directly for next step. LC-MS (Method 1): $R_t$=1.57 min; m/z (ES$^+$)=707.4 (M+H)$^+$.

Example 1

Synthesis of Compound 1

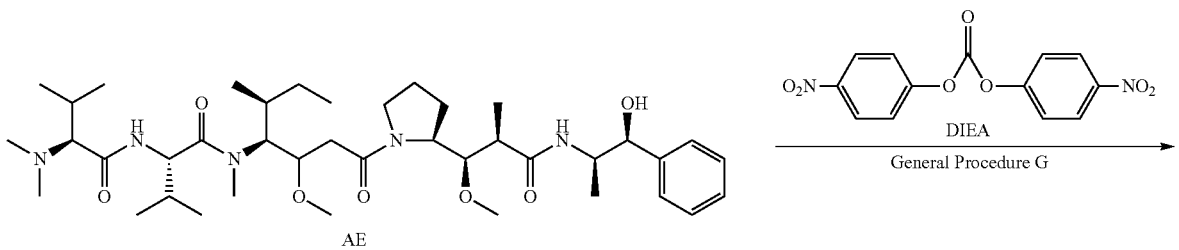

AE

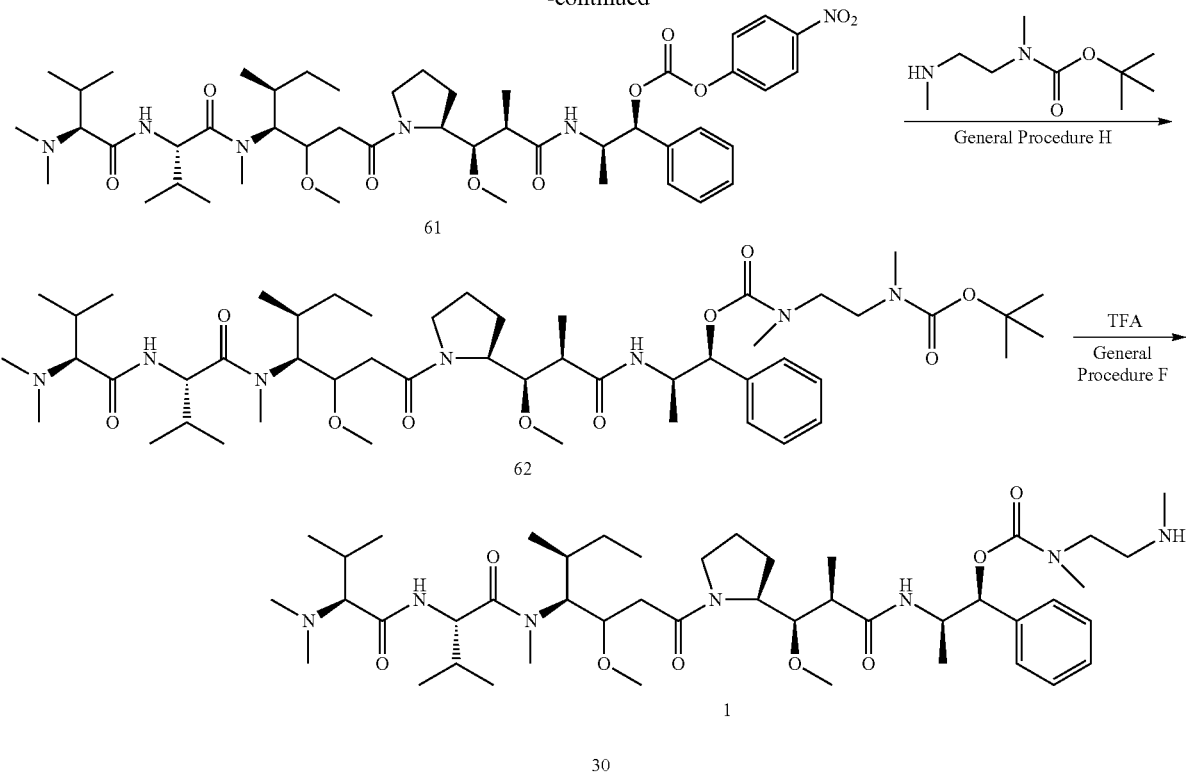

Step 1

DIEA (185 mg, 1.43 mmol) was added to a solution of AE (350 mg, 0.48 mmol) and bis(p-nitrophenyl) carbonate (91 mg, 0.96 mmol) in DCM (10 mL), and the reaction mixture was stirred at rt for 18 h. More bis(p-nitrophenyl) carbonate (142 mg, 0.46 mmol) was added, and the mixture was stirred for 24 h. The mixture was concentrated to remove the solvent, and the residue was purified by silica gel chromatography (EtOAc/PE 4:1→DCM/MeOH 30:1) to give a white solid 61 (340 mg). LC-MS (Method 1): $R_t$=1.66 min; m/z (ES$^+$)=897.5 (M+H)$^+$.

Step 2

Compound 61 (160 mg, 0.18 mmol) was dissolved in DCM (6 mL), to which tert-butyl methyl(2-(methylamino) ethyl)carbamate (67 mg, 0.36 mmol) and DIEA (69 mg, 0.54 mmol) were sequentially added. The reaction mixture was stirred at rt for 18 h, and then concentrated to remove the solvent. The residue was purified by silica gel chromatography (DCM/MeOH 30:1) to give a pale yellow solid 62 (105 mg). LC-MS (Method 2): $R_t$=2.33 min; m/z (ES$^+$)=946.7 (M+H)$^+$.

Step 3

Compound 62 (105 mg) was dissolved in DCM (3 mL), and the solution was cooled to 10° C., to which TFA (3 mL) was added. The reaction mixture was stirred at 10° C. for 4 h, and then concentrated to remove the solvent. The residue was dissolved in EtOAc (20 mL), and the solution was washed with saturated sodium bicarbonate for 3 times. The organic phase was dried and concentrated to give a pale yellow solid 1 (75 mg). LC-MS (Method 1): $R_t$=1.38 min; m/z (ES$^+$)=846.6 (M+H)$^+$.

Example 2

Synthesis of Compound 2, 3 and 4

Compound 2, 3 and 4 were synthesized via the similar method as that for compound 1. Table 1 shows the LC-MS data for compound 2, 3 and 4.

TABLE 1

| Compound | Structure | Synthetic Procedures | LC-MS Method; $R_t$ (min); m/z [M + H]$^+$ |
|---|---|---|---|
| 2 | 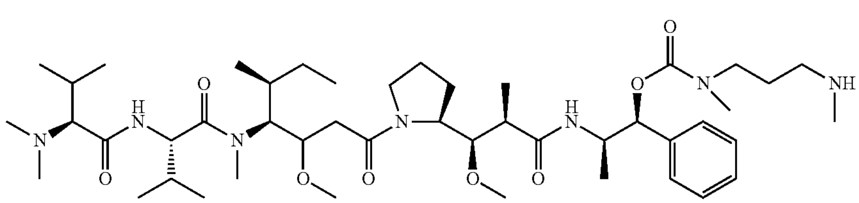 | G,H,F | 2; 2.06; 860.7 |

TABLE 1-continued
| Com-pound | Structure | Synthetic Procedures | LC-MS Method; $R_t$ (min); m/z [M + H]$^+$ |
|---|---|---|---|
| 3 | 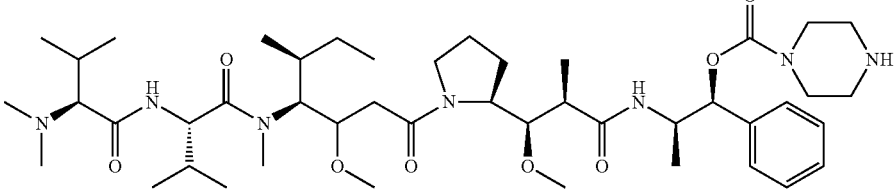 | G,H,F | 2; 1.97; 844.6 |
| 4 | 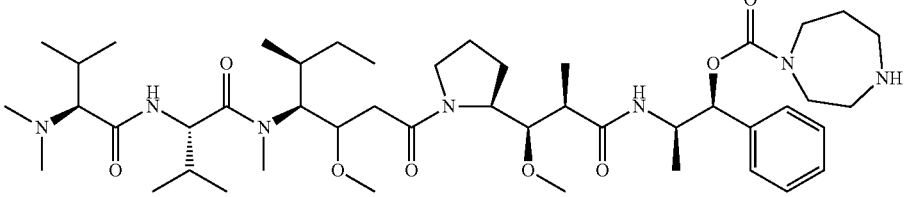 | G,H,F | 2; 2.06; 858.0 |
Example 3
Synthesis of Compound 5
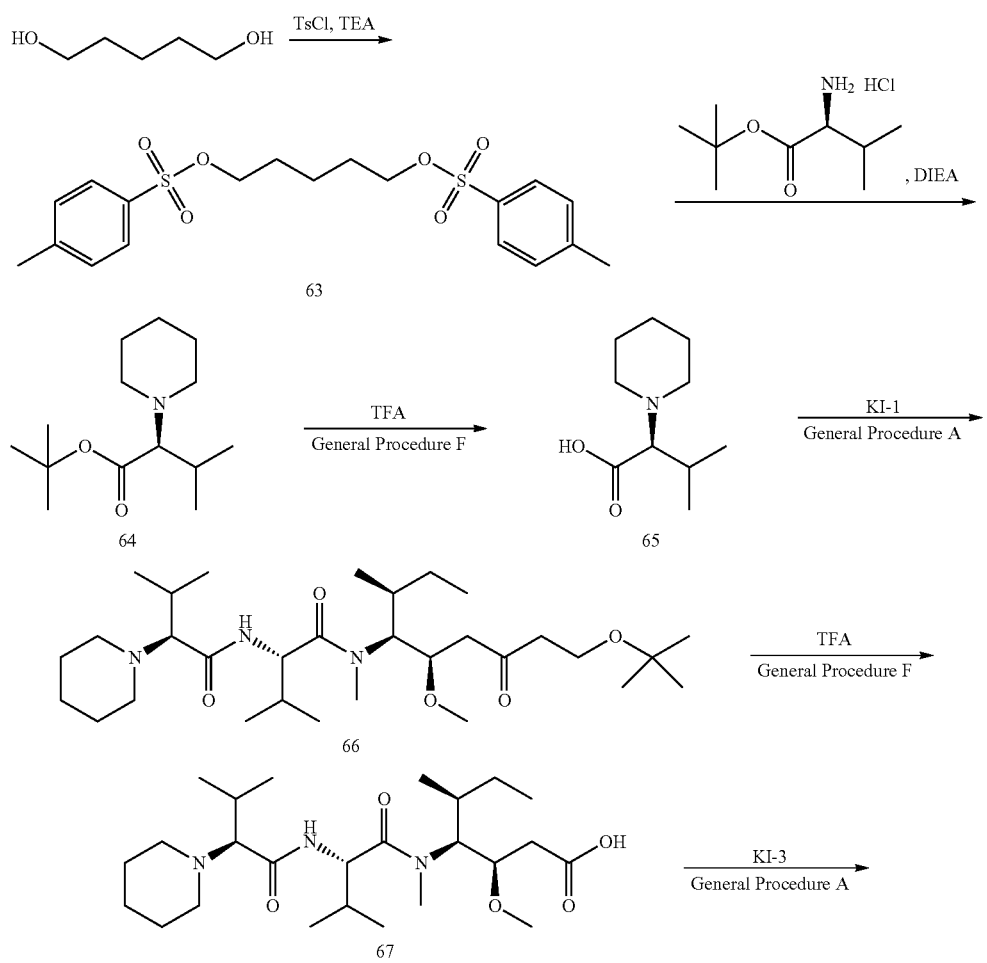

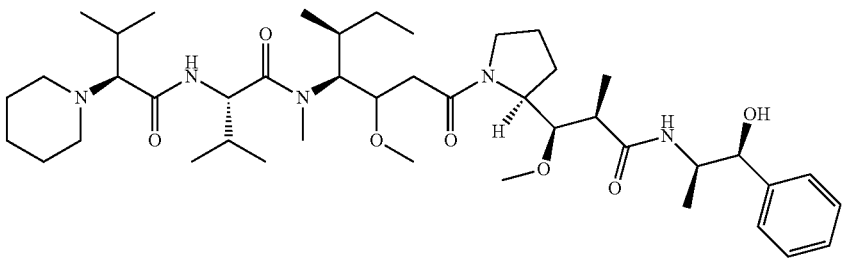

Step 1

1,5-Pentadiol (2.0 g, 19 mmol) and TEA (6.72 g, 66.5 mmol) were dissolved in DCM (100 mL), to which TsCl (8.69 g, 45.6 mmol) was added slowly. The reaction mixture was stirred at rt for 18 h, and then washed sequentially with 10% citric acid solution, water, and brine. The organic phase was dried and concentrated to give a white solid (8.0 g), which was used directly for next step. LC-MS (Method 1): $R_t$=2.10 min; m/z (ES$^+$)=413.1 (M+H)$^+$.

Step 2

Compound 63 (4.8 g, 11.7 mmol) and L-valine tert-butyl ester hydrochloride (2.43 g, 11.7 mmol) were added to DIEA (20 mL), and the reaction mixture was vigorously stirred at 127° C. for 18 h. After cooling, the reaction mixture was concentrated to remove the solvent, and the residue was purified by silica gel chromatography (PE/EtOAc 5:1) to give yellow oil 64 (2.8 g). LC-MS (Method 1): $R_t$=1.14 min; m/z (ES$^+$)=242.3 (M+H)$^+$.

Step 3

Compound 64 (2.8 g) was dissolved in DCM (5 mL), to which TFA (5 mL) was added. The reaction mixture was stirred at rt overnight, and then concentrated to remove the solvent to give a brown solid 65 (1.2 g), which was used directly for next step. Small amount of the crude product was purified by prep-RP-HPLC to give a pure compound for $^1$H NMR analysis. LC-MS (Method 1): $R_t$=0.36 min; m/z (ES$^+$), 186.2 (M+H)$^+$. $^1$H NMR (500 MHz, CDCl$_3$) δ3.82 (d, 1H), 3.65 (d, 1H), 3.54 (d, 1H), 3.37 (t, 1H), 3.03 (t, 1H), 3.33 (m, 1H), 2.10-1.80 (m, 5H), 1.55-1.40 (m, 1H), 1.17 (d, 3H), 1.06 (d, 3H).

Step 4

Compound 65 (200 mg, 50% purity, 0.54 mmol) and KI-1 (194 mg, 0.54 mmol) were dissolved in DCM (9 mL), to which DIEA (272 mg, 2.7 mmol) and DEPC (114 mg, 0.70 mmol) were added sequentially. The reaction mixture was stirred at rt for 18 h, and then concentrated to remove the solvent. The residue was purified by silica gel chromatography (PE/EtOAc 5:1) to give colorless oil 66 (250 mg). LC-MS (Method 1): $R_t$=1.49 min; m/z (ES$^+$), 526.4 (M+H)$^+$.

Step 5

Compound 66 (250 mg) was dissolved in DCM (3 mL), and the solution was cooled to 0° C., to which TFA (3 mL) was added. The reaction mixture was stirred at 10° C. for 4 h, and then concentrated to remove the solvent to give crude product 67 (220 mg), which was used directly for next step. LC-MS (Method 1): $R_t$=1.56 min; m/z (ES$^+$), 470.7 (M+H)$^+$.

Step 6

Compound 67 (220 mg, 0.47 mmol) and KI-3 (160 mg, 0.47 mmol) were dissolved in DCM (8 mL), and the solution was cooled to 0° C., to which TEA (142 mg, 1.41 mmol) and DEPC (99 mg, 0.61 mmol) were sequentially added. The reaction mixture was stirred at rt for 18 h, and then concentrated to remove the solvent. The residue was purified by silica gel chromatography (DCM/MeOH 40:1) to give a pale yellow solid 5 (190 mg). LC-MS (Method 1): $R_t$=1.32 min; m/z (ES$^+$), 772.5 (M+H)$^+$.

Example 4

Synthesis of Compound 6

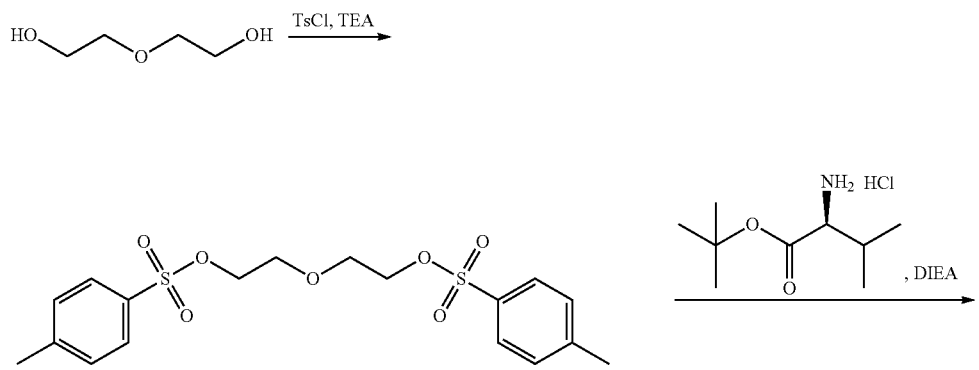

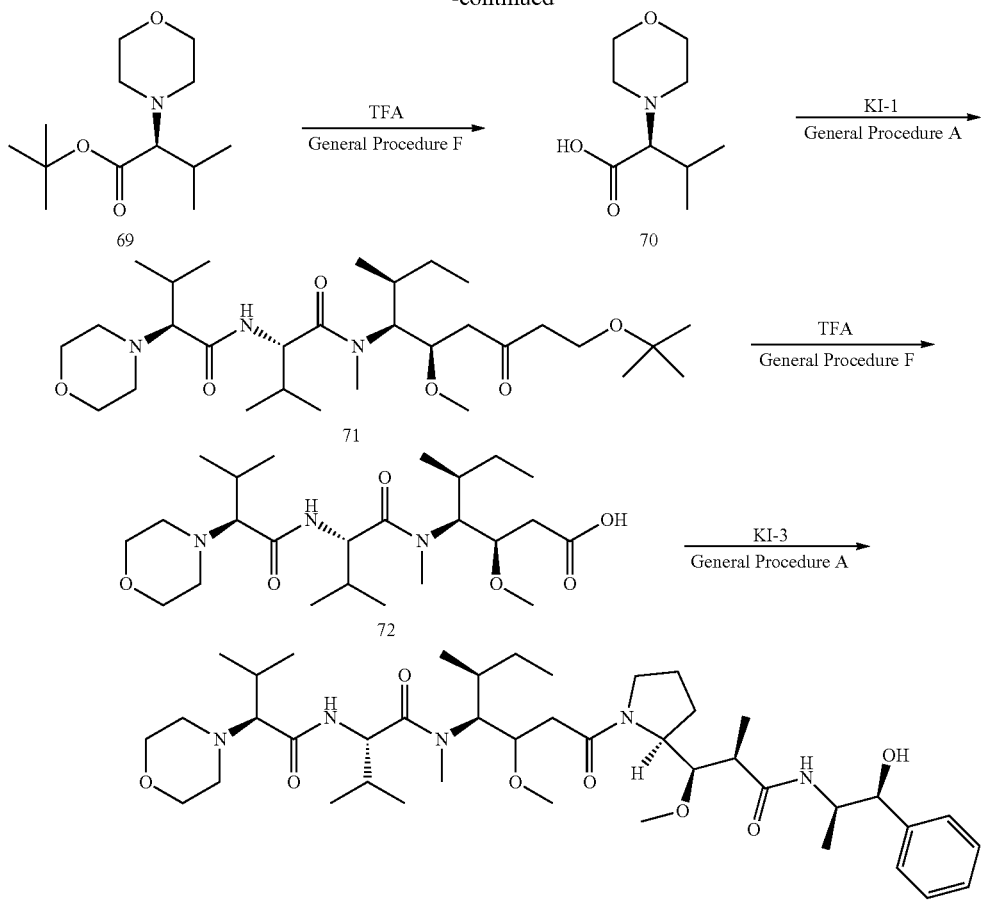

Step 1

Diethylene glycol (2.0 g, 18.9 mmol) and TEA (6.69 g, 66 mmol) were dissolved in DCM (100 mL), to which TsCl (8.63 g, 45.3 mmol) was added slowly. The reaction mixture was stirred at rt for 18 h, and then washed with 10% citric acid solution, water, and brine. The organic phase was dried and concentrated to give a white solid 68 (8.0 g), which was used directly for next step. LC-MS (Method 1): $R_f$=2.02 min; m/z (ES$^+$)=415.1 (M+H)$^+$.

Step 2

Compound 68 (2.95 g, 7.18 mmol) and L-valine tert-butyl ester hydrochloride (1.5 g, 7.18 mmol) were added to DIEA (15 mL), and the reaction mixture was vigorously stirred at 127° C. for 18 h. After cooling down, the mixture was concentrated to remove the solvent, and the residue was purified by silica gel chromatography (PE/EtOAc 5:1) to give yellow oil 69 (0.9 g). LC-MS (Method 1): $R_f$=1.33 min; m/z (ES$^+$)=244.3 (M+H)$^+$.

Step 3

Compound 69 (0.9 g) was dissolved in DCM (2 mL), to which TFA (2 mL) was added. The reaction mixture was stirred at rt overnight, and then concentrated to remove the solvent to give a grey solid 70 (400 mg), which was used directly for next step. Small amount of the crude product was purified by prep-RP-HPLC to give the pure compound for $^1$H NMR analysis. LC-MS (Method 1): $R_f$=0.35, 0.43 min; m/z (ES$^+$)=188.2 (M+H)$^+$. $^1$H NMR (500 MHz, CDCl$_3$) δ4.04 (s, 4H), 3.80 (d, 1H), 3.60 (br s, 2H), 3.36 (br s, 2H), 2.37 (m, 1H), 1.20 (d, 3H), 1.08 (d, 3H).

Step 4

Compound 70 (200 mg, 50% purity, 0.54 mmol) and KI-1 (194 mg, 0.54 mmol) were dissolved in DCM (9 mL), to which DIEA (272 mg, 2.7 mmol) and DEPC (114 mg, 0.70 mmol) were sequentially added. The reaction mixture was stirred at rt for 18 h, and then concentrated to remove the solvent. The residue was purified by silica gel chromatography (PE/EtOAc 5:1) to obtain colorless oil 71 (200 mg). LC-MS (Method 1): $R_f$=1.74 min; m/z (ES$^+$)=528.4 (M+H)$^+$.

Step 5

Compound 71 (200 mg) was dissolved in DCM (3 mL), and the solution was cooled to 0° C., to which TFA (3 mL) was added. The reaction mixture was stirred at 10° C. for 3 h, and then concentrated to remove the solvent to give the crude product 72 (190 mg), which was used directly for next step. LC-MS (Method 1): $R_f$=1.22 min; m/z (ES$^+$)=472.4 (M+H)$^+$.

Step 6

Compound 72 (190 mg, 0.38 mmol) and KI-3 (140 mg, 0.41 mmol) were dissolved in DCM (8 mL), and the solution was cooled to 0° C., to which TEA (115 mg, 1.14 mmol) and DEPC (80 mg, 0.49 mmol) were sequentially added. The reaction mixture was stirred at rt for 18 h, and then concentrated to remove the solvent. The residue was purified by silica gel chromatography (DCM/MeOH 40:1) to give a pale yellow solid 6 (200 mg). LC-MS (Method 1): $R_f$=1.36 min; m/z (ES$^+$)=774.5 (M+H)$^+$.

Example 5
Synthesis of Compound 7
Step 1
Compound KI-4 (200 mg, 0.48 mmol) and bis(p-nitrophenyl) carbonate (298 mg, 0.96 mmol) were dissolved in
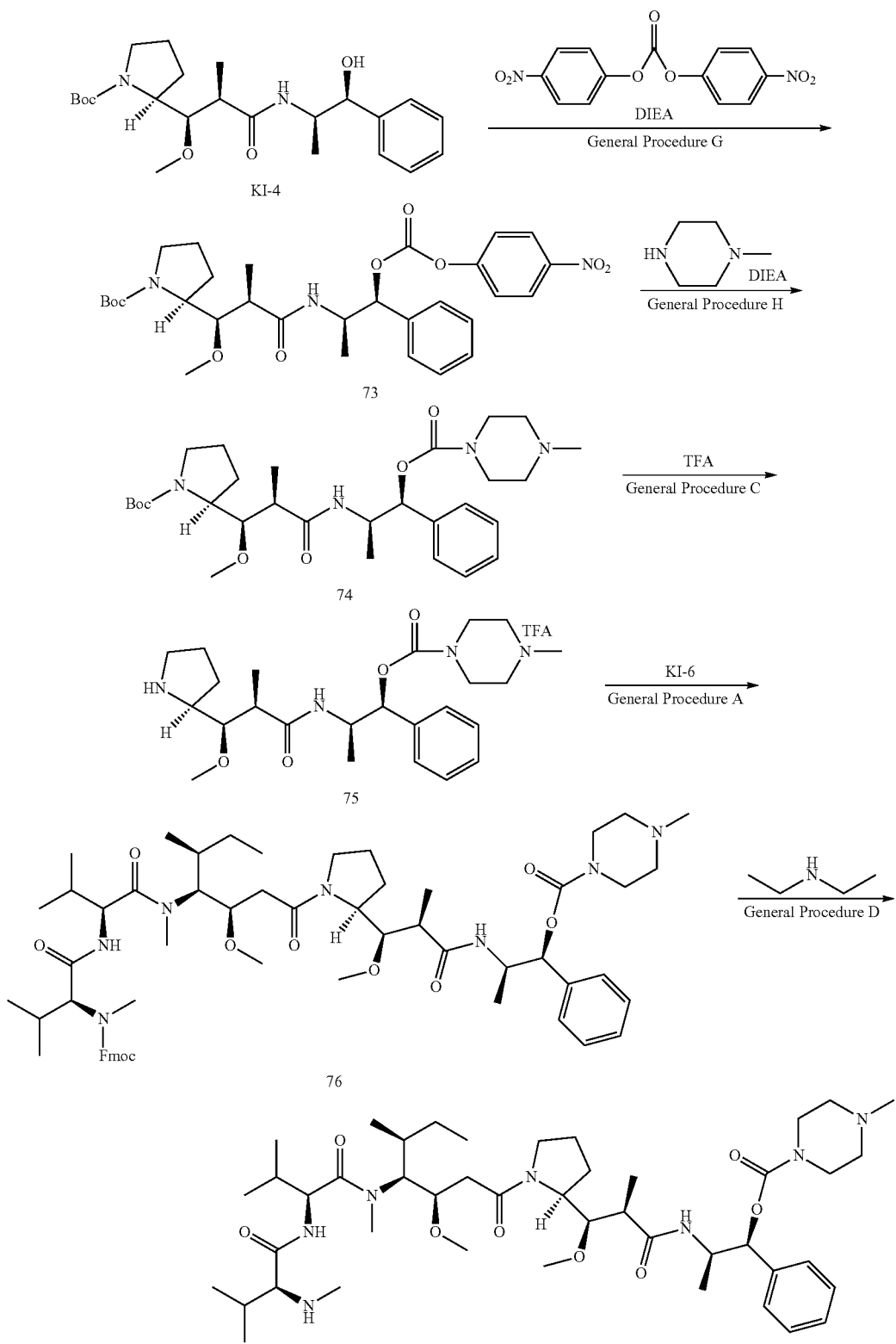

DCM (5 mL), to which DIEA (124 mg, 11 mmol) was added. The reaction mixture was stirred at rt for 18 h, and then concentrated to remove the solvent. The residue was purified by silica gel chromatography (PE/EtOAc 25:1) to give a pale yellow solid 73 (200 mg). LC-MS (Method 2): $R_t$=2.28 min; m/z (ES$^+$)=586.3 (M+H)$^+$.

Step 2

Compound 73 (200 mg, 0.34 mmol) was dissolved in DCM (6 mL), to which 1-methylpiperazine (38 mg, 0.38 mmol) and DIEA (49 mg, 0.38 mmol) were sequentially added. The reaction mixture was stirred at rt for 18 h, and then concentrated to remove the solvent. The residue was purified by prep-RP-HPLC (Method 3: 40%-60% B in 8 min→95% B; $R_t$: 4.2~5.1 min) to give a white solid 74 (135 mg). LC-MS (Method 2): $R_t$=2.01 min; m/z (ES$^+$)=547.3 (M+H)$^+$.

Step 3

Compound 74 (135 mg) was added to a mixed solvent of DCM (6 mL)/TFA (3 mL). The reaction mixture was stirred at rt for 18 h, and then concentrated to remove the solvent to give pale yellow oil 75 (112 mg), which was used directly for next step.

Step 4

Compound 75 (112 mg, 0.25 mmol) and KI-6 (159 mg, 0.25 mmol) were dissolved in DCM (5 mL), to which TEA (25 mg, 0.25 mmol) and DEPC (41 mg, 0.25 mmol) were sequentially added. The reaction mixture was stirred at rt for 18 h, and then diluted by the addition of DCM (25 mL). The mixture was washed sequentially with water and brine, dried, and concentrated. The residue was purified by silica gel chromatography (DCM/MeOH 20:1) to give a white solid 76 (210 mg). LC-MS (Method 1): $R_t$=1.80 min; m/z (ES$^+$)=534.0 [½(M+2H)]$^+$.

Step 5

Compound 76 (86 mg, 0.081 mmol) was added to a mixed solvent of DEA (1 mL)/DCM (3 mL), and the reaction mixture was stirred at rt for 16 h. The mixture was concentrated to remove the solvent, and the residue was purified by prep-RP-HPLC (Method 4: 40%-60% B in 8 min→95% B; $R_t$: 5.1-5.8 min) to give a white solid 7 (40 mg). LC-MS (Method 2): $R_t$=1.97 min; m/z (ES$^+$)=844.5 (M+H)$^+$.

Example 6

Synthesis of Compound 8

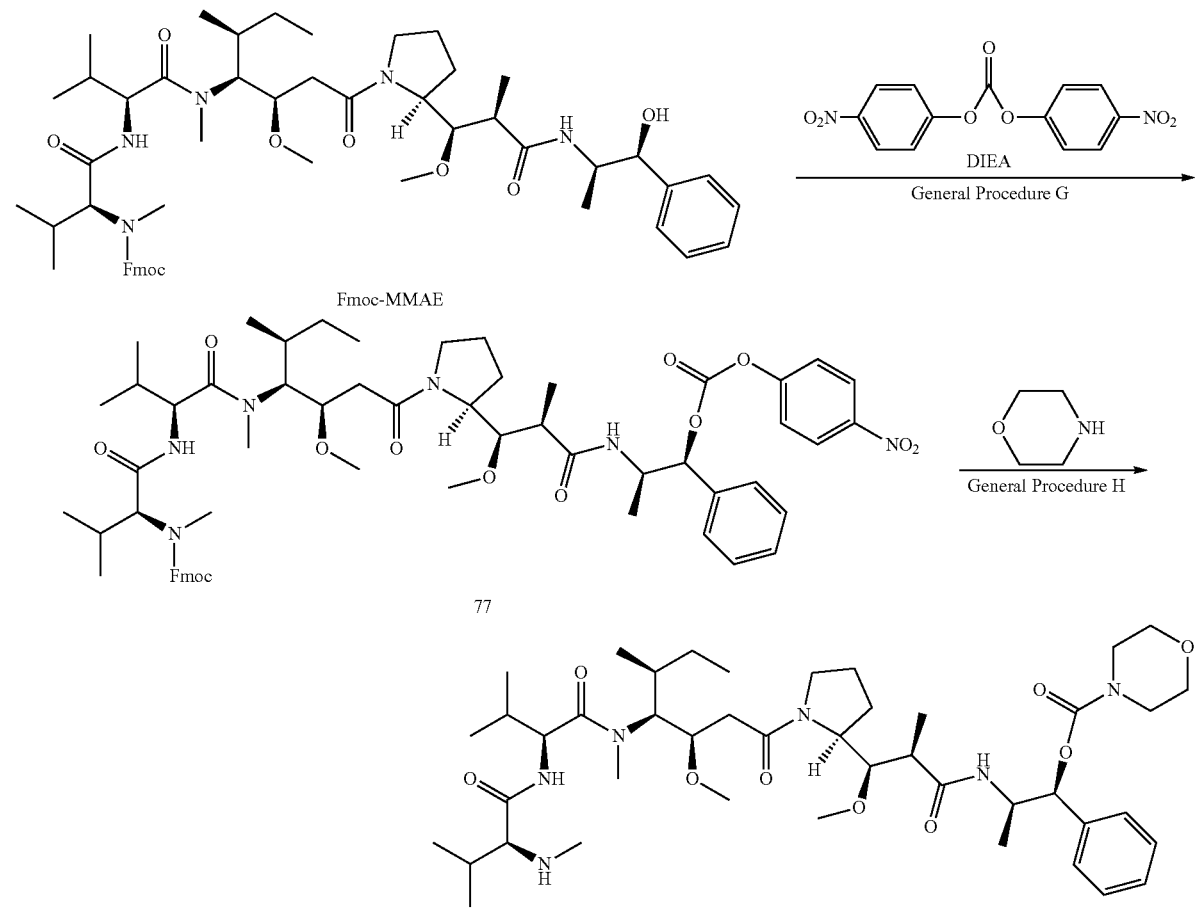

Step 1

Compound Fmoc-MMAE (220 mg, 0.23 mmol) and bis(p-nitrophenyl) carbonate (142 mg, 0.46 mmol) were dissolved in DCM (20 mL), to which DIEA (91 mg, 0.70 mmol) was added. The reaction mixture was stirred at rt for 18 h. More bis(p-nitrophenyl) carbonate (142 mg) was added, and the reaction mixture was stirred overnight. The mixture was concentrated to remove the solvent, and the residue was purified by silica gel chromatography (EtOAc/PE 4:1) to give a white solid 77 (200 mg). LC-MS (Method 1): $R_t$=2.41 min; m/z (ES+) N/A (M+H)+.

Step 2

Compound 77 (70 mg, 0.063 mmol) was dissolved in DCM (6 mL), to which morpholine (0.5 mL) and DIEA (16 mg, 0.13 mmol) were added. The reaction mixture was stirred at rt for 21 h, and then concentrated to remove the solvent. The residue was purified by prep-RP-HPLC (Method 3: 30%-50% B in 8 min→95% B; $R_t$: 9-9.8 min) to give a white solid 8 (26 mg). LC-MS (Method 1): $R_t$=1.52 min; m/z (ES+)=831.5 (M+H)+.

Example 7

Synthesis of Compounds 9-16

Compounds 9-16 were synthesized via the similar method as that for compound 8, which were characterized by LC-MS as shown in Table 2.

TABLE 2

| Compound | Structure | Synthetic Procedure | LC-MS Method; $R_t$ (min); m/z [M + H]+ |
|---|---|---|---|
| 9 | 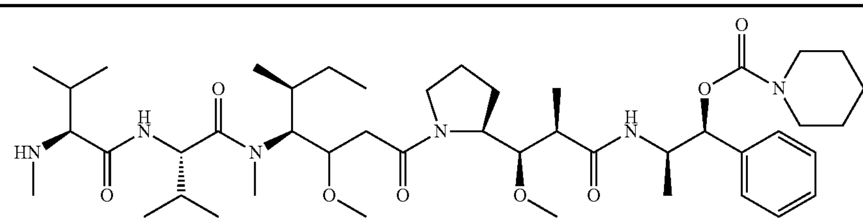 | G,H | 1; 1.63; 829.6 |
| 10 | 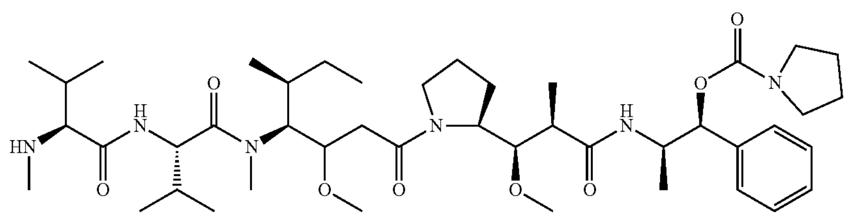 [SMILES: CC[C@H](C)[C@@H](C(CC(=O)N1CCC[C@H]1[C@H](OC)[C@@H](C)C(=O)N[C@H](C)[C@@H](OC(=O)N1CCCC1)c1ccccc1)OC)N(C)C(=O)[C@@H](NC(=O)[C@@H](NC)C(C)C)C(C)C] | G,H | 2; 2.12; 815.5 |
| 11 | 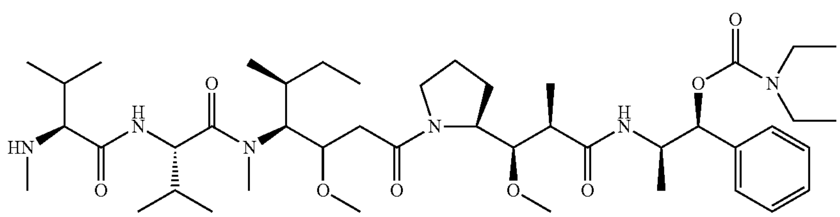 [SMILES: CC[C@H](C)[C@@H](C(CC(=O)N1CCC[C@H]1[C@H](OC)[C@@H](C)C(=O)N[C@H](C)[C@@H](OC(=O)N(CC)CC)c1ccccc1)OC)N(C)C(=O)[C@@H](NC(=O)[C@@H](NC)C(C)C)C(C)C] | G,H | 1; 1.59; 817.6 |
| 12 | 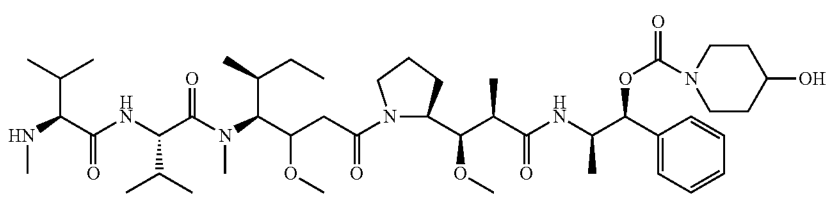 [SMILES: CC[C@H](C)[C@@H](C(CC(=O)N1CCC[C@H]1[C@H](OC)[C@@H](C)C(=O)N[C@H](C)[C@@H](OC(=O)N1CCC(O)CC1)c1ccccc1)OC)N(C)C(=O)[C@@H](NC(=O)[C@@H](NC)C(C)C)C(C)C] | G,H,D | 1; 1.49; 845.5 |
| 13 | 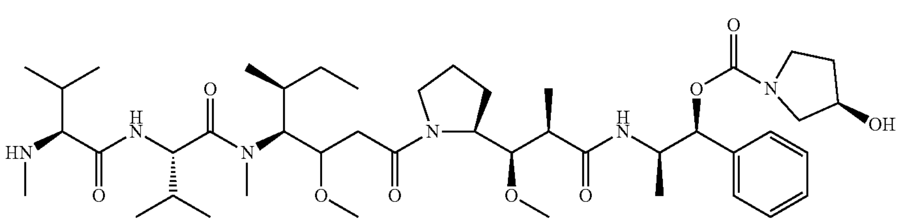 [SMILES: CC[C@H](C)[C@@H](C(CC(=O)N1CCC[C@H]1[C@H](OC)[C@@H](C)C(=O)N[C@H](C)[C@@H](OC(=O)N1CC[C@@H](O)C1)c1ccccc1)OC)N(C)C(=O)[C@@H](NC(=O)[C@@H](NC)C(C)C)C(C)C] | G,H | 1; 1.50; 831.5 |
| 14 | 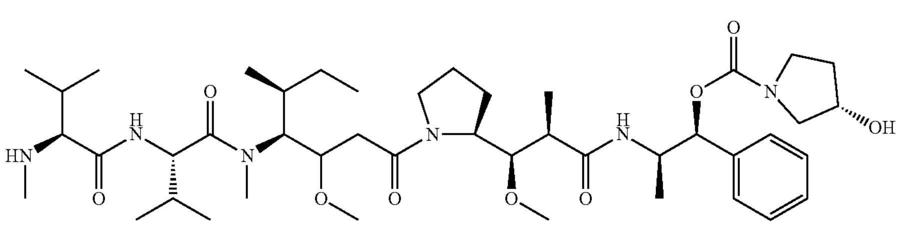 [SMILES: CC[C@H](C)[C@@H](C(CC(=O)N1CCC[C@H]1[C@H](OC)[C@@H](C)C(=O)N[C@H](C)[C@@H](OC(=O)N1CC[C@H](O)C1)c1ccccc1)OC)N(C)C(=O)[C@@H](NC(=O)[C@@H](NC)C(C)C)C(C)C] | G,H,D | 1; 1.49; 831.5 |

TABLE 2-continued

| Compound | Structure | Synthetic Procedure | LC-MS Method; $R_t$ (min); m/z [M + H]$^+$ |
|---|---|---|---|
| 15 | 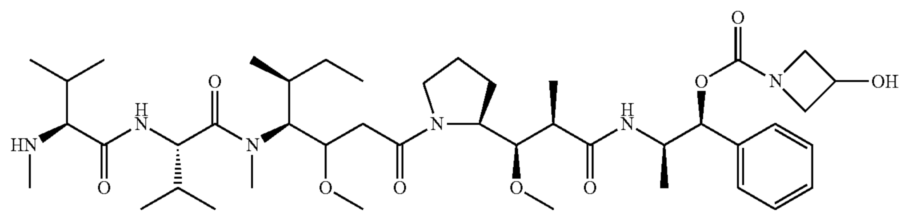 [SMILES: CC[C@H](C)[C@@H](C(CC(=O)N1CCC[C@H]1[C@H](OC)[C@@H](C)C(=O)N[C@H](C)[C@@H](OC(=O)N1CC(O)C1)c1ccccc1)OC)N(C)C(=O)[C@@H](NC(=O)[C@@H](NC)C(C)C)C(C)C] | G,H,D | 1; 1.48; 817.5 |
| 16 | 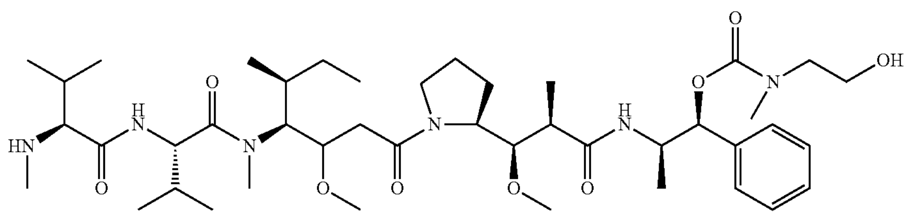 [SMILES: CC[C@H](C)[C@@H](C(CC(=O)N1CCC[C@H]1[C@H](OC)[C@@H](C)C(=O)N[C@H](C)[C@@H](OC(=O)N(C)CCO)c1ccccc1)OC)N(C)C(=O)[C@@H](NC(=O)[C@@H](NC)C(C)C)C(C)C] | G,H,D | 1; 1.48; 819.5 |

Example 8

Synthesis of Compound 17

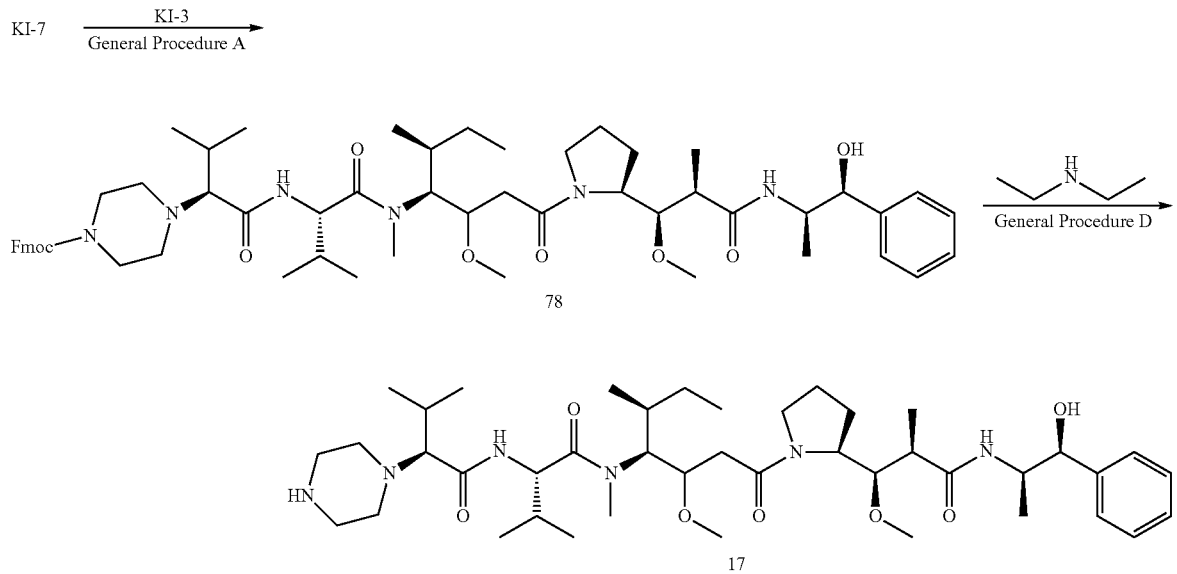

Step 1

Compound KI-7 (80 mg, 0.12 mmol) was dissolved in DCM (6 mL), and then the solution was cooled to 0° C., to which DIEA (44 mg, 0.35 mmol), KI-3 (41 mg, 0.13 mmol), and DEPC (28 mg, 0.17 mmol) were sequentially added. The reaction mixture was stirred at rt for 4 h, and then concentrated to remove the solvent to give crude product 78, which was used directly for next step. LC-MS (Method 1): $R_t$=1.95 min; m/z (ES$^+$)=995.6 (M+H)$^+$.

Step 2

Compound 78 (crude product from Step 1) was dissolved in a mixed solvent of DEA (0.5 mL)/DCM (1 mL), and the reaction mixture was stirred at rt overnight. The mixture was concentrated to remove the solvent, and the residue was purified by prep-RP-HPLC (Method 4: 35%-60% B in 8 min→95% B; $R_t$: 4.5-5.5 min) to give a white solid 17 (60 mg). LC-MS (Method 1): $R_t$=1.49 min; m/z (ES$^+$)=773.5 (M+H)$^+$.

Example 9

Synthesis of Compound 18

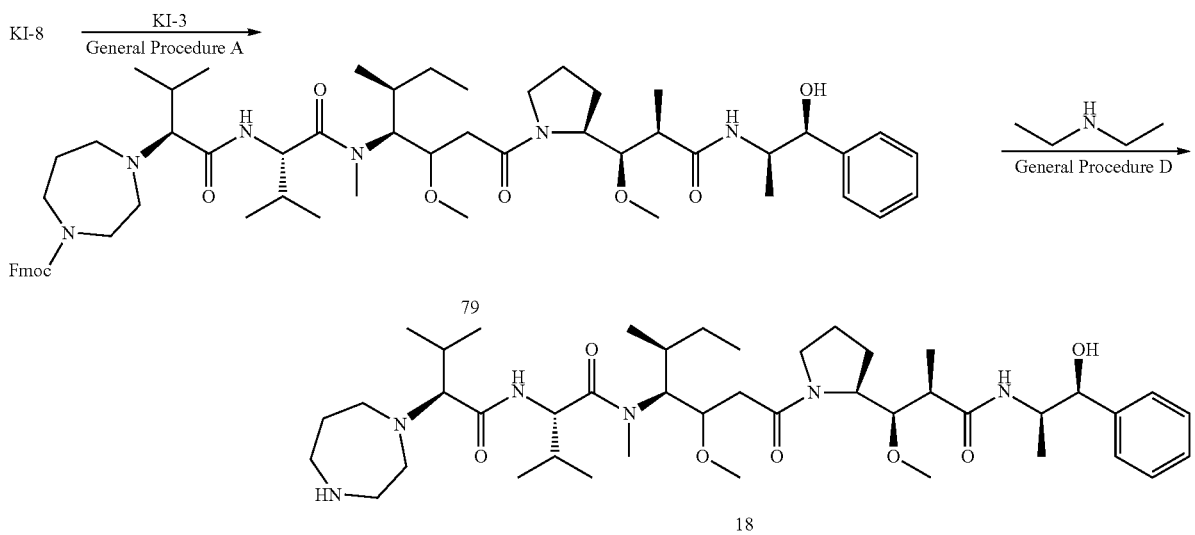

Step 1

Compound KI-8 (287 mg, 0.41 mmol) and KI-3 (130 mg, 0.41 mmol) were dissolved in DCM (10 mL), and then the solution was cooled to 0° C., to which TEA (207 mg, 20.5 mmol) and DEPC (87 mg, 0.53) were sequentially added. The reaction mixture was stirred at rt overnight. The organic phase was washed with water (10 mL×2), dried, and concentrated. The residue was purified by silica gel chromatography (DCM/MeOH 30:1) to give a white solid 79 (200 mg).

Step 2

Compound 79 (200 mg, 0.20 mmol) was added to a mixed solvent of DCM (3 mL)/DEA (0.5 mL), and the reaction mixture was stirred at rt overnight. The mixture was concentrated to remove the solvent, and the residue was purified by prep-RP-HPLC (Method 3: 30%-45% B in 8 min→95% B; $R_t$: 5.0-6.0 min) to give a white solid (110 mg). LC-MS (Method 1): $R_t$=1.40 min; m/z (ES$^+$)=787.5 (M+H)$^+$.

Example 10

Synthesis of Compound 19-21

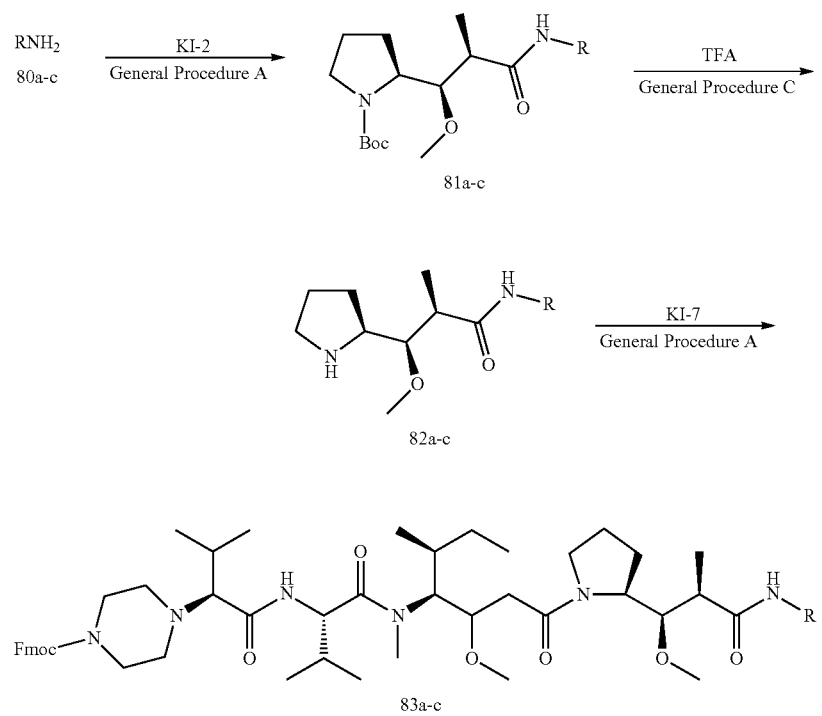

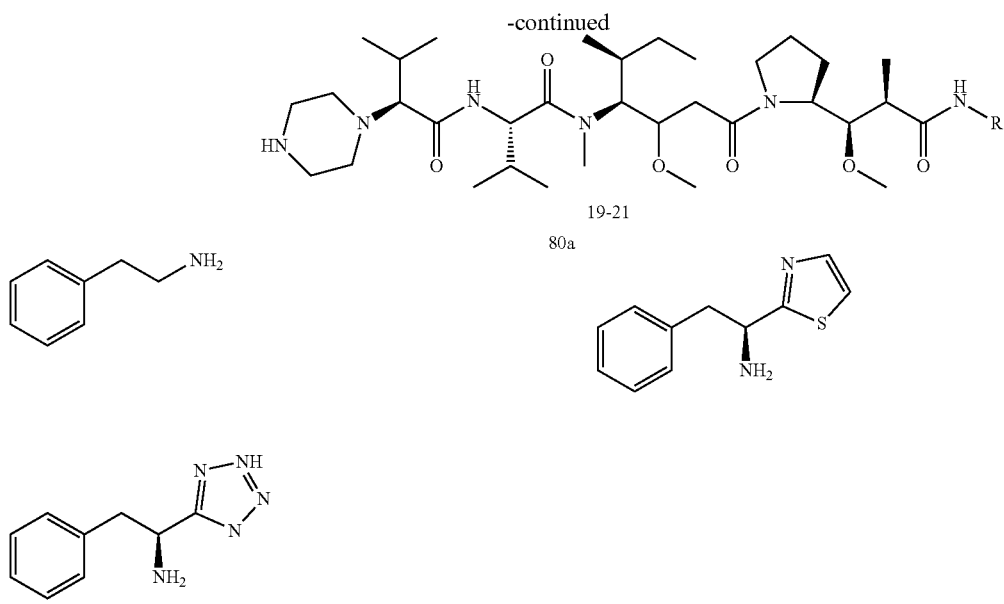

Raw materials 80b (WO 2013/072813) and 80c (WO 2007/008848) were synthesized according to literature methods (with small modification).

Synthesis of Compound 21

Step 1

Compound 80c (210 mg, 1.11 mmol) and KI-2 (351 mg, 1.22 mmol) were dissolved in DCM (20 mL), and the solution was cooled to 0° C., to which TEA (336 mg, 3.33 mmol) and DEPC (235 mg, 1.44 mmol) were sequentially added. The reaction mixture was stirred at rt for 18 h, and then concentrated to remove the solvent. The residue was purified by silica gel chromatography (DCM/MeOH 10:1) to give a pale yellow solid 81c (150 mg). LC-MS (Method 1): $R_t$=1.89 min; m/z (ES$^+$)=459.3 (M+H)$^+$.

Step 2

Compound 81c (150 mg) was dissolved in DCM (2 mL), and the solution was cooled to 0° C., to which TFA (1 mL) was added. The reaction mixture was stirred at 10° C. for 3 h, and then concentrated to remove the solvent to give the crude product 82c (TFA salt, 120 mg), which was used directly for next step. LC-MS (Method 1): $R_t$=1.21 min; m/z (ES$^+$)=359.2 (M+H)$^+$.

Step 3

Compound 82c (120 mg, 0.335 mmol) and KI-7 (231 mg, 0.335 mmol) were dissolved in DCM (10 mL), and the solution was cooled to 0° C., to which DIEA (216 mg, 1.68 mmol) and DEPC (71 mg, 0.435 mmol) were sequentially added. The reaction mixture was stirred at rt for 18 h. The organic phase was washed with water, dried, and concentrated. The residue was purified by silica gel chromatography (DCM/MeOH 40:1 to 15:1) to give pale yellow oil 83c (400 mg). LC-MS (Method 1): $R_t$=2.12 min; m/z (ES$^+$)=517.5 [½(M+2H)]$^+$.

Step 4

Compound 83c (400 mg, 0.387 mmol) was dissolved in DCM (1.5 mL), to which DEA (0.5 mL) was added. The reaction mixture was stirred at rt overnight, and then concentrated to remove the solvent. The residue was purified by prep-RP-HPLC (Method 4: 35%-65% B in 8 min→95% B in 4 min; $R_t$: 4.0-5.0 min) to give a white solid 21 (65 mg). LC-MS (Method 1): $R_t$=1.81 min; m/z (ES$^+$)=811.6 (M+H)$^+$.

Compounds 19-20 were synthesized via the similar method as that for compound 21, and Table 3 shows the LC-MS data for the products.

TABLE 3

| Compound | Structure | Synthetic Procedure | LC-MS Method; $R_t$ (min); m/z [M + H]$^+$ |
|---|---|---|---|
| 19 | 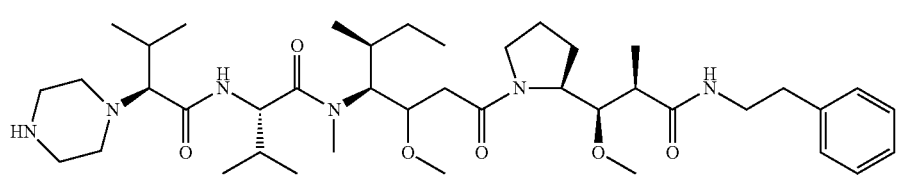 [SMILES: CC[C@H](C)[C@@H](C(CC(=O)N1CCC[C@H]1[C@H](OC)[C@@H](C)C(=O)NCCc1ccccc1)OC)N(C)C(=O)[C@@H](NC(=O)[C@H](C(C)C)N1CCNCC1)C(C)C] | A,C,A,D | 2; 2.02; 743.5 |

TABLE 3-continued

| Compound | Structure | Synthetic Procedure | LC-MS Method; $R_t$ (min); m/z [M + H]$^+$ |
|---|---|---|---|
| 20 | 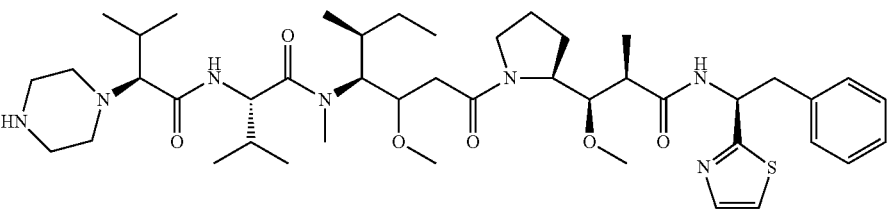 [SMILES: CC[C@H](C)[C@@H](C(CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N1CCNCC1)C(C)C] | A,C,A,D | 2; 2.05; 826.5 |

Example 11

Synthesis of Compound 22

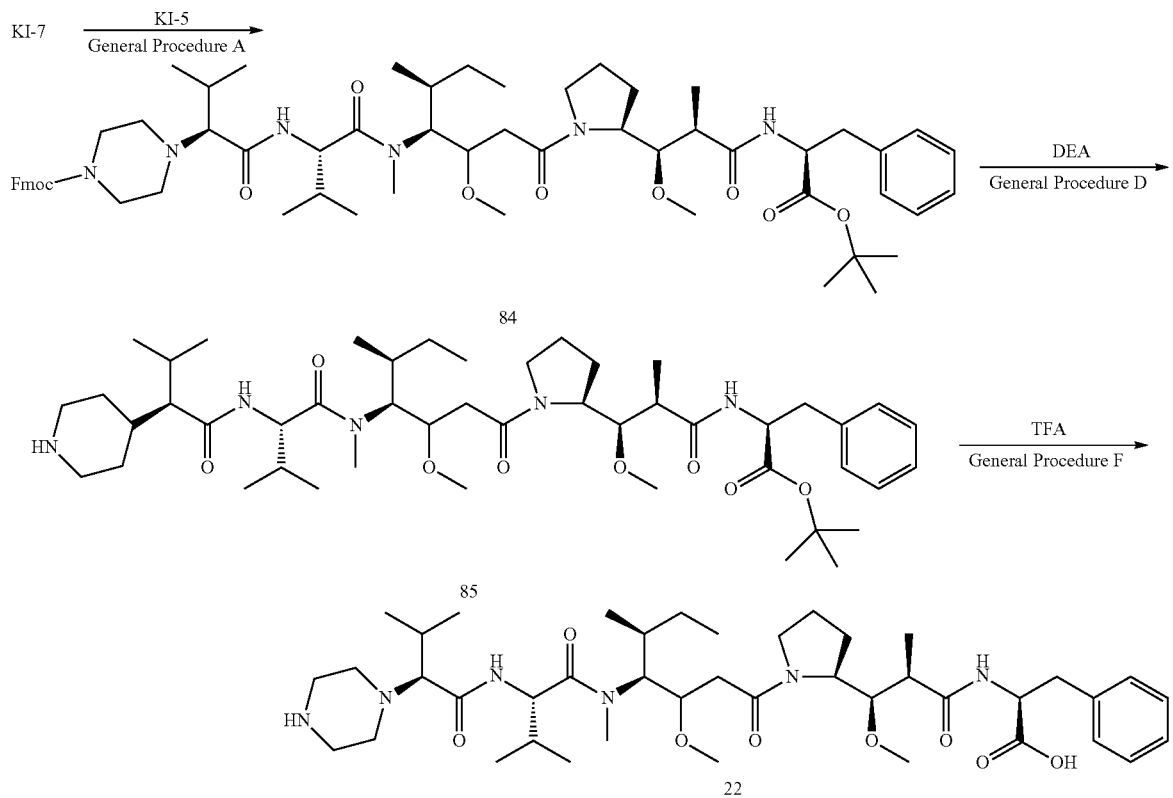

Step 1

Compound KI-7 (166 mg, 0.24 mmol) and KI-5 (103 mg, 0.27 mmol) were dissolved in DCM (10 mL), and the solution was cooled to 0° C., to which DIEA (93 mg, 0.72 mmol) and DEPC (60 mg, 0.36 mmol) were sequentially added. The reaction mixture was stirred at rt for 4 h, and then concentrated to remove the solvent to give the crude product 84, which was used directly for next step. LC-MS (Method 1): $R_t$=2.09 min; m/z (ES$^+$)=1065.7 (M+H)$^+$.

Step 2

DCM (3 mL) and DEA (1 mL) were added to compound 84, the crude product, and the reaction mixture was stirred at rt overnight. The mixture was concentrated to remove the solvent, and the residue was purified by prep-RP-HPLC (Method 4: 40%-70% B in 8 min→95% B in 4 min; $R_t$: 7.3-8.3 min) to give a white solid 85 (60 mg). LC-MS (Method 1): $R_t$=1.66 min; m/z (ES$^+$)=843.6 (M+H)$^+$.

Step 3

Compound 85 (8 mg) was dissolved in DCM (0.6 mL), and the solution was cooled to 0° C., to which TFA (0.2 mL) was added. The reaction mixture was stirred at 10° C. for 3 h, and then concentrated to remove the solvent. The residue was purified by prep-RP-HPLC (Method 3: 20%-30% B in 8.2 min→95% B in 4 min; $R_t$: 8.2-9.0 min) to give a white solid 22 (5 mg). LC-MS (Method 1): $R_t$=1.36 min; m/z (ES$^+$)=787.5 (M+H)$^+$.

Example 12

Synthesis of Compound 23

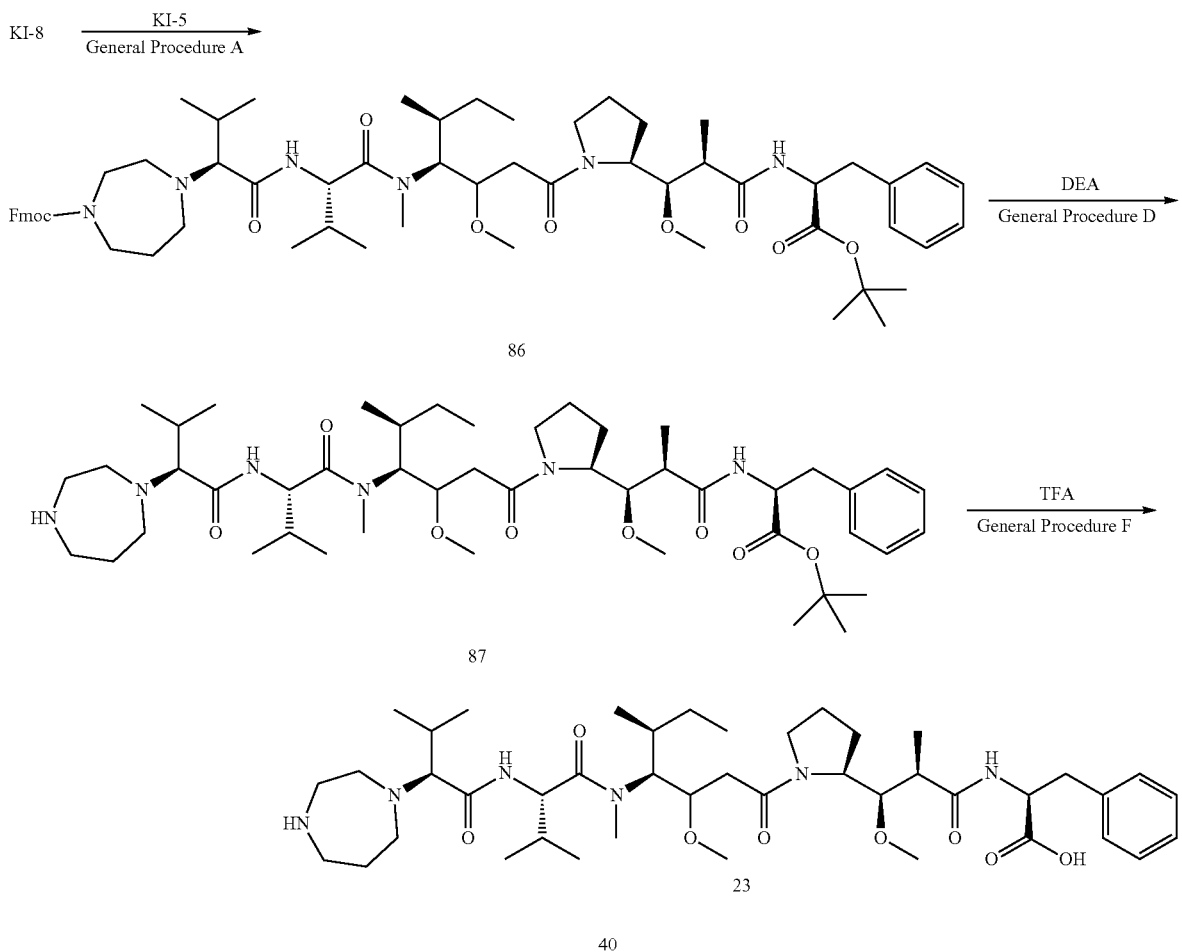

Step 1

Compounds KI-8 (314 mg, 0.45 mmol) and KI-5 (173 mg, 0.45 mmol) were dissolved in DCM (10 mL), and the solution was cooled to 0° C., to which TEA (135 mg, 1.34 mmol) and DEPC (94 mg, 0.58 mmol) were sequenticially added. The reaction mixture was stirred at rt overnight, and then washed with water, dried, and concentrated. The crude product was purified by silica gel chromatography (DCM/MeOH 30:1) to give a white solid 86 (200 mg).

Step 2

Compound 86 (400 mg, 0.37 mmol) was dissolved in a mixed solvent of DCM (3 mL)/DEA (1 mL), and the reaction mixture was stirred at rt overnight. The mixture was concentrated to remove the solvent, and the residue was purified by prep-RP-HPLC (Method 3: 33%-58% B in 8 min→95% B in 4 min; $R_t$: 7.5-9.5 min) to give a white solid 87 (240 mg). LC-MS (Method 1): $R_t$=1.51 min; m/z (ES$^+$), 857.5 (M+H)$^+$.

Step 3

Compound 87 (10 mg, 0.012 mmol) was dissolved in DCM (0.6 mL), and the solution was cooled to 0° C., to which TFA (0.2 mL) was added. The reaction mixture was stirred at 10° C. for 2.5 h, and then concentrated to remove the solvent. The residue was purified by prep-RP-HPLC (Method 3: 20%-30% B in 8.2 min→95% B in 4 min; $R_t$: 7.7-8.8 min) to give a white solid 23 (5 mg). LC-MS (Method 1): $R_t$=1.36 min; m/z (ES$^+$)=801.5 (M+H)$^+$.

Example 13

Synthesis of Compounds 24-30

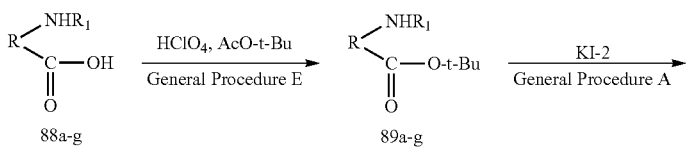

-continued
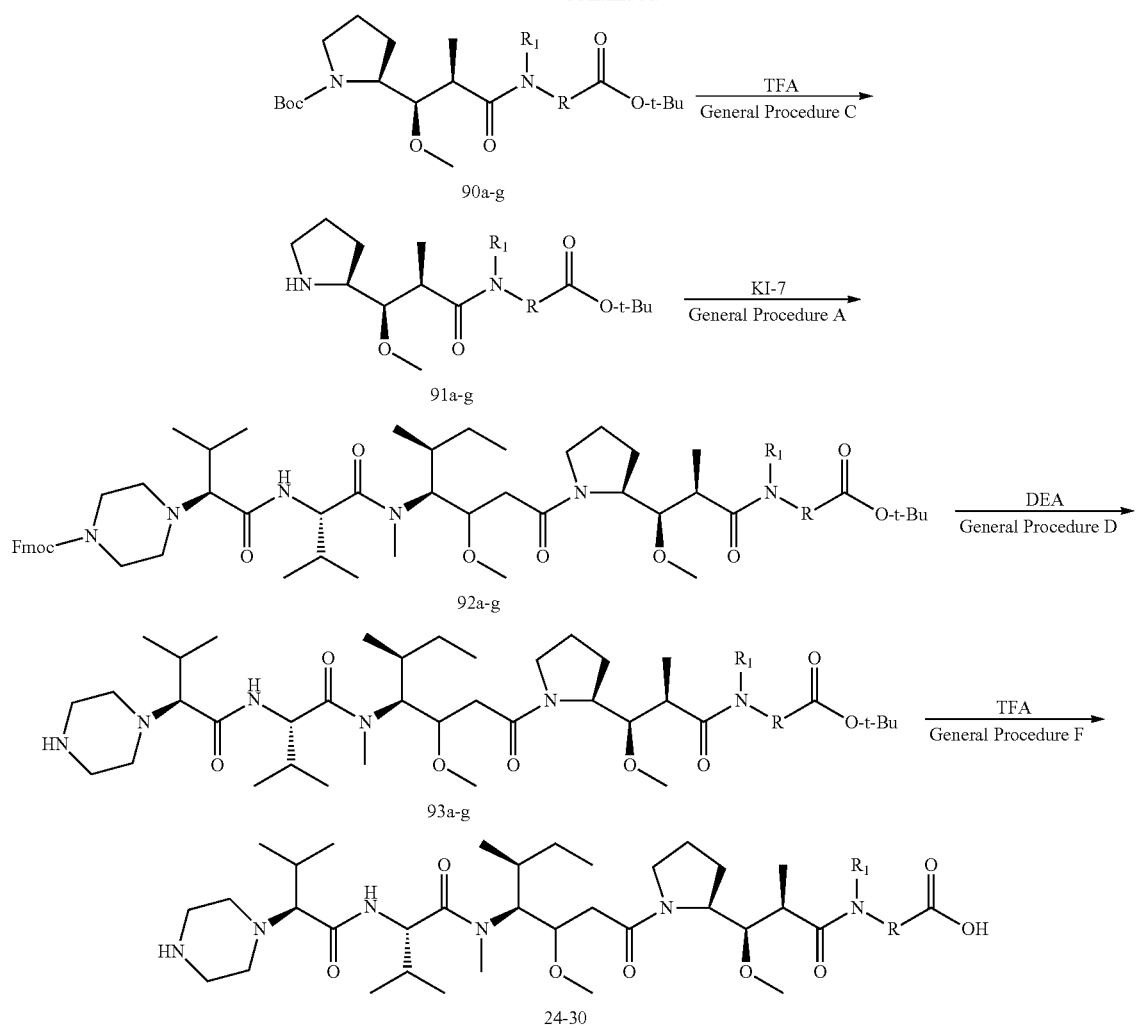
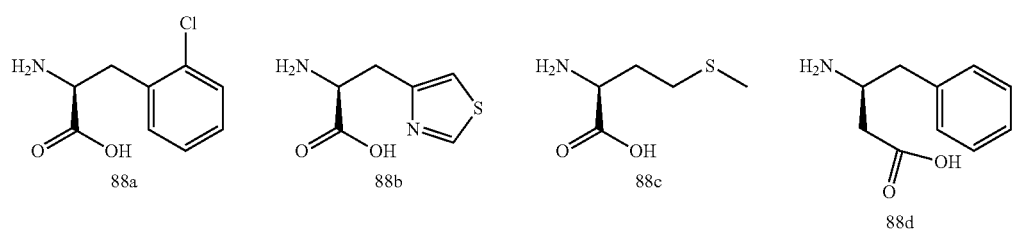
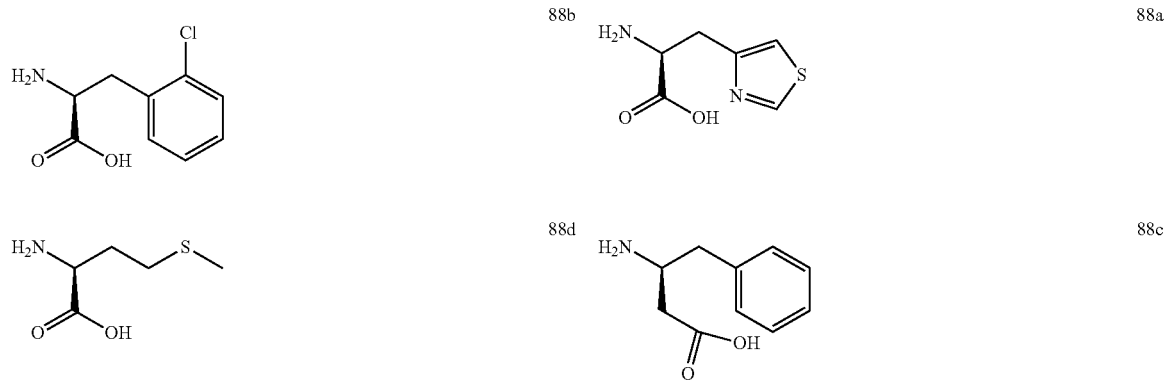

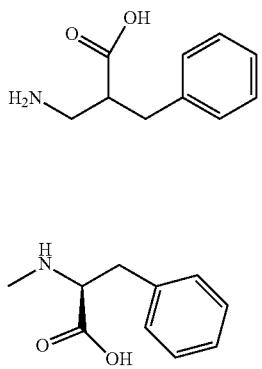

88e

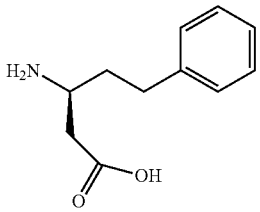

88f

88g

Step 1: Synthesis of Amino Acid Tert-Butyl Ester
Synthesis of Compound 89a

Compound 88a (500 mg, 2.5 mmol) was dissolved in tert-butyl acetate (5 mL), and the solution was cooled to 0° C., to which perchloric acid (0.21 mL, 3.76 mmol) was added dropwise. The reaction mixture was stirred at rt for 12 h. The organic phase was washed with water (10 mL) and 1.0 M hydrochloric acid (15 mL). 10% potassium carbonate solution was added to the combined aqueous phase to adjust pH-9, and then the aqueous phase was extracted with DCM (20 mL×3). The combined organic phase was dried and concentrated, and the residue was purified by silica gel chromatography (EtOAc/PE 1:5) to give colorless oil 89a (430 mg). LC-MS (Method 1): $R_t$=1.57 min; m/z (ES$^+$), 256.1 (M+H)$^+$. $^1$H NMR (500 MHz, DMSO-d$_6$) δ 8.61 (s, 2H), 7.47 (d, 1H), 7.38-7.32 (m, 3H), 4.15 (m, 1H), 3.21 (m, 2H), 1.22 (s, 9H).

Synthesis of Compound 89b

Via the similar method as that for compound 89a, compound 89b (colorless oil, 42 mg) was synthesized from compound 88b (500 mg, 2.5 mmol). LC-MS (Method 2): $R_t$=1.65 min; m/z (ES$^+$), 229.2 (M+H)$^+$. $^1$H NMR (500 MHz, DMSO-d$_6$) δ 9.11 (s, 1H), 8.40 (s, 2H), 7.56 (s, 1H), 4.27 (s, 1H), 3.32-3.19 (m, 2H), 1.32 (s, 9H).

Synthesis of Compound 89c

Compound 88c (1.0 g, 6.71 mmol) was dissolved in tert-butyl acetate (6 mL), and the solution was cooled to 0° C., to which perchloric acid (0.81 mL, 10.1 mmol) was added dropwise. The reaction mixture was stirred at rt for 18 h. The white precipitate was removed by filtration, and washed with ethyl acetate. The filtrate was concentrated to give colorless oil 89c (130 mg), which was used directly for next step. LC-MS (Method 1): $R_t$=1.17 min; m/z (ES$^+$)=206.1 (M+H)$^+$.

Synthesis of Compound 89d

Via the similar method as that for compound 89a, 89d (colorless oil, 340 mg) was synthesized from compound 88d (HCl salt, 500 mg, 2.32 mmol). LC-MS (Method 1): $R_t$=1.82 min; m/z (ES$^+$)=236.2 (M+H)$^+$. $^1$H NMR (500 MHz, CDCl$_3$) δ 8.36 (s, 1H), 7.33-7.25 (m, 3H), 7.17 (d, 2H), 3.70 (s, 1H), 3.22 (m, 1H), 2.85 (m, 1H), 2.60-2.55 (m, 2H), 1.42 (s, 9H).

Synthesis of Compound 89e

Via the similar method as that for compound 89a, compound 89e (83 mg) was synthesized from compound 88e (260 mg, 1.45 mmol). LC-MS (Method 1): $R_t$=1.62 min; m/z (ES$^+$)=236.2 (M+H)$^+$. $^1$H NMR (500 MHz, CDCl$_3$) δ 8.08 (s, 2H), 7.30-7.19 (m, 3H), 7.14 (d, 2H), 3.06-2.96 (m, 4H), 2.87 (dd, 1H), 1.37 (s, 9H).

Synthesis of Compound 89f

Via the similar method as that for compound 89a, 89f (colorless oil, 320 mg) was synthesized from compound 88f (HCl salt, 500 mg, 2.18 mmol). LC-MS (Method 1): $R_t$=1.88 min; m/z (ES$^+$)=250.2 (M+H)$^+$. $^1$H NMR (500 MHz, DMSO-d$_6$) δ 8.03 (s, 2H), 7.34-7.27 (m, 2H), 7.21-7.20 (m, 3H), 3.46 (m, 1H), 2.75-2.60 (m, 4H), 1.83 (m, 2H), 1.41 (s, 9H).

Synthesis of Compound 89g

Compound 89g was synthesized according to literature method (Tetrahedron 2005, 61, 11132-11140). LC-MS (Method 1): $R_t$=1.66 min; m/z (ES$^+$)=236.2 (M+H)$^+$. $^1$H NMR (500 MHz, CDCl$_3$) δ 7.33-7.20 (m, 5H), 3.93 (dd, 1H), 3.38 (dd, 1H), 3.16 (dd, 1H), 2.72 (s, 3H), 1.30 (s, 9H).

Synthesis of Compound 24
Step 2

Compound 89a (235 mg, 0.92 mmol) and KI-2 (220 mg, 0.77 mmol) were dissolved in DCM (4 mL), to which DIEA (267 μL, 1.53 mmol) and DEPC (134 μL, 0.92 mmol) were sequentially added. The reaction mixture was stirred at rt overnight, and then concentrated to remove the solvent. The residue was purified by silica gel chromatography (PE/EtOAc 4:1) to give compound 90a (276 mg). LC-MS (Method 2): $R_t$=2.36 min; m/z (ES$^+$)=525.3 (M+H)$^+$.

Step 3

Compound 90a (276 mg, 0.53 mmol) was dissolved in DCM, and the solution was cooled to 0° C., to which TFA (1 mL, 25 eq) was added. The reaction mixture was stirred at rt for 3 h, and then concentrated to remove the solvent. The residue was neutralized with saturated sodium bicarbonate solution, and the mixture was extracted with DCM (20 mL×3). The combined organic phase was dried and concentrated to give the crude product 91a (115 mg), which was used directly for next step. LC-MS (Method 2): $R_t$=1.96 min; m/z (ES$^+$)=425.3 (M+H)$^+$.

Step 4

Compound 91a (100 mg, 0.24 mmol) and KI-7 (163 mg, 0.24 mmol) were dissolved in DCM (4 mL), to which DIEA (82 μL, 0.47 mmol) and DEPC (41 μL, 0.28 mmol) were sequentially added. The reaction mixture was stirred at rt overnight, and then concentrated to remove the solvent. The residue was purified by silica gel chromatography DCM/MeOH 50:1) to give compound 92a (163 mg). LC-MS (Method 1): $R_t$=2.21 min; m/z (ES$^+$)=519.4 (M+H)$^+$.

Step 5

Compound 92a (163 mg, 0.15 mmol) was dissolved in a mixed solvent of DEA (1 mL)/DCM (3 mL), and the reaction mixture was stirred at rt overnight. The mixture was concentrated to remove the solvent, and the residue was purified by silica gel chromatography (DCM/MeOH/NH$_3$·H$_2$O 15:1:0.1) to give compound 93a (84 mg). LC-MS (Method 2): R$_t$=2.35 min; m/z (ES$^+$)=877.5 (M+H)$^+$.

Step 6

Compound 93a (2.0 mg, 0.0023 mmol) was dissolved in DCM (0.4 mL), to which TFA (0.2 mL) was added. The reaction mixture was stirred at rt for 2 h, and then concentrated to remove the solvent. The residue was purified by prep-RP-HPLC (Method 3: 15%-60% B in 8 min→95% B in 4 min; R$_t$: 9.6 min) to give pure product 24. LC-MS (Method 1): R$_t$=1.56 min; m/z (ES$^+$)=821.3 (M+H)$^+$.

Synthesis of Compounds 25-30

Compounds 25-30 were synthesized via the similar method as that for compound 24, and Table 4 shows the LC-MS data.

TABLE 4

| Compound | Structure | Synthetic Procedure | LC-MS Method; R$_t$ (min); m/z [M + H]$^+$ |
|---|---|---|---|
| 25 | 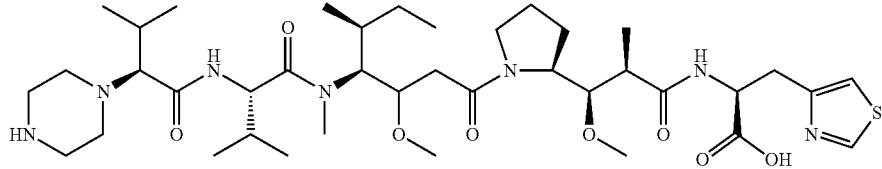 [SMILES: CC[C@H](C)[C@@H](C(CC(=O)N1CCC[C@H]1[C@H](OC)[C@@H](C)C(=O)N[C@@H](Cc1cscn1)C(=O)O)OC)N(C)C(=O)[C@@H](NC(=O)[C@H](C(C)C)N1CCNCC1)C(C)C] | A,C,A,D,F | 1; 1.31; 794.4 |
| 26 | 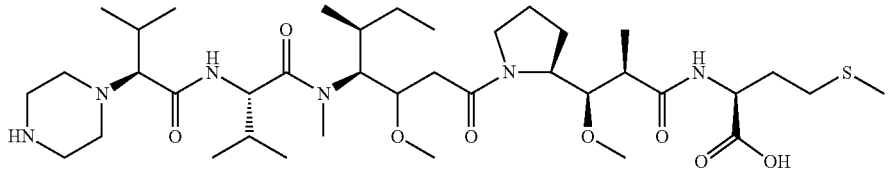 [SMILES: CC[C@H](C)[C@@H](C(CC(=O)N1CCC[C@H]1[C@H](OC)[C@@H](C)C(=O)N[C@@H](CCSC)C(=O)O)OC)N(C)C(=O)[C@@H](NC(=O)[C@H](C(C)C)N1CCNCC1)C(C)C] | A,C,A,D,F | 1; 1.32; 771.4 |
| 27 | 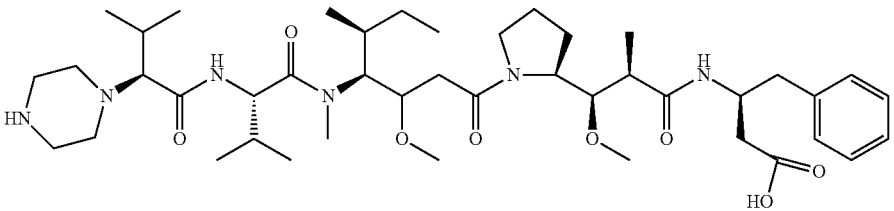 [SMILES: CC[C@H](C)[C@@H](C(CC(=O)N1CCC[C@H]1[C@H](OC)[C@@H](C)C(=O)N[C@H](CC(=O)O)Cc1ccccc1)OC)N(C)C(=O)[C@@H](NC(=O)[C@H](C(C)C)N1CCNCC1)C(C)C] | A,C,A,D,F | 1; 1.54; 801.5 |
| 28 | 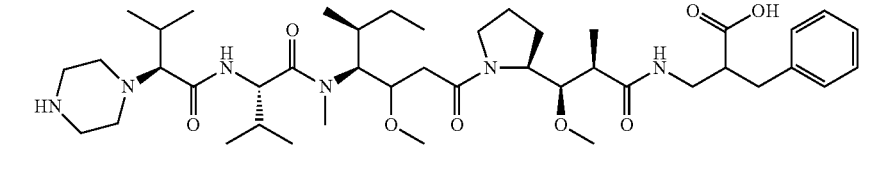 [SMILES: CC[C@H](C)[C@@H](C(CC(=O)N1CCC[C@H]1[C@H](OC)[C@@H](C)C(=O)NCC(Cc1ccccc1)C(=O)O)OC)N(C)C(=O)[C@@H](NC(=O)[C@H](C(C)C)N1CCNCC1)C(C)C] | A,C,A,D,F | 1; 1.53; 801.4 |
| 29 | 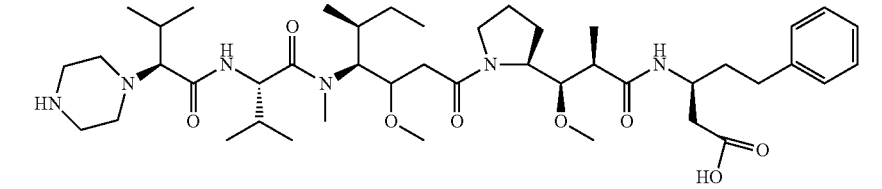 [SMILES: CC[C@H](C)[C@@H](C(CC(=O)N1CCC[C@H]1[C@H](OC)[C@@H](C)C(=O)N[C@@H](CCc1ccccc1)CC(=O)O)OC)N(C)C(=O)[C@@H](NC(=O)[C@H](C(C)C)N1CCNCC1)C(C)C] | A,C,A,D,F | 1; 1.59; 815.6 |
| 30 | 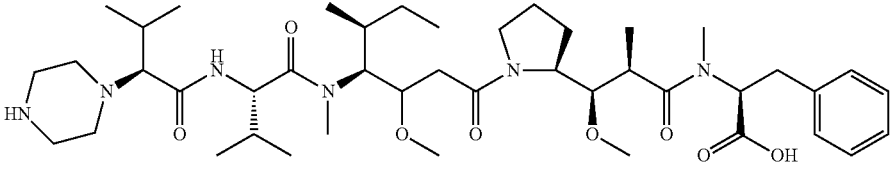 [SMILES: CC[C@H](C)[C@@H](C(CC(=O)N1CCC[C@H]1[C@H](OC)[C@@H](C)C(=O)N(C)[C@@H](Cc1ccccc1)C(=O)O)OC)N(C)C(=O)[C@@H](NC(=O)[C@H](C(C)C)N1CCNCC1)C(C)C] | A,C,A,D,F | 1; 1.61; 801.5 |

Example 14
Synthesis of Compounds 31-46
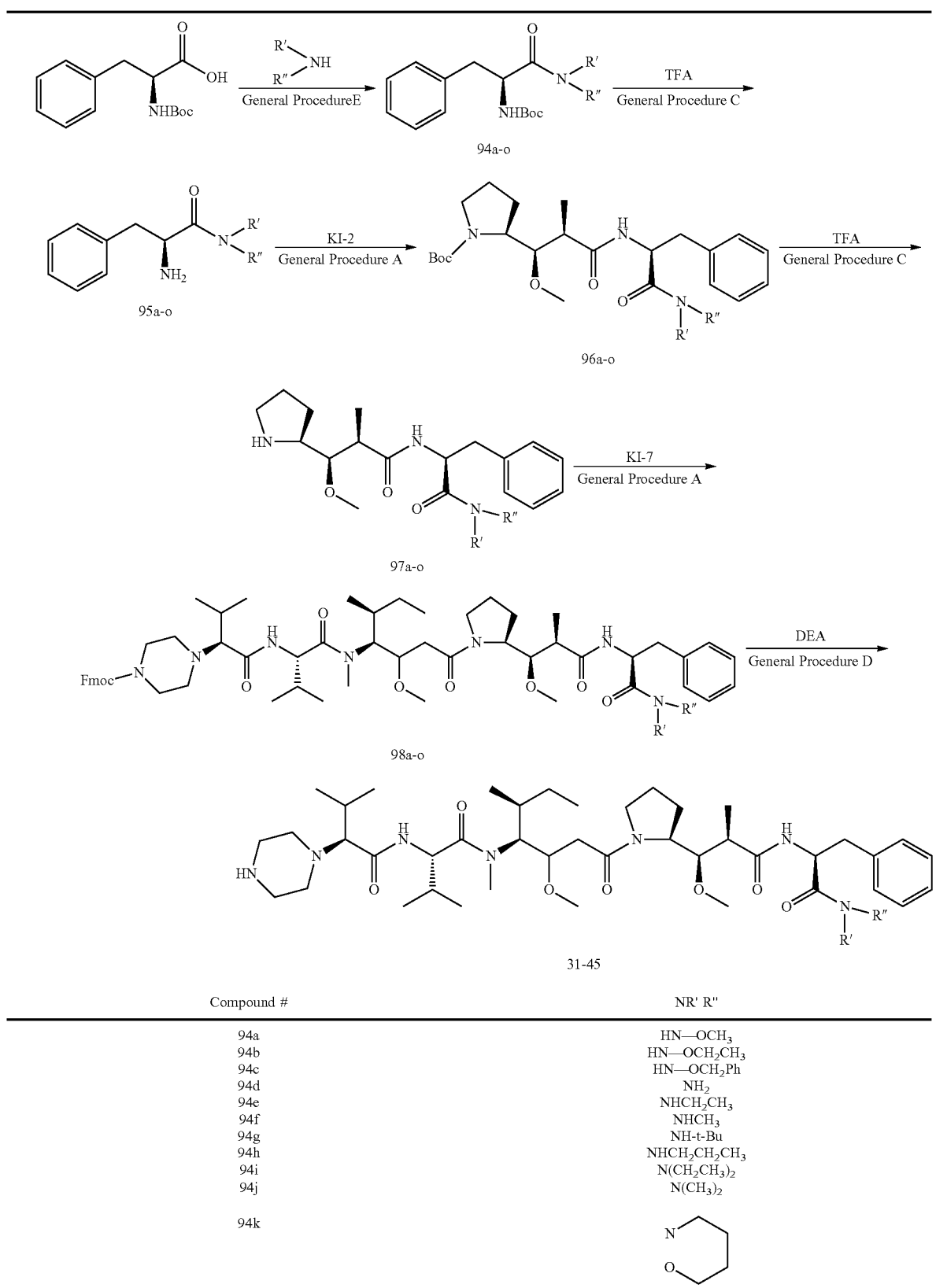
| Compound # | NR' R" |
|---|---|
| 94a | HN—OCH$_3$ |
| 94b | HN—OCH$_2$CH$_3$ |
| 94c | HN—OCH$_2$Ph |
| 94d | NH$_2$ |
| 94e | NHCH$_2$CH$_3$ |
| 94f | NHCH$_3$ |
| 94g | NH-t-Bu |
| 94h | NHCH$_2$CH$_2$CH$_3$ |
| 94i | N(CH$_2$CH$_3$)$_2$ |
| 94j | N(CH$_3$)$_2$ |
| 94k | morpholino |

| | |
|---|---|
| 94l | NH—(CH$_2$CH$_2$O)$_4$H |
| 94m | NH—(CH$_2$CH$_2$O)$_3$H |
| 94n | NH—(CH$_2$CH$_2$O)$_6$H |
| 94o | NH—(CH$_2$CH$_2$O)$_3$CH$_3$ |

Step 1: Synthesis of Compounds 94a-o
Synthesis of Compound 94a

N-Boc-L-Phenylalanine (155 mg, 0.58 mmol) and O-methylhydroxylamine hydrochloride (98 mg, 1.17 mmol) were dissolved in DCM (2 mL), to which TEA (235 mg, 2.32 mmol) and DEPC (114 mg, 0.70 mmol) were sequentially added. The reaction mixture was stirred at rt overnight, and then concentrated to remove the solvent. The residue was purified by silica gel chromatography (DCM/MeOH 50:1) to give a white solid 94a (133 mg). LC-MS (Method 2): R$_t$=1.83 min; m/z (ES$^+$)=317.0 (M+Na)$^+$.

Synthesis of Compound 94b

Compound 94b (white solid) was synthesized via the similar method as that for compound 94a. LC-MS (Method 2): R$_t$=1.89 min; m/z (ES$^+$)=331.2 (M+Na)$^+$.

Synthesis of Compound 94c

Compound 94c (white solid) was synthesized via the similar method as that for compound 94a. LC-MS (Method 2): R$_t$=2.06 min; m/z (ES$^+$)=393.0 (M+Na)$^+$.

Synthesis of Compound 94e

N-Boc-L-phenylalanine (200 mg, 0.75 mmol) was dissolved in THF (2 mL), and the solution was cooled to −10° C., to which N-methylmorpholine (83 mg, 0.82 mmol) and methyl chloroformate (77 mg, 0.82 mmol) were added. The reaction mixture was stirred for 20 min, and then ethylamine (33% in water, 307 mg, 2.25 mmol) was added. The reaction mixture was stirred at rt overnight, and then concentrated to remove the solvent. The residue was purified by silica gel chromatography (DCM/MeOH 50:1) to give a white solid 94e (217 mg). LC-MS (Method 2): R$_t$=1.92 min; m/z (ES$^+$)=315.3 (M+Na)$^+$.

Synthesis of 94f

N-Boc-L-phenylalanine (265 mg, 1 mmol) was dissolved in THF (4 mL), and the solution was cooled to −20° C., to which N-methylmorpholine (101 mg, 1 mmol) and iso-butyl chloroformate (137 mg, 1 mmol) were sequentially added. The reaction mixture was stirred for 3 min, and then methylamine (30% in water, 220 μL, 1.3 mmol) was added. The reaction mixture was stirred for another 1 h, and then 5% sodium bicarbonate solution (4 mL) was added. The mixture was stirred at rt for 30 min, and then extracted with DCM (20 mL×3). The combined organic phase was washed with brine, dried, and concentrated. The residue was purified by silica gel chromatography (PE/EtOAc 2:1) to give compound 94f (173 mg). LC-MS (Method 2): R$_t$=1.85 min; m/z (ES$^+$)=179.2 (M+H−100)$^+$.

Synthesis of Compound 94g

N-Boc-L-phenylalanine (150 mg, 0.57 mmol), tert-butylamine (42 mg, 0.57 mmol) and TEA (115 mg, 1.14 mmol) were dissolved in THF (5 mL), and the solution was cooled to 0° C., to which BOP reagent (328 mg, 0.74 mmol) was added. The reaction mixture was stirred at 0° C. for 2 h, and then warmed to rt and stirred overnight. Water was added to quench the reaction, and the mixture was concentrated to remove the volatile solvent. The aqueous phase was extracted with EtOAc (20 mL×3), and the combined organic phase was washed with brine, dried, and concentrated. The residue was purified by silica gel chromatography (PE/EtOAc 3:1) to give compound 94g (137 mg). LC-MS (Method 2): R$_t$=2.10 min; m/z (ES$^+$)=321.3 (M+H)$^+$.

Synthesis of Compound 94h

Compound 94h (white solid) was synthesized via the similar method as that for compound 94a. LC-MS (Method 2): R$_t$=1.99 min; m/z (ES$^+$)=329.3 (M+Na)$^+$.

Synthesis of Compound 94i

Compound 94i (white solid) was synthesized via the similar method as that for compound 94a. LC-MS (Method 2): R$_t$=2.11 min; m/z (ES$^+$)=321.3 (M+H)$^+$.

Synthesis of Compound 94j

N-Boc-L-phenylalanine (350 mg, 1.32 mmol) and N-hydroxysuccinimide (182 mg, 1.58 mmol) were dissolved in THF (8 mL), and the solution was cooled to 0° C., to which DCC (326 mg, 1.58 mmol) was added. The reaction mixture was stirred at 0° C. for 30 min, and then warmed to rt and stirred for 6 h. The solid was removed by filtration, and the filtrate was cooled to 0° C., to which dimethylamine (33% in water, 4.9 mL, 31.7 mmol) was added. The reaction mixture was stirred at 0° C. for 30 min, and then warmed to rt and stirred overnight. The mixture was concentrated to remove the volatile solvent, and the aqueous phase was extracted with ethyl acetate. The organic phase was washed sequentially with 5% citric acid solution, saturated sodium bicarbonate solution, and brine, dried, and concentrated. The residue was purified by silica gel chromatography (EtOAc/PE 1:4) to give compound 94j. LC-MS (Method 2): R$_t$=1.96 min; m/z (ES$^+$)=293.2 (M+H)$^+$.

Synthesis of Compound 94k

N-Boc-L-phenylalanine (159 mg, 0.60 mmol) was dissolved in DMF (5 mL), and the solution was cooled to 0° C., to which compound 1,2-oxazinane hydrochloride (150 mg, 1.20 mmol, see J. Chem. Soc. 1942, 432), HOBt (122 mg, 0.90 mmol), EDCI (138 mg, 0.72 mmol), and DIEA (314 μL, 1.80 mmol) were sequentially added. The reaction mixture was warmed to rt and stirred for 24 h, and then a mixed solvent composed of 50% saturated ammonium chloride solution and EtOAc was added. The organic phase was separated, washed with saturated sodium bicarbonate solution and brine sequentially, dried, and concentrated to give compound 94k (167 mg). LC-MS (Method 1): R$_t$=1.95 min; m/z (ES$^+$)=357.2 (M+Na)$^+$.

Synthesis of Compound 94l

N-Boc-L-phenylalanine (187 mg, 0.71 mmol) was dissolved in DMF (5 mL), and the solution was cooled to 0° C., to which 2-[2-(2-aminoethoxy)ethoxy]ethanol (150 mg, 0.78 mmol), HOBt (95 mg, 0.71 mmol), and EDCI (135 mg, 0.71 mmol) were sequentially added. The reaction mixture was warmed to rt and stirred for 24 h. Solvent was removed by concentration, and the residue was dissolved in EtOAc.

The organic phase was washed sequentially with water, 1 N hydrochloric acid, 1 N sodium hydroxide solution, and brine, dried, and concentrated. The residue was purified by silica gel chromatography (DCM/MeOH 50:1) to give compound 94l (278 mg). LC-MS (Method 1): $R_f$=1.67 min; m/z (ES$^+$)=441.3 (M+H)$^+$.

Synthesis of Compound 94m

N-Boc-L-phenylalanine (99 mg, 0.42 mmol) was dissolved in DMF (3 mL), and the solution was cooled to 0° C., to which 14-amino-3,6,9,12-tetraoxatetradecanol (100 mg, 0.38 mmol), HOBt (51 mg, 0.38 mmol) and EDCI (73 mg, 0.38 mmol) were sequentially added. The reaction mixture was warmed to rt and stirred for 24 h, and then concentrated to remove the solvent. The residue was dissolved in EtOAc, and the organic phase was washed sequentially with water, 1 N hydrochloric acid, 1 N sodium hydroxide solution, and brine, dried, and concentrated. The residue was purified by silica gel chromatography (DCM/MeOH 30:1) to give compound 94m (215 mg). LC-MS (Method 1): $R_f$=1.39 min; m/z (ES$^+$)=485.3 (M+H)$^+$. $^1$H NMR (500 MHz, DMSO-d$_6$) δ 8.49 (t, 1H), 8.20 (s, 2H), 7.33-7.23 (m, 5H), 3.97 (m, 1H), 3.52-3.27 (m, 20H), 3.17-3.15 (m, 1H), 3.01-2.98 (m, 2H).

Synthesis of Compound 94n

N-Boc-L-phenylalanine (80 mg, 0.28 mmol) was dissolved in DMF (3 mL), and the solution was cooled to 0° C., to which 17-amino-3,6,9,12,15-pentaoxaheptanol (68 mg, 0.26 mmol), HOBt (35 mg, 0.26 mmol) and EDCI (50 mg, 0.26 mmol) were sequentially added. The reaction mixture was warmed to rt and stirred for 24 h. The mixture was concentrated to remove the solvent, and the residue was dissolved in EtOAc. The organic phase was washed sequentially with water, 1 N hydrochloric acid, 1 N sodium hydroxide solution, and brine, dried, and concentrated. The residue was purified by silica gel chromatography (DCM/MeOH 30:1) to give compound 94n (90 mg). LC-MS (Method 1): $R_f$=1.40 min; m/z (ES$^+$)=529.3 (M+H)$^+$. $^1$H NMR (500 MHz, CDCl$_3$) δ 7.30-7.20 (m, 5H), 4.36 (br s, 1H), 3.75-3.40 (m, 21H), 3.25-2.90 (m, 6H), 1.39 (s, 9H).

Synthesis of Compound 94o

N-Boc-L-phenylalanine (44 mg, 0.17 mmol) was dissolved in DMF (3 mL), and the solution was cooled to 0° C., to which 2-(2-(2-methoxyethoxy)ethoxy)ethyl-1-amine (30 mg, 0.17 mmol), HOBt (23 mg, 0.17 mmol) and EDCI (32 mg, 0.17 mmol) were sequentially added. The reaction mixture was stirred at rt for 24 h, and then concentrated to remove the solvent. The residue was dissolved in EtOAc, and the solution was washed sequentially with water, 1 N hydrochloric acid, 1 N sodium hydroxide solution, and brine, dried, and concentrated. The residue was purified by silica gel chromatography (DCM/MeOH 50:1) to obtain compound 94o (59 mg). LC-MS (Method 2): $R_f$=1.90 min; m/z (ES$^+$)=411.3 (M+H)$^+$. $^1$H NMR (500 MHz, DMSO-d$_6$) δ 7.96 (t, 1H), 7.30-7.23 (m, 4H), 7.19 (m, 1H), 6.87 (d, 1H), 4.12 (m, 1H), 3.50 (m, 6H), 3.44-3.39 (m, 4H), 3.26-3.16 (m, 5H), 2.92 (dd, 1H), 2.71 (dd, 1H), 1.29 (s, 9H).

Synthesis of Compound 43

Step 2:

Compound 94l (278 mg, 0.63 mmol) was dissolved in DCM (5 mL), and the solution was cooled to 0° C., to which TFA (1.2 mL, 16 mmol) was added. The reaction mixture was stirred at rt for 3 h, and then concentrated to remove the solvent. The residue was neutralized with saturated sodium bicarbonate, and the mixture was extracted with DCM (20 mL×3). The combined organic phase was dried and concentrated, and the residue was purified by silica gel chromatography (DCM/MeOH 20:1) to give 95l (158 mg). LC-MS (Method 1): $R_f$=0.98 min; m/z (ES$^+$)=341.1 (M+H)$^+$. $^1$H NMR (500 MHz, DMSO-d$_6$) δ 7.91 (t, 1H), 7.27-7.19 (m, 5H), 4.61 (s, 1H), 3.50-3.47 (m, 10H), 3.41-3.34 (m, 5H), 3.25-3.16 (m, 2H), 2.91 (dd, 1H), 2.60 (dd, 1H), 1.71 (br s, 2H).

Step 3

Compound 95l (35 mg, 0.10 mmol) and KI-2 (27 mg, 0.092 mmol) were dissolved in DCM (2 mL), to which DIEA (33 µL, 0.18 mmol) and DEPC (16 µL, 0.11 mmol) were sequentially added. The reaction mixture was stirred at rt overnight, to which DCM (20 mL) was added. The solution was washed with brine, and the aqueous phase was extracted with DCM (20 mL×2). The combined organic phase was dried and concentrated to give crude product 96l (83 mg), which was used directly for next step. LC-MS (Method 1): $R_f$=1.47 min; m/z (ES$^+$)=610.4 (M+H)$^+$.

Step 4

Compound 96l (83 mg, 0.14 mmol) was dissolved in DCM (3 mL), and the solution was cooled to 0° C., to which TFA (0.30 mL, 4.1 mmol) was added. The reaction mixture was stirred at rt for 3 h, and then concentrated to remove the solvent. The residue was neutralized with saturated sodium bicarbonate, and the mixture was extracted with DCM (20 mL×3). The combined organic phase was dried and concentrated, and the residue was purified by silica gel chromatography (DCM/MeOH/NH3.H2O 10:1:0.1) to give 97l (43 mg). LC-MS (Method 1): $R_f$=1.08 min; m/z (ES$^+$)=510.4 (M+H)$^+$.

Step 5

Compound 97l (43 mg, 0.084 mmol) and KI-7 (58 mg, 0.084 mmol) were dissolved in DCM (4 mL), to which DIEA (30 µL, 0.17 mmol) and DEPC (15 µL, 0.10 mmol) were sequentially added. The reaction mixture was stirred at rt overnight, to which brine (30 mL) was added. The mixture was extracted with DCM (20 mL×3), and the combined organic phase was dried and concentrated to give crude product 98l (70 mg), which was used directly for next step. LC-MS (Method 1): $R_f$=1.63 min; m/z (ES$^+$)=1184.6 (M+H)$^+$.

Step 6

Compound 98l (75 mg, 0.059 mmol) was dissolved in a mixed solvent of DCM (3 mL)/DEA (3 mL), and the reaction mixture was stirred at rt overnight. The mixture was concentrated to remove the solvent, and the residue was purified by silica gel chromatography (DCM/MeOH/NH$_3$.H$_2$O 10:1:0.1) to give compound 42 (35 mg). LC-MS (Method 2): $R_f$=1.63 min; m/z (ES$^+$)=962.5 (M+H)$^+$.

Synthesis of Compounds 31-41, 43-45

Starting from compounds 94a-k, 94m-o, compounds 31-41, 43-45 were synthesized via the similar method as that for compound 42, and Table 5 shows the LC-MS data.

TABLE 5

| Compound | Structure | Synthetic Procedure | LC-MS Method; R$_t$ (min); m/z [M + H]$^+$ |
|---|---|---|---|
| 31 | 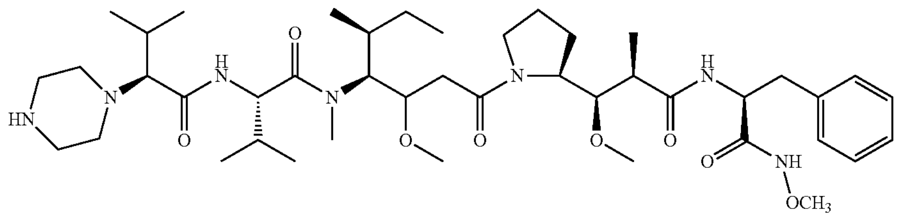 [SMILES: CC[C@H](C)[C@@H](C(CC(=O)N1CCC[C@H]1[C@H](OC)[C@@H](C)C(=O)N[C@@H](Cc1ccccc1)C(=O)NOC)OC)N(C)C(=O)[C@@H](NC(=O)[C@H](C(C)C)N1CCNCC1)C(C)C] | C,A,C,A,D | 2; 1.88; 816.5 |
| 32 | 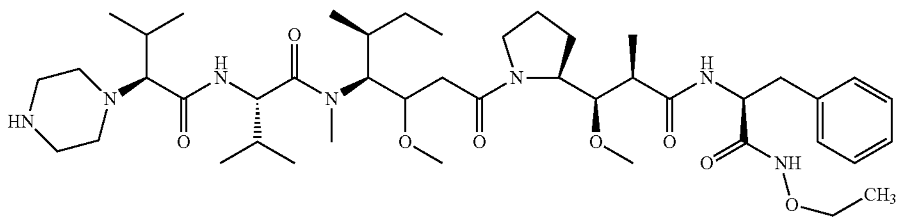 [SMILES: CCONC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N1CCNCC1)C(C)C] | C,A,C,A,D | 2; 1.95; 830.5 |
| 33 | 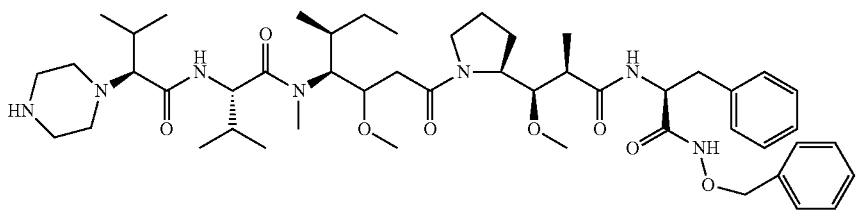 [SMILES: CC[C@H](C)[C@@H](C(CC(=O)N1CCC[C@H]1[C@H](OC)[C@@H](C)C(=O)N[C@@H](Cc1ccccc1)C(=O)NOCc1ccccc1)OC)N(C)C(=O)[C@@H](NC(=O)[C@H](C(C)C)N1CCNCC1)C(C)C] | C,A,C,A,D | 2; 2.10; 892.5 |
| 34 | 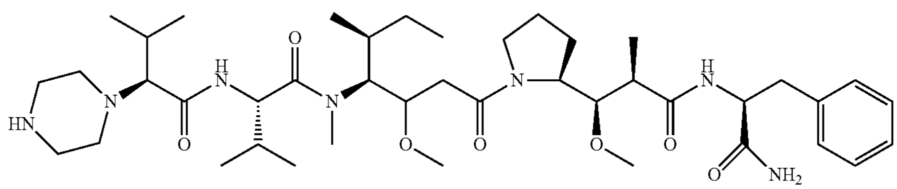 [SMILES: CC[C@H](C)[C@@H](C(CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H](C(C)C)N1CCNCC1)C(C)C] | C,A,C,A,D | 2; 1.87; 786.5 |
| 35 | 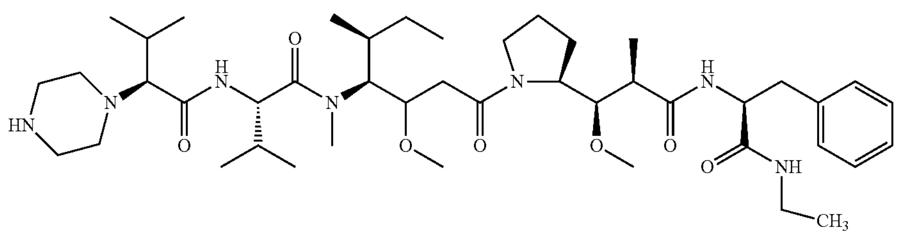 [SMILES: CCNC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N1CCNCC1)C(C)C] | C,A,C,A,D | 2; 1.83; 814.5 |
| 36 | 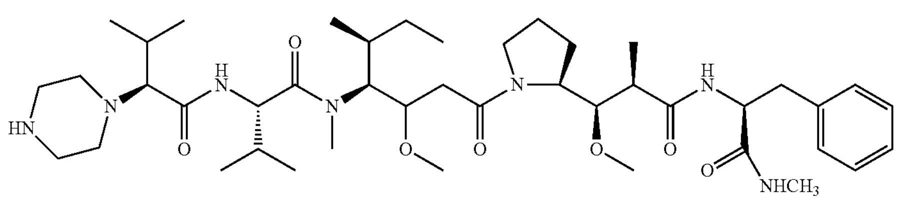 [SMILES: CC[C@H](C)[C@@H](C(CC(=O)N1CCC[C@H]1[C@H](OC)[C@@H](C)C(=O)N[C@@H](Cc1ccccc1)C(=O)NC)OC)N(C)C(=O)[C@@H](NC(=O)[C@H](C(C)C)N1CCNCC1)C(C)C] | C,A,C,A,D | 1; 1.70; 400.9 [1/2(M + 2H)]$^+$ |
| 37 | 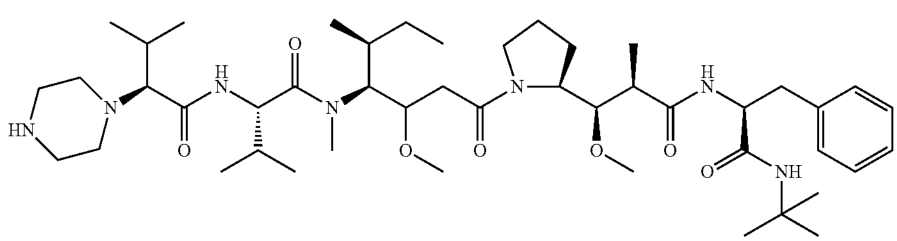 [SMILES: CC[C@H](C)[C@@H](C(CC(=O)N1CCC[C@H]1[C@H](OC)[C@@H](C)C(=O)N[C@@H](Cc1ccccc1)C(=O)NC(C)(C)C)OC)N(C)C(=O)[C@@H](NC(=O)[C@H](C(C)C)N1CCNCC1)C(C)C] | C,A,C,A,D | 2; 1.99; 421.9 [1/2(M + 2H)]$^+$ |

TABLE 5-continued
| Compound | Structure | Synthetic Procedure | LC-MS Method; $R_t$ (min); m/z [M + H]$^+$ |
|---|---|---|---|
| 38 | 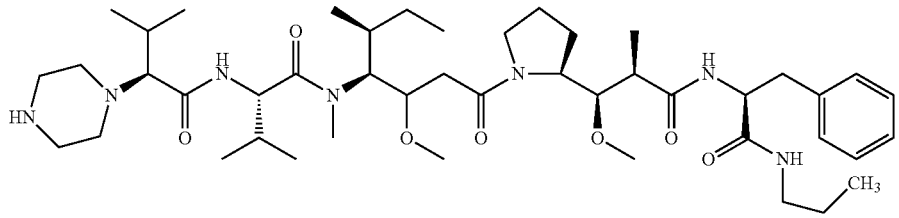 [SMILES: CCCNC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N1CCNCC1)C(C)C] | C,A,C,A,D | 2; 2.00; 828.5 |
| 39 | 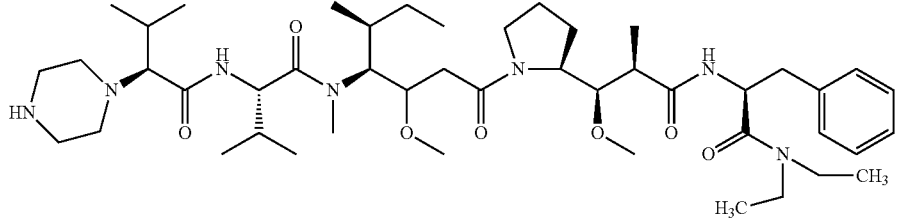 [SMILES: CC[C@H](C)[C@@H](C(CC(=O)N1CCC[C@H]1[C@H](OC)[C@@H](C)C(=O)N[C@@H](Cc1ccccc1)C(=O)N(CC)CC)OC)N(C)C(=O)[C@@H](NC(=O)[C@H](C(C)C)N1CCNCC1)C(C)C] | C,A,C,A,D | 2; 2.10; 842.5 |
| 40 | 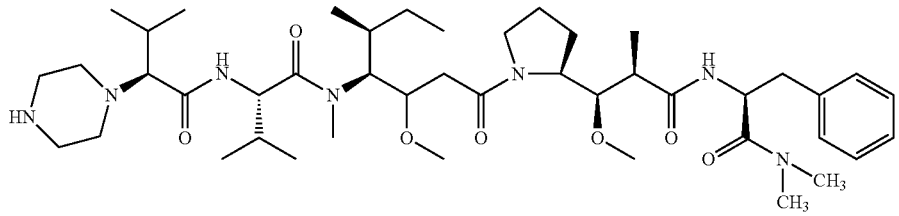 [SMILES: CC[C@H](C)[C@@H](C(CC(=O)N1CCC[C@H]1[C@H](OC)[C@@H](C)C(=O)N[C@@H](Cc1ccccc1)C(=O)N(C)C)OC)N(C)C(=O)[C@@H](NC(=O)[C@H](C(C)C)N1CCNCC1)C(C)C] | C,A,C,A,D | 2; 1.88; 814.5 |
| 41 | 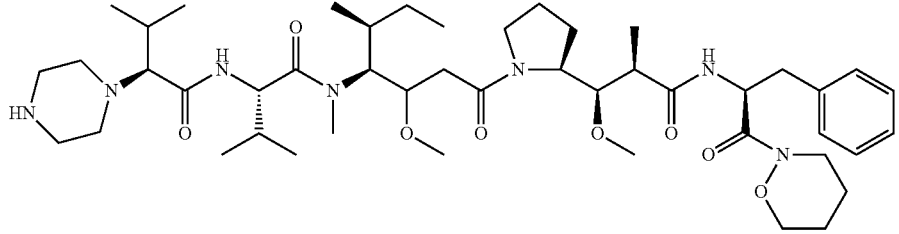 [SMILES: CC[C@H](C)[C@@H](C(CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N1CCNCC1)C(C)C] | C,A,C,A,D | 2; 1.99; 856.5 |
| 43 | 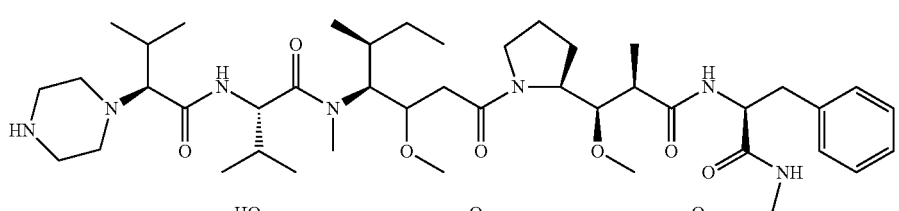 | C,A,C,A,D | 2; 1.88; 1006.6 |
| 44 | 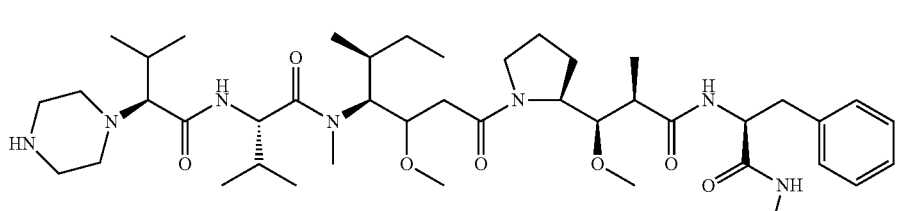 | C,A,C,A,D | 2; 1.78; 1050.6 |

TABLE 5-continued

| Compound | Structure | Synthetic Procedure | LC-MS Method; $R_t$ (min); m/z [M + H]$^+$ |
|---|---|---|---|
| 45 | 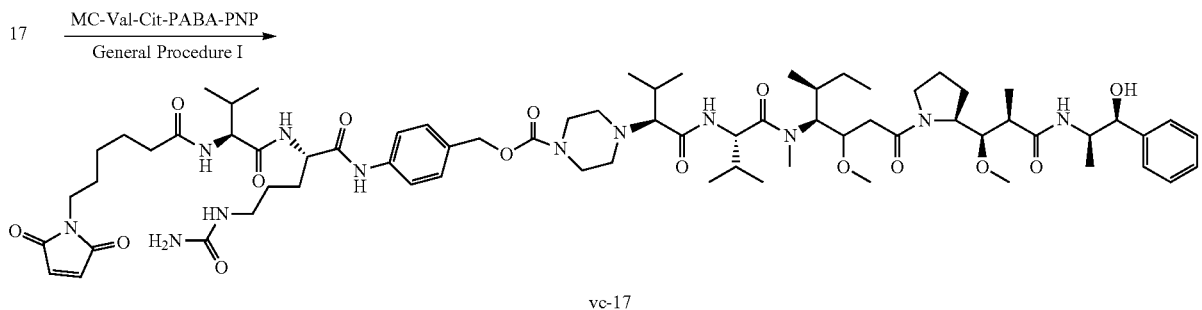 | C,A,C,A,D | 2; 1.85; 932.5 |

Example 15

Synthesis of Linker-Drug Vc-17

Compound MC-Val-Cit-PABA-PNP (43 mg), 17 (30 mg) and HOBt (1 mg) were dissolved in a mixed solvent of pyridine (0.6 mL)/DMF (3 mL), and the reaction mixture was stirred at rt for 24 h. The product was purified by prep-RP-HPLC (Method 3: 35%-55% B in 8 min→95% B in 4 min; $R_t$: 6.2-7.0 min) to give a white solid vc-17 (22 mg). LC-MS (Method 1): $R_t$=1.61 min; m/z (ES$^+$)=686.5 [½(M+2H)]$^+$.

Example 16

Other linker-drugs (vc-Drugs) were synthesized via the similar method as that for vc-17, and Table 6 shows the LC-MS data.

TABLE 6

| Compound | LC-MS Method; $R_t$ (min); m/z [M + H]$^+$ |
|---|---|
| vc-1 | 1; 1.59; 1445.0 |
| vc-2 | 2; 2.05; 1458.9 |
| vc-3 | 2; 2.04; 1142.9 |
| vc-4 | 2; 2.03; 1456.8 |
| vc-5 | 1; 1.70; 742.2 [½(M + 2H)]$^+$ |
| vc-6 | 1; 1.47; 743.0 [½(M + 2H)]$^+$ |
| vc-7 | 2; 2.02; 1442.8 |
| vc-8 | 1; 1.94; 715.5 [½(M + 2H)]$^+$ |
| vc-9 | 2; 2.08; 714.5 [½(M + 2H)]$^+$ |
| vc-10 | 1; 2.00; 707.5 [½(M + 2H)]$^+$ |
| vc-11 | 1; 2.02; 708.5 [½(M + 2H)]$^+$ |
| vc-12 | 1; 1.87; 722.5 [½(M + 2H)]$^+$ |
| vc-13 | 1; 1.87; 715.8 [½(M + 2H)]$^+$ |
| vc-14 | 1; 1.87; 715.6 [½(M + 2H)]$^+$ |

TABLE 6-continued

| Compound | LC-MS Method; $R_t$ (min); m/z [M + H]$^+$ |
|---|---|
| vc-15 | 1; 1.86; 708.5 [½(M + 2H)]$^+$ |
| vc-16 | 1; 1.88; 709.5 [½(M + 2H)]$^+$ |
| vc-18 | 1; 1.47; 1399.5 |
| vc-19 | 2; 2.07; 1341.7 |
| vc-20 | 2; 2.08; 713.0 [½(M + 2H)]$^+$ |
| vc-21 | 1; 1.82; 705.6 |
| vc-31 | 2; 2.00; 1414.7 |
| vc-32 | 2; 2.01; 1428.7 |
| vc-33 | 2; 2.09; 1490.8 |
| vc-34 | 2; 1.97; 1384.8 |
| vc-35 | 2; 2.02; 1412.7 |
| vc-36 | 2; 1.99; 1398.7 |
| vc-37 | 2; 2.11; 1440.8 |
| vc-38 | 2; 2.06; 1426.7 |
| vc-39 | 2; 2.09; 1440.8 |
| vc-40 | 2; 2.01; 1412.7 |
| vc-41 | 2; 2.07; 1454.7 |
| vc-42 | 2; 1.95; 781.0 [½(M + 2H)]$^+$ |
| vc-43 | 2; 1.95; 803.1 [½(M + 2H)]$^+$ |
| vc-44 | 2; 1.94; 825.0 [½(M + 2H)]$^+$ |
| vc-45 | 2; 2.00; 766.0 [½(M + 2H)]$^+$ |

Example 17

Synthesis of Linker-Drug Vc-22

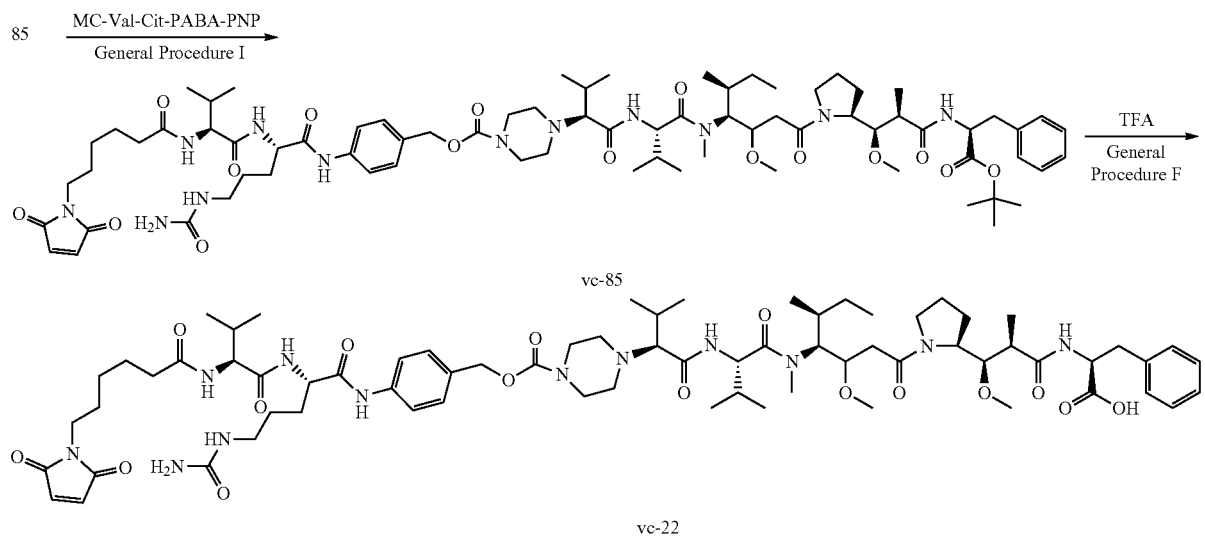

Step 1

Compound MC-Val-Cit-PABA-PNP (39 mg), 85 (30 mg), and HOBt (1 mg) were added to a mixed solvent of pyridine (0.6 mL)/DMF (3 mL), and the reaction mixture was stirred at rt for 24 h. The product was purified by prep-RP-HPLC (Method 3: 40%-70% B in 8 min→95% B in 4 min; $R_t$: 7.4-8.4 min) to give a white solid vc-85 (30 mg). LC-MS (Method 1): $R_t$=1.72 min; m/z (ES$^+$)=721.3 [½(M+2H)]$^+$.

Step 2

Compound vc-85 (30 mg) was dissolved in DCM (2 mL), and the solution was cooled to 0° C., to which TFA (1 mL) was added. The reaction mixture was stirred at 10° C. for 4 h, and then concentrated to remove the solvent. The residue was purified by prep-RP-HPLC (Method 3: 37%-65% B in 8 min→95% B in 4 min; $R_t$: 5.0-6.0 min) to give compound vc-22 (18 mg). LC-MS (Method 1): $R_t$=1.66 min; m/z (ES$^+$)=693.5 [½(M+2H)]$^+$.

Example 18

Other linker-drugs (vc-Drugs) were synthesized via the similar method as that for vc-22, and Table 7 shows the LC-MS data.

TABLE 7

| Compound | LC-MS Method; $R_t$ (min); m/z [M + H]$^+$ |
| --- | --- |
| vc-23 | 1; 1.43; 1399.5 |
| vc-24 | 2; 1.80; 1419.6 |
| vc-25 | 1; 1.57; 697.0 [½(M + 2H)]$^+$ |
| vc-26 | 1; 1.43; 1369.6 |
| vc-27 | 2; 1.78; 700.5 |
| vc-28 | 2; 1.78; 1399.7 |
| vc-29 | 2; 1.73; 1413.7 |
| vc-30 | 2; 1.73; 700.5 [½(M + 2H)]$^+$ |

Example 19

Synthesis of Linker-Drug MC-22

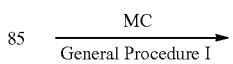

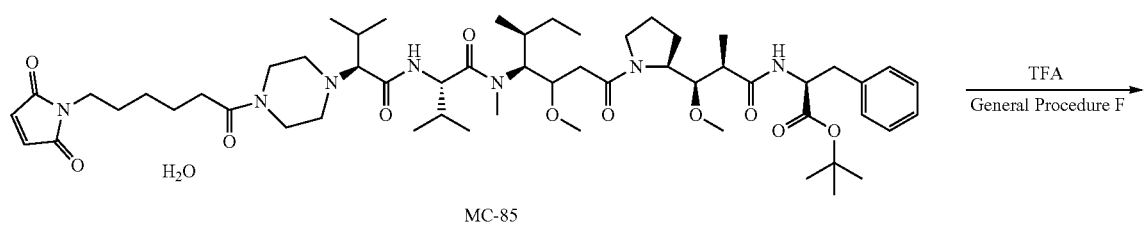

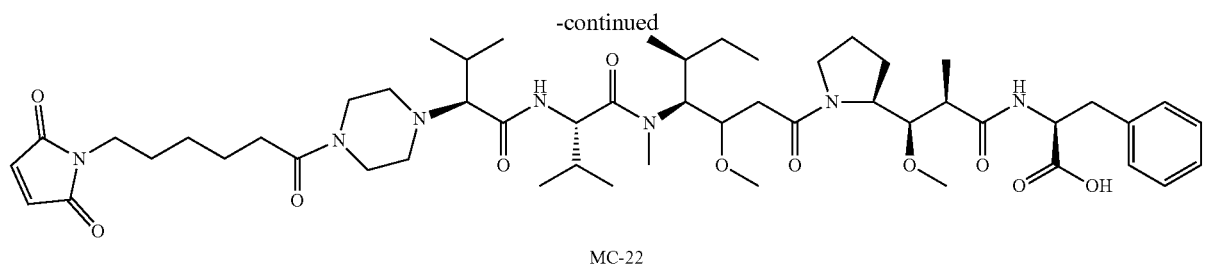

MC-22

Step 1

Compound MC (10 mg) and 85 (30 mg) were dissolved in DCM (5 mL), to which DIEA (14 mg) and HATU (27 mg) were sequentially added. The reaction mixture was stirred at rt for 24 h. The product was purified by prep-RP-HPLC (Method 3: 40%-70% B in 8 min→95% B in 4 min; $R_t$: 7.4-8.6 min) to give a white solid MC-85 (30 mg). LC-MS (Method 1): $R_t$=1.75 min; m/z (ES$^+$)=1036.5 (M+H)$^+$.

Step 2

Compound MC-85 (30 mg) was dissolved in DCM (2 mL), and the solution was cooled to 0° C., to which TFA (1 mL) was added. The reaction mixture was stirred at 10° C. for 4 h, and then concentrated to remove the solvent. The residue was purified by prep-RP-HPLC (Method 3: 35%-60% B in 8 min→95% B in 4 min; $R_t$: 5.5-6.5 min) to give MC-22 (20 mg). LC-MS (Method 1): $R_t$=1.68 min; m/z (ES$^+$)=980.5 (M+H)$^+$.

Example 20

Other linker-drugs (MC-Drugs) were synthesized via the similar method as that for MC-22, and Table 8 shows the LC-MS data.

TABLE 8

| Compound | LC-MS Method; $R_t$ (min); m/z [M + H]$^+$ | Compound | LC-MS Method; $R_t$ (min); m/z [M + H]$^+$ |
|---|---|---|---|
| MC-7 | 2; 2.09; 1037.6 | MC-33 | 1; 1.85; 543.5 [½(M + 2H)]$^+$ |
| MC-18 | 1; 1.43; 980.5 | MC-34 | 2; 2.00; 979.5 |
| MC-19 | 2; 2.12; 468.9 | MC-35 | 2; 2.07; 1007.6 |
| MC-20 | 2; 2.14; 1019.5 | MC-32 | 2; 1.98; 1023.6 |
| MC-21 | 1; 1.87; 1004.6 | MC-36 | 2; 2.02; 993.5 |
| MC-23 | 1; 1.42; 994.5 | MC-37 | 2; 2.11; 1035.5 |
| MC-24 | 2; 1.79; 1014.5 | MC-38 | 2; 2.11; 1021.6 |
| MC-25 | 1; 1.57; 987.4 | MC-39 | 2; 2.15; 1035.6 |
| MC-26 | 1; 1.42; 964.5 | MC-40 | 1; 1.70; 1007.5 |
| MC-27 | 2; 1.77; 994.5 | MC-41 | 2; 2.13; 1049.6 |
| MC-28 | 2; 1.76; 994.5 | MC-42 | 2; 1.98; 1155.7 |
| MC-29 | 2; 1.80; 1002.5 | MC-43 | 2; 1.97; 1199.7 |
| MC-30 | 2; 1.81; 994.6 | MC-44 | 2; 1.97; 622.5 |
| MC-31 | 2; 2.02; 1009.5 | MC-45 | 2; 2.04; 1125.6 |

Example 21

ADCs were synthesized via General Procedure J, and the average DARs for all ADCs were around 4. Table 9 and 10 show the results for cell proliferation inhibition assays (General Procedure L) for the ADCs.

TABLE 9

| ADC | IC$_{50}$ (ng/mL) |
|---|---|
| H-vc-1 | 25.2 |
| H-vc-2 | 19.0 |
| H-vc-3 | 7.0 |
| H-vc-4 | 11.8 |
| H-vc-5 | 23.0 |
| H-vc-6 | 61.4 |
| H-vc-7 | 34.2 |
| H-vc-8 | 60.8 |
| H-vc-9 | 606 |
| H-vc-10 | N/A |
| H-vc-11 | N/A |
| H-vc-12 | 31.7 |
| H-vc-13 | 19.0 |
| H-vc-14 | 34.7 |
| H-vc-15 | 49.7 |
| H-vc-16 | 34.7 |
| H-vc-17 | 5.1 |
| H-vc-18 | 2.0 |
| H-vc-19 | N/A |
| H-vc-20 | 5.7 |
| H-vc-21 | 4.4 |
| H-vc-22 | 2.0 |
| H-vc-23 | 2.9 |
| H-vc-24 | 10.6 |
| H-vc-25 | 5.9 |
| H-vc-26 | 41.4 |
| H-vc-27 | 15.4 |
| H-vc-28 | 96.8 |
| H-vc-29 | 648 |
| H-vc-30 | 11600 |
| H-vc-31 | 4.8 |
| H-vc-32 | 5.1 |
| H-vc-33 | 9.8 |
| H-vc-34 | 5.1 |
| H-vc-35 | 6.2 |
| H-vc-36 | 8.3 |
| H-vc-37 | 78.7 |
| H-vc-38 | 10.2 |
| H-vc-39 | 607 |
| H-vc-40 | 35.1 |
| H-vc-41 | 4.4 |
| H-vc-42 | 4.8 |
| H-vc-43 | 4.9 |
| H-vc-44 | 5.1 |
| H-vc-45 | 8.4 |

TABLE 10

| ADC | IC$_{50}$ (ng/mL) |
|---|---|
| H-MC-5 | 90.2 |
| H-MC-6 | 49.0 |
| H-MC-7 | 3820 |
| H-MC-18 | 67.4 |
| H-MC-19 | 48.9 |
| H-MC-20 | 21.7 |
| H-MC-21 | 28.2 |
| H-MC-22 | 7.1 |
| H-MC-23 | 3.9 |
| H-MC-24 | 30.3 |
| H-MC-25 | 24.7 |
| H-MC-26 | N/A |

TABLE 10-continued

| ADC | IC$_{50}$ (ng/mL) |
|---|---|
| H-MC-27 | 72.0 |
| H-MC-28 | 335 |
| H-MC-29 | 6960 |
| H-MC-30 | 99300 |
| H-MC-31 | 13.0 |
| H-MC-32 | 10.8 |
| H-MC-33 | 15.9 |
| H-MC-34 | 12.7 |
| H-MC-35 | 13.3 |
| H-MC-36 | 19.1 |
| H-MC-37 | N/A |
| H-MC-38 | 9.6 |
| H-MC-39 | N/A |
| H-MC-40 | N/A |
| H-MC-41 | 11.1 |
| H-MC-42 | 16.6 |
| H-MC-43 | 18.1 |
| H-MC-44 | 17.1 |
| H-MC-45 | 19.3 |

The results revealed that some ADCs shows high cell proliferation inhibition activity, and thus the dolastatin 10 derivatives used in these ADCs have further development and application prospect.

All literatures mentioned in the present invention were cited as references, exactly the same as each literature was cited independently as reference. It should be noted that the present invention could be modified by those in the art, which is also within the scope of the claims of the present invention.

What is claimed is:

1. A compound having the formula I:

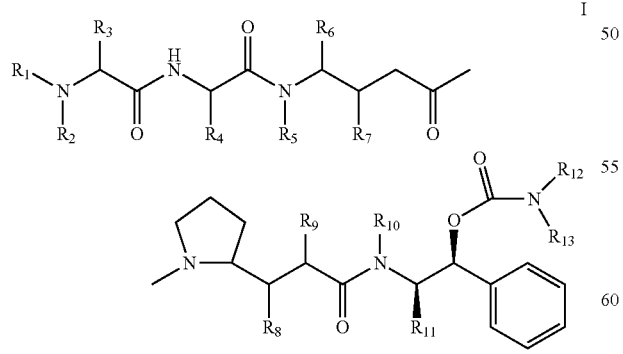

or a pharmaceutically acceptable salt, solvate, or solvate of salt thereof, wherein $R_1$ and $R_2$ are independently selected from H, —$C_1$-$C_8$ alkyl, or $R_1$ and $R_2$ together form a heterocycle of the formula —$(CR_{14}R_{15})_n$—Z—$(CR_{16}R_{17})_m$—, wherein $R_{14}$, $R_{15}$, $R_{16}$ and $R_{17}$ are independently selected from H or —$C_1$-$C_8$ alkyl; Z is selected from O, $NR_{18}$ or $CR_{19}R_{20}$, wherein $R_{18}$, $R_{19}$ and $R_{20}$ are independently selected from H or —$C_1$-$C_8$ alkyl; n and m are integers independently selected from 0 to 8;

$R_3$, $R_4$ and $R_6$ are independently selected from H, —$C_1$-$C_8$ alkyl, aryl, heterocycle, arylalkyl, or heteroarylalkyl; $R_5$, $R_9$, $R_{10}$ and $R_{11}$ are independently selected from H, or —$C_1$-$C_8$ alkyl;

$R_7$ and $R_8$ are independently selected from H, —OH, —$C_1$-$C_8$ alkyl, or —O—($C_1$-$C_8$ alkyl);

$R_{12}$ and $R_{13}$ are independently selected from H, —$C_1$-$C_8$ alkyl, —$OR_{21}$, —$R_{22}$X, or $R_{12}$ and $R_{13}$ together form a heterocycle of the formula —$(CR_{23}R_{24})_p$—W—$(CR_{25}R_{26})_q$—, wherein W is selected from O, $NR_{27}$, or $CR_{28}R_{29}$; X is selected from —OH or —$NR_{30}R_{31}$; p and q are integers independently selected from 0 to 8;

$R_{21}$ is selected from H, —$C_1$-$C_8$ alkyl, aryl, heterocyclyl, arylalkyl, or heteroarylalkyl;

$R_{22}$ is selected from alkylene, alkenlene, alkynlene, arylene, —$(CH_2CH_2O)_r$—$(CH_2)_s$—, or any combination thereof; r and s are integers independently selected from 0 to 8;

$R_{23}$, $R_{24}$, $R_{25}$, $R_{26}$, $R_{27}$, $R_{28}$, $R_{29}$ and $R_{30}$ are independently selected from H or —$C_1$-$C_8$ alkyl;

$R_{31}$ is selected from H, —$C_1$-$C_8$ alkyl, or —$OR_{32}$, wherein $R_{32}$ is selected from H, —$C_1$-$C_8$ alkyl, aryl, heterocyclyl, arylalkyl, or heteroarylalkyl.

2. The compound of claim 1 having the formula II:

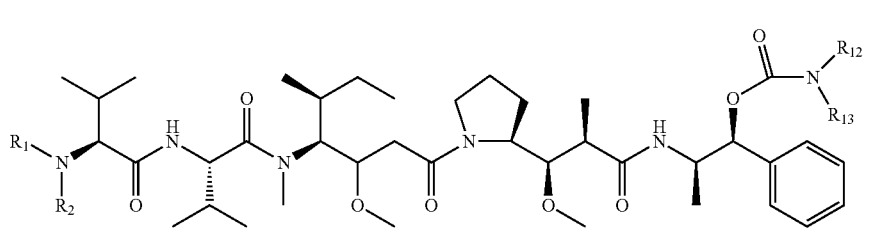

wherein $R_1$ and $R_2$ are independently selected from H or —$C_1$-$C_8$ alkyl, or $R_1$ and $R_2$ together form a heterocycle of the formula —$(CR_{14}R_{15})_n$—Z—$(C\ R_{16}R_{17})_m$—, wherein $R_{14}$, $R_{15}$, $R_{16}$ and $R_{17}$ are independently selected from H or —$C_1$-$C_8$ alkyl; Z is selected from O, $NR_{18}$ or $CR_{19}R_{20}$, wherein $R_{18}$, $R_{19}$, and $R_{20}$ are independently selected from H or —$C_1$-$C_8$ alkyl; n and m are integers independently selected from 0 to 8:

$R_{12}$ and $R_{13}$ are independently selected from H, —$C_1$-$C_8$ alkyl, —$OR_{21}$, —$R_{22}$X, or $R_{12}$ and $R_{13}$ together form a heterocycle of the formula —$(CR_{23}R_{24})_p$—W—$(CR_{25}R_{26})_q$—, wherein W is selected from O, $NR_{27}$, or $CR_{28}R_{29}$; X is selected from —OH or —$NR_{30}R_{31}$; p and q are integers independently selected from 0 to 8;

$R_{21}$ is selected from H, —$C_1$-$C_8$ alkyl, aryl, heterocyclyl, arylalkyl, or heteroarylalkyl;

$R_{22}$ is selected from alkylene, alkenlene, alkynlene, arylene, —$(CH_2CH_2O)_r$—$(CH_2)_s$—, or any combination thereof: r and s are integers independently selected from 0 to 8:

$R_{23}$, $R_{24}$, $R_{25}$, $R_{26}$, $R_{27}$, $R_{28}$, $R_{29}$ and $R_{30}$ are independently selected from H or —$C_1$-$C_8$ alkyl:

$R_{31}$ is selected from H, —$C_1$-$C_8$ alkyl, or —$OR_{32}$, wherein $R_{32}$ is selected from H, —$C_1$-$C_8$ alkyl, aryl, heterocyclyl, arylalkyl, or heteroarylalkyl.

3. A compound of claim 2, and its pharmaceutically acceptable salts, solvate, or solvate of salts, wherein its structure is shown as the following compounds 1-16

| Compound | Number |
|---|---|
| | 1 |
| | 2 |
| | 3 |
| | 4 |
| | 5 |
| | 6 |
| | 7 |

| Compound | Number |
|---|---|
| | 8 |
| | 9 |
| | 10 |
| | 11 |
| | 12 |
| | 13 |
| | 14 |

| Compound | Number |
|---|---|
| 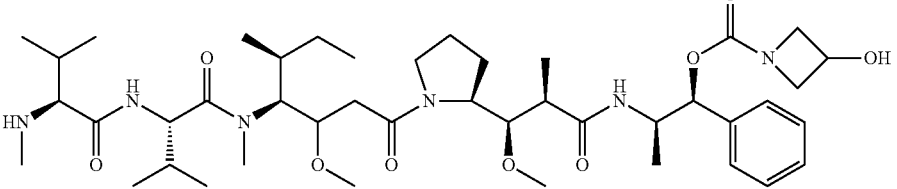 | 15 |
| 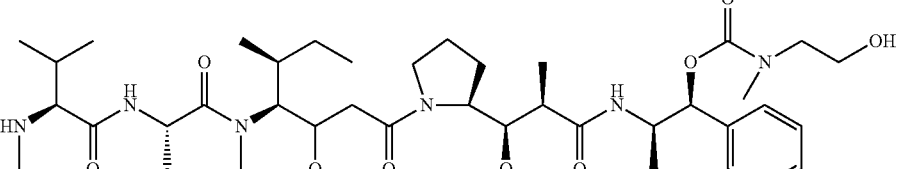 | 16. |

4. A compound having the formula III:

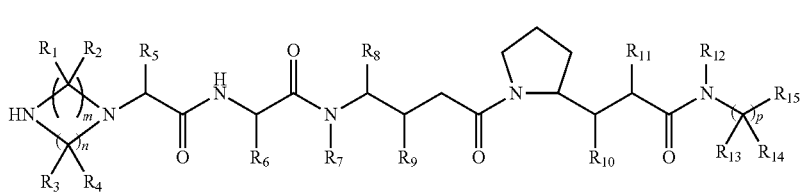

III or a pharmaceutically acceptable salt, solvate, or solvate of salt thereof, wherein $R_1$, $R_2$, $R_3$ and $R_4$ are independently selected from H or —$C_1$-$C_8$ alkyl;

m and n are integers independently selected from 2 m 4;

$R_5$, $R_6$ and $R_8$ are independently selected from H, —$C_1$-$C_8$ alkyl, aryl, heterocyclyl, Arylalkyl, heteroarylalkyl;

$R_7$, $R_{11}$ and $R_{12}$ are independently selected from H or —$C_1$-$C_8$ alkyl;

$R_9$ and $R_{10}$ are independently selected from H, —OH, —$C_1$-$C_8$ alkyl, or —O—($C_1$-$C_8$ alkyl);

$R_{13}$ and $R_{14}$ are independently selected from H, —OH, —$OR_{16}$, —$C_1$-$C_8$ alkyl, aryl, heterocyclyl, arylalkyl, heteroarylalkyl;

$R_{16}$ is selected from H or —$C_1$-$C_8$ alkyl:

p is an integer ranging from 1 to 8;

$R_{15}$ is selected from —$C_3$-$C_8$ alkyl, aryl, —$C_3$-$C_8$ heterocyclyl, —COOH, or —C(=O)$NR_{17}R_{18}$, $R_{17}$ and $R_{18}$ are independently selected from H, —$C_1$-$C_8$ alkyl, —OH, —$OR_{19}$, or $R_{17}$ and $R_{18}$ together form a cycle of the formula —$(CR_{20}R_{21})_o$—Z—$(CR_{22}R_{23})_q$—, wherein $R_{19}$, $R_{20}$, $R_{21}$, $R_{22}$ and $R_{23}$ are independently selected from H, —$C_1$-$C_8$ alkyl, aryl, heterocyclyl, arylalkyl, or heteroarylalkyl; Z is selected from O, $NR_{24}$, or $CR_{25}R_{26}$, wherein $R_{24}$, $R_{25}$ and $R_{26}$ are independently selected from H, or —$C_1$-$C_8$ alkyl; o and q are integers independently selected from 0 to 8.

5. A compound of claim 4 and its pharmaceutically acceptable salts, solvate, or solvate of salts, wherein its structure is shown as formula IV

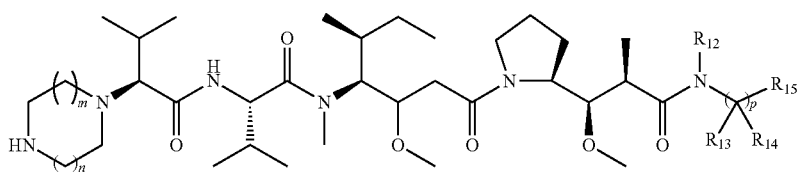

IV wherein m and o are integers independently selected from 2 to 4;

$R_{12}$ is selected from H or —$C_1$-$C_8$ alkyl;

$R_{13}$ and $R_{14}$ are independently selected from H, —OH, —$OR_{16}$, —$C_1$-$C_8$ alkyl, aryl, heterocyclyl, arylalkyl, heteroarylalkyl;

$R_{16}$ is selected from H or —$C_1$-$C_8$ alkyl;

p is an integer ranging from 1 to 8;

$R_{15}$ is selected from —$C_3$-$C_8$ alkyl, aryl, —$C_3$-$C_8$ heterocyclyl, —COOH, or —C(=O)$NR_{17}R_{18}$;

$R_{17}$ and $R_{18}$ are independently selected from H, —$C_1$-$C_8$ alkyl, —OH, —$OR_{19}$, or $R_{17}$ and $R_{18}$ together form a cycle of the formula —$(CR_{20}R_{21})_o$—Z—$(CR_{22}R_{23})_q$—, wherein $R_{19}$, $R_{20}$, $R_{21}$, $R_{22}$ and $R_{23}$ are independently selected from H, —$C_1$-$C_8$ alkyl, aryl, heterocyclyl, arylalkyl, heteroarylalkyl; Z is selected from O, $NR_{24}$, or $CR_{25}R_{26}$, wherein $R_{24}$, $R_{25}$ and $R_{26}$ are independently selected from H, —$C_1$-$C_8$ alkyl; o and q are integers independently selected from 0 to 8.

6. A compound of claim 5, and its pharmaceutically acceptable salts, solvate, or solvate of salts, wherein its structure is shown as the following compounds 17-45

| Compound | Number |
|---|---|
| [structure] | 17 |
| [structure] | 18 |
| [structure] | 19 |
| [structure] | 20 |
| [structure] | 21 |
| [structure] | 22 |
| [structure] | 23 |

| Compound | Number |
|---|---|
| 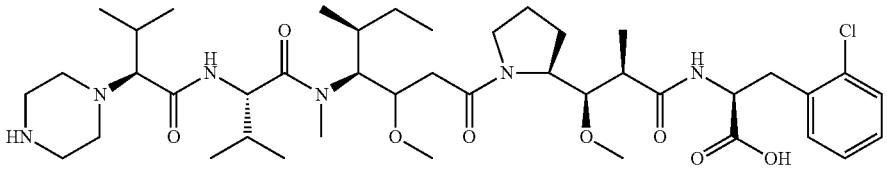 [SMILES: CC[C@H](C)[C@@H](C(CC(=O)N1CCC[C@H]1[C@H](OC)[C@@H](C)C(=O)N[C@@H](Cc1ccccc1Cl)C(=O)O)OC)N(C)C(=O)[C@@H](NC(=O)[C@H](C(C)C)N1CCNCC1)C(C)C] | 24 |
| 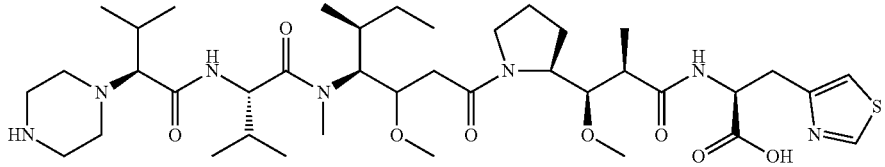 [SMILES: CC[C@H](C)[C@@H](C(CC(=O)N1CCC[C@H]1[C@H](OC)[C@@H](C)C(=O)N[C@@H](Cc1cscn1)C(=O)O)OC)N(C)C(=O)[C@@H](NC(=O)[C@H](C(C)C)N1CCNCC1)C(C)C] | 25 |
| 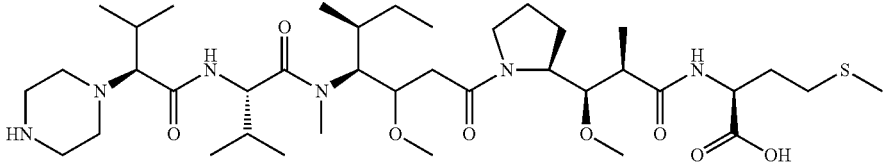 [SMILES: CC[C@H](C)[C@@H](C(CC(=O)N1CCC[C@H]1[C@H](OC)[C@@H](C)C(=O)N[C@@H](CCSC)C(=O)O)OC)N(C)C(=O)[C@@H](NC(=O)[C@H](C(C)C)N1CCNCC1)C(C)C] | 26 |
| 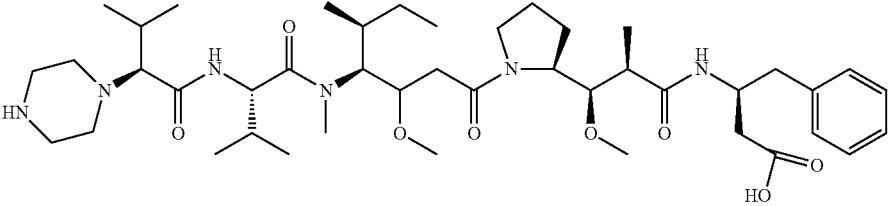 [SMILES: CC[C@H](C)[C@@H](C(CC(=O)N1CCC[C@H]1[C@H](OC)[C@@H](C)C(=O)N[C@H](CC(=O)O)Cc1ccccc1)OC)N(C)C(=O)[C@@H](NC(=O)[C@H](C(C)C)N1CCNCC1)C(C)C] | 27 |
| 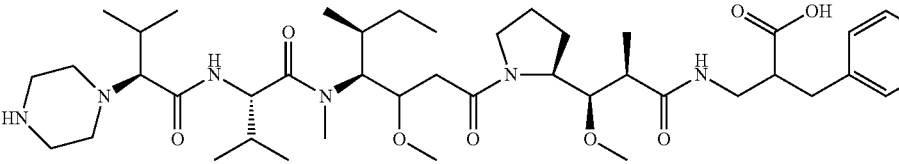 | 28 |
| 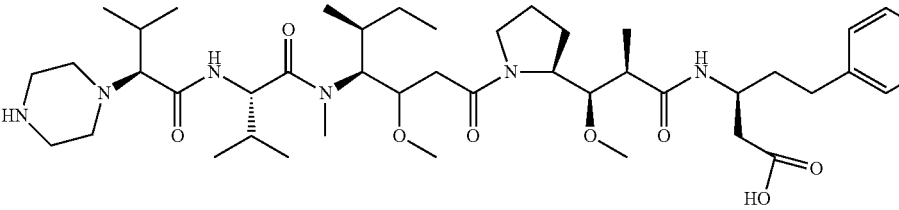 | 29 |
| 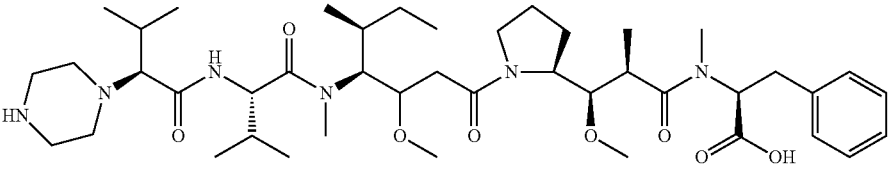 [SMILES: CC[C@H](C)[C@@H](C(CC(=O)N1CCC[C@H]1[C@H](OC)[C@@H](C)C(=O)N(C)[C@@H](Cc1ccccc1)C(=O)O)OC)N(C)C(=O)[C@@H](NC(=O)[C@H](C(C)C)N1CCNCC1)C(C)C] | 30 |
| 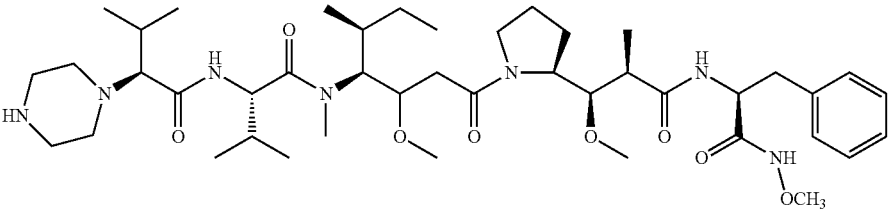 [SMILES: CC[C@H](C)[C@@H](C(CC(=O)N1CCC[C@H]1[C@H](OC)[C@@H](C)C(=O)N[C@@H](Cc1ccccc1)C(=O)NOC)OC)N(C)C(=O)[C@@H](NC(=O)[C@H](C(C)C)N1CCNCC1)C(C)C] | 31 |

|  Compound | Number |
|---|---|
| 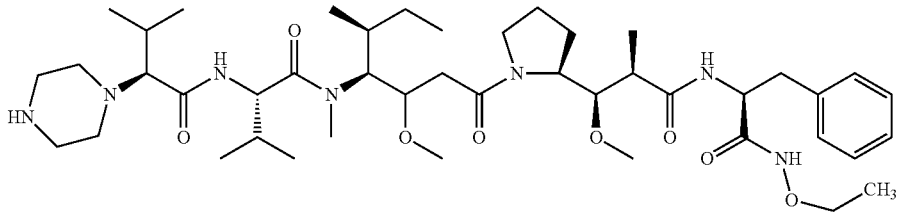 [SMILES: CCONC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N1CCNCC1)C(C)C] | 32 |
| 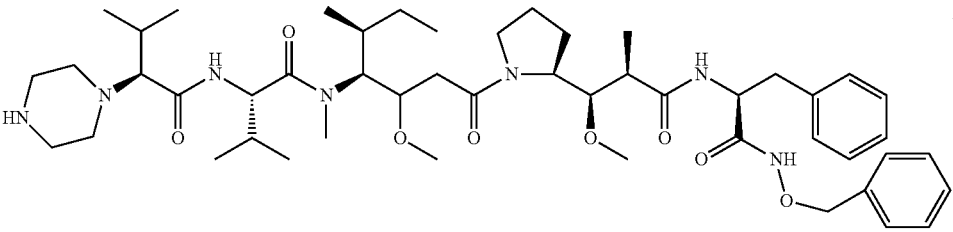 [SMILES: CC[C@H](C)[C@@H](C(CC(=O)N1CCC[C@H]1[C@H](OC)[C@@H](C)C(=O)N[C@@H](Cc1ccccc1)C(=O)NOCc1ccccc1)OC)N(C)C(=O)[C@@H](NC(=O)[C@H](C(C)C)N1CCNCC1)C(C)C] | 33 |
| 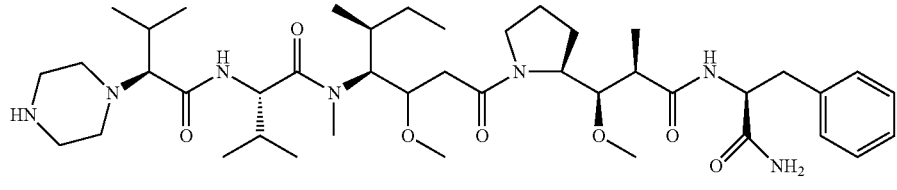 [SMILES: CC[C@H](C)[C@@H](C(CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H](C(C)C)N1CCNCC1)C(C)C] | 34 |
| 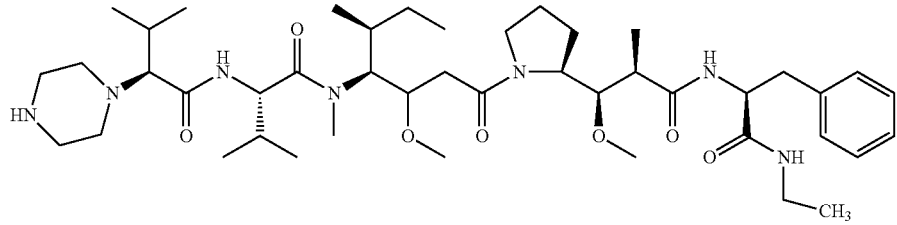 [SMILES: CCNC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N1CCNCC1)C(C)C] | 35 |
| 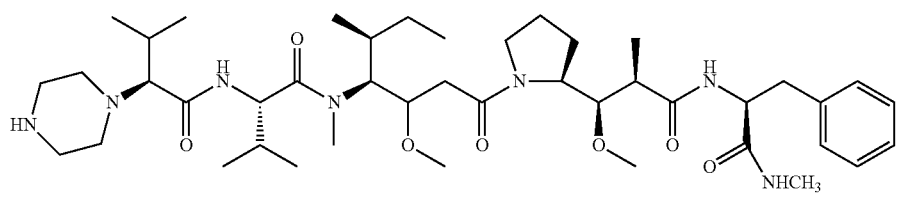 [SMILES: CC[C@H](C)[C@@H](C(CC(=O)N1CCC[C@H]1[C@H](OC)[C@@H](C)C(=O)N[C@@H](Cc1ccccc1)C(=O)NC)OC)N(C)C(=O)[C@@H](NC(=O)[C@H](C(C)C)N1CCNCC1)C(C)C] | 36 |
| 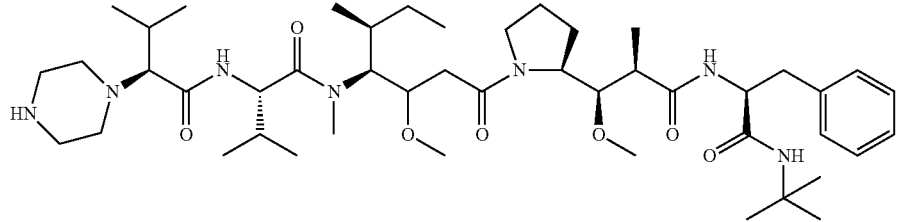 [SMILES: CC[C@H](C)[C@@H](C(CC(=O)N1CCC[C@H]1[C@H](OC)[C@@H](C)C(=O)N[C@@H](Cc1ccccc1)C(=O)NC(C)(C)C)OC)N(C)C(=O)[C@@H](NC(=O)[C@H](C(C)C)N1CCNCC1)C(C)C] | 37 |
| 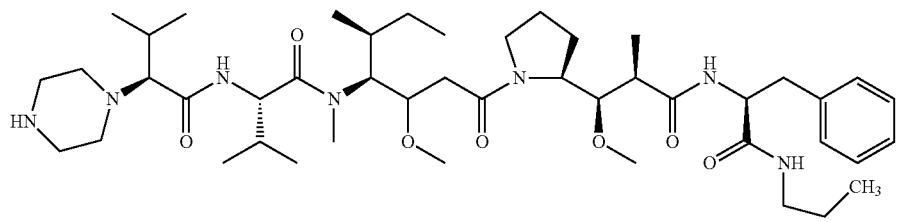 [SMILES: CCCNC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N1CCNCC1)C(C)C] | 38 |

| Compound | Number |
|---|---|
| | 39 |
| | 40 |
| | 41 |
| | 42 |
| | 43 |
| | 44 |

| Compound | Number |
|---|---|
| 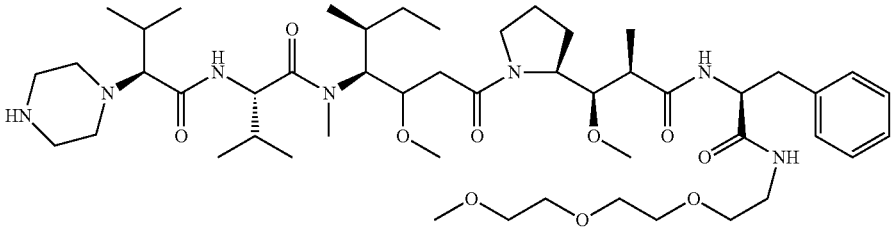 [SMILES: CC[C@H](C)[C@@H](C(CC(=O)N1CCC[C@H]1[C@H](OC)[C@@H](C)C(=O)N[C@@H](Cc1ccccc1)C(=O)NCCOCCOCCOC)OC)N(C)C(=O)[C@@H](NC(=O)[C@H](C(C)C)N1CCNCC1)C(C)C] | 45. |

7. A pharmaceutical composition comprising the compound in accordance with claim 1, or a pharmaceutically acceptable salt, a solvate, or a solvate of salt thereof and a pharmaceutically acceptable carrier.

8. An antibody-drug conjugate having the formula V:

L-(A-D)$_n$   V wherein L is an antibody, antibody fragment, or protein; A is a linker part; D is the compound in accordance with claim 1, or a pharmaceutically acceptable salt, a solvate, or a solvate of salt thereof; n is an integer ranging from 1 to 8.

9. A method of treating cancer, wherein a patient is supplied with an effective amount of an antibody drug conjugate of claim 8.

10. An antibody-drug conjugate having the formula VI:

L-(A-D)$_n$   VI wherein L is an antibody, antibody fragment, or protein; A is a linker part; D is the compound in accordance with claim 2, or a pharmaceutically acceptable salt, a solvate, or a solvate of salt thereof; n is an integer ranging from 1 to 8.

11. A method of treating cancer, wherein a patient is supplied with an effective amount of an antibody drug conjugate of claim 10.

12. An antibody-drug conjugate having the formula VII:

L-(A-D)$_n$   VI wherein L is an antibody, antibody fragment, or protein; A is a linker part; D is the compound in accordance with claim 4, or a pharmaceutically acceptable salt, a solvate, or a solvate of salt thereof; n is an integer ranging from 1 to 8.

13. A method of treating cancer, wherein a patient is supplied with an effective amount of an antibody drug conjugate of claim 12.

14. An antibody-drug conjugate having the formula VIII:

L-(A-D)$_n$   VIII wherein L is an antibody, antibody fragment, or protein; A is a linker part; D is the compound in accordance with claim 5, or a pharmaceutically acceptable salt, a solvate, or a solvate of salt thereof; n is an integer ranging from 1 to 8.

15. A method of treating cancer, wherein a patient is supplied with an effective amount of an antibody drug conjugate of claim 14.

16. A pharmaceutical composition comprising the compound in accordance with claim 2, or a pharmaceutically acceptable salt, a solvate, or a solvate of salt thereof and a pharmaceutically acceptable carrier.

17. A pharmaceutical composition comprising the compound in accordance with claim 4, or a pharmaceutically acceptable salt, a solvate, or a solvate of salt thereof and a pharmaceutically acceptable carrier.

18. A pharmaceutical composition comprising the compound in accordance with claim 5, or a pharmaceutically acceptable salt, a solvate, or a solvate of salt thereof and a pharmaceutically acceptable carrier.

* * * * *